US010947543B2

(12) United States Patent
Pyle et al.

(10) Patent No.: US 10,947,543 B2
(45) Date of Patent: Mar. 16, 2021

(54) INTERFERON PRODUCTION USING SHORT RNA DUPLEXES

(71) Applicant: Yale University, New Haven, CT (US)

(72) Inventors: Anna Marie Pyle, Guilford, CT (US); Andrew Kohlway, Santa Clara, CA (US); Dahai Luo, Proteos (SG); David Rawling, San Mateo, CA (US); Akiko Iwasaki, Guilford, CT (US)

(73) Assignee: Yale University, New Haven, CT (US)

( * ) Notice: Subject to any disclaimer, the term of this patent is extended or adjusted under 35 U.S.C. 154(b) by 0 days.

(21) Appl. No.: 14/776,463

(22) PCT Filed: Mar. 13, 2014

(86) PCT No.: PCT/US2014/025578
§ 371 (c)(1),
(2) Date: Sep. 14, 2015

(87) PCT Pub. No.: WO2014/159990
PCT Pub. Date: Oct. 2, 2014

(65) Prior Publication Data
US 2016/0046943 A1 Feb. 18, 2016

Related U.S. Application Data

(60) Provisional application No. 61/779,514, filed on Mar. 13, 2013.

(51) Int. Cl.
*C12N 15/115* (2010.01)
*A61K 38/21* (2006.01)
*A61K 31/713* (2006.01)
*A61K 45/06* (2006.01)

(52) U.S. Cl.
CPC .......... *C12N 15/115* (2013.01); *A61K 31/713* (2013.01); *A61K 38/212* (2013.01); *A61K 38/215* (2013.01); *A61K 45/06* (2013.01); *C12N 2310/531* (2013.01); *C12N 2320/30* (2013.01)

(58) Field of Classification Search
None
See application file for complete search history.

(56) References Cited

U.S. PATENT DOCUMENTS

| | | | | |
|---|---|---|---|---|
| 2007/0224186 A1* | 9/2007 | Kulaksiz | ................ | C07K 16/26 424/130.1 |
| 2007/0269448 A1* | 11/2007 | Schramm | ................ | C12N 15/11 424/183.1 |
| 2007/0270360 A1 | 11/2007 | McSwiggen | | |
| 2008/0293053 A1* | 11/2008 | Keller | ................ | C12N 15/1135 435/6.17 |
| 2009/0123501 A1* | 5/2009 | Levitt | ................ | A61K 39/0011 424/277.1 |
| 2009/0247613 A1* | 10/2009 | McSwiggen | ..... | A61K 47/48023 514/44 R |
| 2011/0097390 A1* | 4/2011 | Ambati | ............. | A01K 67/0276 424/450 |
| 2011/0123520 A1 | 5/2011 | Manoharan | | |
| 2011/0165123 A1 | 7/2011 | Hartmann | | |
| 2011/0251258 A1* | 10/2011 | Samarsky | ............. | C12N 15/111 514/44 A |
| 2012/0088815 A1 | 4/2012 | Liang | | |
| 2012/0329857 A1* | 12/2012 | Ge | ........................ | C12N 15/111 514/44 A |
| 2014/0024819 A1* | 1/2014 | Ludwig | .................. | C07H 21/02 536/23.1 |
| 2016/0040161 A1* | 2/2016 | Packard | ............. | A61K 48/0025 514/44 A |

OTHER PUBLICATIONS

Ge et al (RNA (2010), 16:106-117, with Supplementary Table).*
Poeck et al (Nature Medicine 14(11): 1256-1263, 2008).*
DeGuzman et al (Nucleic Acids Research, 2006, vol. 34, No. 22 6425-6437) (Year: 2006).*
Kohlway et al (EMBO Reports 14(9): 772-779, 2014) (Year: 2014).*
Ge et al (RNA (2010), 16:118-130) (Year: 2010).*
Guo et al (RNA 16:118-130, 2010) (Year: 2010).*
Schlee et al (Immunity 31, 25-34, Jul. 17, 2009) (Year: 2009).*
Schlee et al (Mol. Ther. 18(7): 1254-1262, 2010) (Year: 2010).*
5'ppp-dsRNA, Technical Data Sheet, Invivogen (http://www.invivogen.com/PDF/5pppRNA_TDS.pdf), accessed Jan. 2013.
Abdullah et al, "RIG-I detects infection with live Listeria by sensing secreted bacterial nucleic acids," 2012, EMBO J, 31:4153-4164.
Ablasser et al., "RIG-I dependent sensing of poly(dA-dT) via the induction of an RNA polymerase III transcribed RNA intermediate." 2009, Nat Immunol, 10:1065-1072.
Bamming and Horvath, "Regulation of Signal Transduction by Enzymatically Inactive Antiviral RNA Helicase Proteins MDA5, RIG-I, and LGP2," 2009, J Biol Chem, 284:9700-9712.
Beckham et al., "Conformational rearrangements of RIG-I receptor on formation of a multiprotein:dsRNA assembly," Nucleic Acids Research, 2013, vol. 41(5):3436-3445.
Berke and Modis, "MDA5 cooperatively forms dimers and ATP-sensitive filaments upon binding double-stranded RNA," 2012, EMBO J, 31:1714-1726.
Berke et al., "MDA5 assembles into a polar helical filament on dsRNA," 2012, Proc Natl Acad Sci USA, 109:18437-18441.
Binder et al., "Molecular Mechanism of Signal Perception and Integration by the Innate Immune Sensor Retinoic Acid-inducible Gene-I (RIG-I)," 2011, J Biol Chem, 286(31):27278-87.
Chiu et al., "RNA Polymerase III Detects Cytosolic DNA and Induces Type-I Interferons Through the RIG-I Pathway," 2009, Cell, 138:576-591.
Civril et al., "The RIG-I ATPase domain structure reveals insights into ATP-dependent antiviral signaling," 2011, EMBO Rep, 12:1127-1134.

(Continued)

*Primary Examiner* — Richard A Schnizer
(74) *Attorney, Agent, or Firm* — Saul Ewing Arnstein & Lehr LLP; Kathryn Doyle; Domingos J. Silva

(57) ABSTRACT

The present invention provides a small hairpin nucleic acid molecule that is capable of stimulating interferon production. The nucleic acid molecule of the present invention has a double-stranded section of less than 19 base pairs and at least one blunt end. In certain embodiments, the molecule comprises a 5' triphosphate or a 5' diphosphate.

21 Claims, 15 Drawing Sheets

Specification includes a Sequence Listing.

(56) References Cited

OTHER PUBLICATIONS

Feng et al., "Structural and biochemical studies of RIG-I antiviral signaling," Protein Cell, 2013, 4(2):142-154.
Gack et al., "TRIM25 RING-finger E3 ubiquitin ligase is essential for RIG-I-mediated antiviral activity," 2007, Nature, 446:916-920.
Hwang et al., "50-Triphosphate-RNA-independent activation of RIG-I via RNA aptamer with enhanced antiviral activity," 2012, Nucleic Acids Res, 40(6):2724-33.
Jiang et al., "Structural Basis of RNA Recognition and Activation by Innate Immune Receptor RIG-I," 2011, Nature, 479:423-427.
Jiang et al., "Ubiquitin-Induced Oligomerization of the RNA Sensors RIG-I and MDA5 Activates Antiviral Innate Immune Response," 2012, Immunity, 36:959-973.
Kageyama et al., "55 Amino acid linker between helicase and carboxyl terminal domains of RIG-I functions as a critical repression domain and determines inter-domain conformation," 2011, Biochem Biophys Res Commun, 415:75-81.
Kato et al., "Length-dependent recognition of doublestranded ribonucleic acids by retinoic acid—inducible gene-I and melanoma differentiation—associated gene 5," 2008, J Exp Med, 205:1601-1610.
Kato et al., "RIG-I-like receptors: cytoplasmic sensors for non-self RNA," 2011, Immunol Rev, 243:91-98.
Kohlway et al., "Defining the functional determinants for RNA surveillance by RIG-I," 2013, EMBO Rep, 14(9):772-9.
Kolakofsky et al., "A structure-based model of RIG-I activation," 2012, RNA, 18:2118-2127.
Kowalinski et al., "Structural Basis for the Activation of Innate Immune Pattern-Recognition Receptor RIG-I by Viral RNA," 2011, Cell, 147:423-435.
Li et al., 2007, "Adjuvant effects of plasmid-generated hairpin RNA molecules on DNA vaccination," Vaccine, 25:6992-7000.
Lu et al., "Crystal structure of RIG-I C-terminal domain bound to blunt-ended double-strand RNA without 5' triphosphate," 2011, Nucleic Acids Res, 39:1565-1575.
Lu et al., "The Structural Basis of 5' Triphosphate Double-stranded RNA Recognition by RIG-I C-terminal Domain," 2010, Structure, 18:1032-1043.
Luo et al., "Duplex RNA activated ATPases (DRAs): platforms for RNA sensing, signaling and processing," RNA Biol., 10:1, 111-120; Jan. 2013.
Luo et al., "Structural insights into RNA recognition by RIG-I," 2011, Cell, 147:409-422.
Luo et al., "Visualizing the determinants of viral RNA recognition by innate immune sensor RIG-I," 2012, Structure, 20:1983-1988.
Malathi et al., "RNase L releases a small RNA from HCV RNA that refolds into a potent PAMP," 2010, RNA, 16: 2108-2119.
Malathi et al., "Small self-RNA generated by RNase L amplifies antiviral innate immunity" 2007, Nature, 448:816-819.
Martinez-Gil et al., 2013, "A Sendai virus derived RNA agonist of RIG-I as a viral vaccine adjuvant," J Virol, 87(3): 1290-1300.
Peisley et al., "Cooperative assembly and dynamic disassembly of MDA5 filaments for viral dsRNA recognition," 2011, Proc Natl Acad Sci USA, 108: 21010-21015.
Pyle, "Translocation and Unwinding Mechanisms of RNA and DNA Helicases," 2008, Annu Rev Biophys, 37:317-336.
Ramos and Gale, "RIG-I like receptors and their signaling crosstalk in the regulation of antiviral immunity," 2011, Curr Opin Virol, 1:167-176.
Saito et al., "Regulation of innate antiviral defenses through a shared repressor domain in RIG-I and LGP2," 2007, Proc Natl Acad Sci USA, 104:582-587.
Satoh et al., "LGP2 is a positive regulator of RIG-I- and MDA5-mediated antiviral responses," 2010, Proc Natl Acad Sci USA, 107:1512-1517.
Schlee et al., 2009, "Recognition of 5' Triphosphate by RIG-I Helicase Requires Short Blunt Double-Stranded RNA as Contained in Panhandle of Negative-Strand Virus," Immunity, 31:25-34.
Schmidt et al., "5_-triphosphate RNA requires base-paired structures to activate antiviral signaling via RIG-I," PNAS, Jul. 21, 2009, 106(29):12067-12072.
Vela et al., "The Thermodynamic Basis for Viral RNA Detection by the RIG-I Innate Immune Sensor," 2012, J Biol Chem, 287:42564-42573.
Wang et al., "Structural and functional insights into 5'-ppp RNA pattern recognition by the innate immune receptor RIG-I," 2010, Nat Struct Mol Biol, 17:781-787.

* cited by examiner

INTERFERON PRODUCTION USING SHORT RNA DUPLEXES

CROSS-REFERENCE TO RELATED APPLICATIONS

This application is the U.S. national stage application filed under 35 U.S.C. § 371 claiming benefit to International Patent Application No. PCT/US14/25578, filed Mar. 13, 2014, which is entitled to priority under 35 U.S.C. § 119(e) to U.S. Provisional Application No. 61/779,514, filed Mar. 13, 2013, each of which is hereby incorporated by reference in its entirety.

STATEMENT REGARDING FEDERALLY SPONSORED RESEARCH OR DEVELOPMENT

This invention was made with government support under RO1 AI089826-03 awarded by the National Institutes of Health (NIH). The government has certain rights in the invention.

BACKGROUND OF THE INVENTION

Retinoic acid-inducible gene it (RIG-I) melanoma differentiation-associated gene 5 (MDA5) and laboratory of genetics and physiology 2(LGP2), comprise the RIG-I like receptor (RLR) class of intracellular pattern recognition receptors (PRRs) that defend against bacterial and viral infection by recognizing foreign RNAs in the cytoplasm and eliciting an innate immune response through the production of pro-inflammatory cytokines and type I interferons (Abdullah et at, 2012, EMBO J 31:4153-4164; Kato et al., 2011, Immunol Rev 243:91-98; Ramos and Gale, 2011; Curr Opin Virol 1:167-176). RIG-I recognizes both self and non-self RNA, including positive and negative stranded RNA viruses; RNA fragments produced by RNA Polymerase III either from DNA viruses like the Epstein-Barr virus or AT-rich double stranded DNA templates (Ablasser et al., 2009, Nat Immunol 10:1065-1072; Chiu et. al., 2009, Cell 138:576-591), RNA cleavage products of the antiviral endoribonuclease RNAse L (Malathi et al., 2007, Nature 448:816-819; Malathi et al., 2010 RNA 16: 2108-2119), synthetic poly I:C (Kato et al., 2008, J Exp Med 205:1601-1610), and even RNA aptamers lacking a 5'triphosphate (Hwang et al., 2012, Nucleic Acids Res 40(6):2724-33). Of these substrates, the simplest RNA molecule commonly reported to activate the RIG-I signaling pathway is 5' triphosphorylated, blunt-ended 19-mer duplex RNA (Schlee et al., 2009, Immunity 31:25-34; Schmidt et al., 2009, Proc Natl Acad Sci USA 106:12067-12072). Moreover, RIG-I exhibits a strong preference for 5'triphosphorylated blunt ends of duplex RNA, and will tolerate 3' but not 5' overhangs (Schlee et al., 2009, Immunity 31:25-34). RIG-I's distinct pathogen associated molecular pattern (PAMP) is therefore defined as duplex RNA containing a 5'triphosphate moiety, although only duplex RNA appears to be absolutely required for RIG-I recognition (Lu et al., 2011, Nucleic Acids Res 39:1565-1575).

RLRs are part of a larger group of duplex RNA activated ATPases (DRAs) that also includes Dicer and Dicer-Related Helicases (DRHs) (Luo et al, 2012a, RNA Biol. 2012 Dec. 10; 10(1)). Besides recognizing duplex RNA, these helicases share the common characteristic that they do not function as conventional helicases (i.e., they do not catalyze strand separation) (Luo et al., 2012, RNA Biol. 2012 Dec. 10; 10(1); Pyle, 2008, Annu Rev Biophys 37:317-336). DRAs share a common superfamily 2 helicase core comprised of two RecA-like domains, HEL1 and HEL2, and a conserved insertion domain in HEL2, Hel2i. Except Dicer, DRAs contain a conserved C-terminal domain (CTD), responsible for modulating the function of each helicase and imparting substrate RNA specificity. In RIG-I, the CID provides this specificity by recognizing 5'triphosphates (Lu et at, 2010, Structure 18:1032-4043; Wang et al., 2010, Nat Struct Mol Biol 17:781-787). Initially, the RIG-4 CTD was incorrectly annotated as a repressor domain (Saito et al., 2007, Proc Natl Acad Sci USA 104:582-587), however mutant RIG-I constructs lacking a CTD are unable to stimulate an interferon response (Kageyama et al., 2011, Biochem Biophys Res Commun 415:75-81), suggesting a role for the CTD beyond autorepression.

RIG-I and MDA5 are unique among DRAs because they contain tandem caspase activation and recruitment domains (CARDs) at their N-termini that undergo ubiquitination upon substrate binding and subsequently initiate downstream signaling by interacting with the CARD domain of the mitochondrial adaptor protein MAVS (Jiang et al., 2012, Immunity 36:959-973). LGP2 lacks the N-terminal CARD domains, but is implicated in the regulation of the innate immune response as a modulator of RIG-I and MDA5 activity (Bamming and Horvath, 2009, J Biol Chem 284: 9700-9712; Jiang et al., 2012, Immunity 36:959-973; Satoh et al., 2010, Proc Natl Acad Sci USA 107:1512-1517). RIG-I is normally found in the cytoplasm in an auto-repressed conformation, with the tandem CARDs partially occluded by an interaction with the Hel2i domain (Kowalinski et al., 2011, Cell 147:423-435). Binding to an RNA substrate produces a ternary complex competent for ATP binding and hydrolysis, exposing the CARD domains, although the precise role of ATP binding and hydrolysis in displacing the CARDs is still unclear. A comprehensive mutational analysis of RIG-I, MDA5, and LGP2 yielded several conventional Motif I-V mutants lacking catalytic activity, but found no correlation between ATP hydrolysis and IFN-β response (Bamming and Horvath, 2009, J Biol Chem 284:9700-9712). It has recently been proposed that ATP binding is required for signaling based on a RIG-I structural analysis (Luo et al., 2012b, Structure 20:1983-1988), and this is further supported by the observation that mutations in motif I, an ATP binding motif, disrupt RIG-I-dependent response (Bamming and Horvath, 2009, J Biol Chem 284:9700-9712).

Structural studies of mouse, human, and duck RIG-I truncations have enhanced the understanding of how RIG-I recognizes RNA and utilizes ATP (Civril et al., 2011, EMBO Rep 12:1127-1134; Jiang et al., 2011, Nature 479:423-427; Kowalinski et al., 2011, Cell 147:423-435; Luo et al., 2011, Cell 147:409-422). Unfortunately, in the only RIG-I structure with the CARD domains present, the protein is in an inactive, apo-state, and lacks the CTD. This leaves several important questions unanswered regarding the role of both RNA and ATP in RIG-I's innate immune response, and the relative positions of the CTD and CARDs in the active RIG-I conformation. Intriguingly, in all of the RIG-I:RNA complex structures, the RIG-I CTD caps the 5' end of the RNA, regardless of the length of the bound duplex. RIG-I's preference for the end of the duplex RNA in these structures is also independent of a 5'triphosphate. Furthermore, the RIG-I helicase domain exhibits a weak affinity for both 5'OH and 5'ppp duplex RNA, with a $K_D$ in the micromolar range (Jiang et al., 2011, Nature 479:423-427; Vela et al., 2012, J Biol Chem 287:42564-42573), suggesting that internal duplex stem binding may play a lesser role in RIG-I stimulation.

Several studies have reported the RNA-induced multimerization of RIG-I using a variety of techniques, including size exclusion chromatography, atomic force microscopy (AFM), and electrophoretic mobility shift assay (EMSA) experiments (Beckham et al., 2013, Nucleic Acids Res. 2013 Jan. 15; Binder et al., 2011, J Biol Chem 286(31):27278-87; Feng et al., 2012, Protein Cell. 2012 Dec. 20; Schmidt et al., 2009, Proc Natl Acad Sci USA 106:12067-12072). This oligomerization might occur via interactions between two or more RIG-I molecules bound to the same RNA substrate, or through protein-protein interactions between independent ternary complexes subsequent to RNA stimulation, or conceivably through some combination of these two scenarios. An IRF3 dimerization assay reconstituted in vitro demonstrated that poly-ubiquitin chains induce the formation of a RIG-I tetramer composed of four RIG-I:RNA units and four poly-ubiquitin chains (Jiang et al., 2012, Immunity 36:959-973). Whereas MDA5 forms long cooperative filaments on RNA with distinct protein-protein contacts required for activation and consequently prefers longer RNA substrates than RIG-I (Berke and Modis, 2012, EMBO J 31:1714-1726; Berke et al., 2012, Proc Natl Acad Sci USA 109: 18437-18441; Jiang et al., 2012, Immunity 36:959-973; Peisley et al., 2011, Proc Natl Acad Sci USA 108: 21010-21015), the oligomerization state required for RIG-I activation and RIG-I's preference for smaller substrates is not well understood (Kolakofsky et al., 2012, RNA 18:2118-2127).

There still remains a need in the art for compositions and method to study the role of RIG-I and means of regulating RIG-I. The present invention satisfies this need in the art.

SUMMARY OF THE INVENTION

The present invention provides a composition comprising a nucleic acid capable of inducing interferon production. The molecule comprises a double-stranded section of less than 19 base pairs and at least one blunt end. In one embodiment, the nucleic acid molecule comprises a single strand nucleic acid molecule which forms a hairpin structure comprising the double-stranded section and a loop. In one embodiment, the nucleic acid molecule comprises a double-stranded nucleic acid molecule and two blunt ends. In one embodiment, the nucleic acid molecule comprises at least one of the group consisting of a 5' triphosphate and a 5' diphosphate. In one embodiment, the molecule is capable of entering the nucleus.

In one embodiment, the molecule comprises a modified phosphodiester backbone. In one embodiment, the molecule comprises at least one 2'-modified nucleotide. In one embodiment, the 2'-modified nucleotide comprises a modification selected from the group consisting of: 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), and 2'-O—N-methylacetamido (2'-O-NMA). In one embodiment, the molecule comprises at least one modified phosphate group. In one embodiment, the molecule comprises at least one modified base. In one embodiment, the double-stranded section comprises one or more mispaired bases.

The present invention provides a method for inducing type I interferon production in a cell. The method comprises contacting the cell with a nucleic acid molecule, wherein the molecule comprises a double-stranded section of less than 19 base pairs and at least one blunt end. In one embodiment, the nucleic acid molecule comprises a single strand nucleic acid molecule which forms a hairpin structure comprising the double-stranded section and a loop. In one embodiment, the nucleic acid molecule comprises a double-stranded nucleic acid molecule and two blunt ends. In one embodiment, the nucleic acid molecule comprises at least one of the group consisting of a 5' triphosphate and a 5' diphosphate. In one embodiment, the molecule is capable of entering the nucleus.

In one embodiment, the molecule comprises a modified phosphodiester backbone. In one embodiment, the molecule comprises at least one 2'-modified nucleotide. In one embodiment, the 2'-modified nucleotide comprises a modification selected from the group consisting of: 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), and 2'-O—N-methylacetamido (2'-O-NMA). In one embodiment, the molecule comprises at least one modified phosphate group. In one embodiment, the molecule comprises at least one modified base. In one embodiment, the double-stranded section comprises one or more mispaired bases.

The present invention provides a method for treating a disease or disorder in a subject in need thereof by inducing type I interferon production in a cell of the subject. The method comprises contacting the cell with a nucleic acid molecule, wherein the molecule comprises a double-stranded section of less than 19 base pairs and at least one blunt end. In one embodiment, the nucleic acid molecule comprises a single strand nucleic acid molecule which forms a hairpin structure comprising the double-stranded section and a loop. In one embodiment, the nucleic acid molecule comprises a double-stranded nucleic acid molecule and two blunt ends. In one embodiment, the nucleic acid molecule comprises at least one of the group consisting of a 5' triphosphate and a 5' diphosphate. In one embodiment, the molecule is capable of entering the nucleus.

In one embodiment, the molecule comprises a modified phosphodiester backbone. In one embodiment, the molecule comprises at least one 2'-modified nucleotide. In one embodiment, the 2'-modified nucleotide comprises a modification selected from the group consisting of: 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), and 2'-O—N-methylacetamido (2'-O-NMA). In one embodiment, the molecule comprises at least one modified phosphate group. In one embodiment, the molecule comprises at least one modified base. In one embodiment, the double-stranded section comprises one or more mispaired bases.

In one embodiment, the disease or disorder is selected from the group consisting of a bacterial infection, a viral infection, a parasitic infection, cancer, an autoimmune disease, an inflammatory disorder, and a respiratory disorder.

The present invention provides a pharmaceutical composition comprising a nucleic acid molecule capable of inducing interferon production and a pharmaceutically acceptable carrier, wherein the molecule comprises a double-stranded section of less than 19 base pairs and at least one blunt end. In one embodiment, the nucleic acid molecule comprises a single strand nucleic acid molecule which forms a hairpin structure comprising the double-stranded section and a loop. In one embodiment, the nucleic acid molecule comprises a double-stranded nucleic acid molecule and two blunt ends. In one embodiment, the nucleic acid molecule comprises at least one of the group consisting of a 5' triphosphate and a 5' diphosphate. In one embodiment, the pharmaceutical composition further comprises at least one agent selected from an immunostimulatory agent, an antigen, an anti-viral agent, an anti-bacterial agent, an anti-tumor agent, retinoic acid, IFN-α, and IFN-β.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 1, comprising FIG. 1 through FIG. 1E, depicts the results of structural analysis demonstrating that the HEL2i domain scans along the duplex RNA backbone. Three distinct conformations of RIG-I (ΔCARDs: 1-229):GC10 with an empty ATP-binding pocket (pdb:3zd6), and in complex with a $SO_4^{2-}$ (pdb:2ykg) and ADP-$Mg^{2+}$ (pdb:3zd7). GC10 is a palindromic RNA duplex of repeating 'GC' with a 5'hydroxyl. FIG. 1E is a diagram of the RIG-I:RNA duplex interface. The closest distances between the RNA and the residues K508 and Q511 from the HEL2i domain are highlighted and shown as dashed lines. CARDs, caspase activation and recruitment domains; RIG-I, retinoic acid-inducible gene-I.

FIG. 3A through FIG. 3D, depicts the results of experiments demonstrating that RIG-I is stimulated by the ends of poly I:C. (FIG. 3A) LMW poly I:C was fractionated on an analytical Superdex 200 size exclusion chromatography column and separated into seven fractions on a 15% polyacrylamide, 4M urea semi-denaturing gel stained with ethidium bromide (marker is in base pairs). (FIG. 3B) ATPase activity of RIG-I stimulated by 0-15 ng/μl of the poly I:C fractions A1, A3, A5 and A7 at 5 mM ATP. The data were fit to the quadratic form of the Briggs-Haldane equation with the assumption that the $k_m$ values are the same for all the fractions. (FIG. 3C) The $K_{m,ATP}$ for RIG-I stimulated by 15 ng/μl of the poly I:C fractions A1-A7 while varying the ATP concentration from 0-5 mM ATP. (FIG. 3D) The calculated $K_{m,RNA}$ for RIG-I stimulated by 0-15 ng/μl of the poly I:C fractions A1-A7 at 5 mM ATP. The $K_m$ values in the left panel are in ng/μl and values in the right panel are in nM for all seven fractions on the basis of the estimated sizes of each fraction. Error bars for the poly I:C data report the standard deviation across six experiments. LMW, low molecular weight; RIG-I, retinoic acid-inducible gene-I.

FIG. 4, comprising (FIG. 4A) The $K_{m,ATP}$ of RIG-I stimulated by a library of duplex RNA constructs at ATP concentrations varying between 0 and 5 mM. (FIG. 4B) The $K_{m,RNA}$ of RIG-I stimulated by a library of duplex RNA constructs at RNA concentrations varying between 0 and 500 nM. The $K_{m,RNA}$ for the GC8 duplex is ~100 nM and did not fit on the scale. (FIG. 4C) The $k_{cat}$ summary averaged from the $K_{m,ATP}$ and $K_{m,RNA}$ experiments. (FIG. 4D) RIG-I stimulated IFN-β production was measured in 293T cells. RIG-I was stimulated by 5'triphosphorylated hairpins (20-650 nM) and the positive controls, poly I:C (15-500 ng/well) and 5'pppGC22 (20-650 nM). The increase in RNA concentration is indicated by a darkening color gradient. The relative luciferase is the firefly luciferase (IFN-β reporter) divided by the constitutively expressed Renilla luciferase. Error bars for the ATPase data report the standard deviation from at least three measurements. Error bars for the cell culture data report the standard error of the mean from three measurements. IFN-β, interferon-β; RIG-I, retinoic acid-inducible gene-I. The constructs and nucleic acid sequences of the constructs used are listed in Table 2.

FIG. 6A and FIG. 6B, depicts the results of $K_{m,ATP}$ and $K_{m,RNA}$ ATPase experiments on LMW poly I:C. FIG. 6A depicts the ATPase activity of RIG-I stimulated by 500 ng/μL LMW poly I:C while varying the ATP concentration from 0 to 5 mM ATP. Error bars report the standard deviation from 4 experiments. FIG. 6B depicts the ATPase activity of RIG-I at 5 mM ATP while varying LMW poly I:C from 0 to 500 ng/µL. Error bars report the standard deviation from 4 experiments. The average kcat from both experiments was 4.9 s$^{-1}$, and the $K_{m,ATP}$ was approximately 700 µM. The $K_{m,RNA}$ was 2.4 ng/µL, which is difficult to interpret because it cannot be expressed as a nanomolar value due to the heterogeneity of poly I:C samples FIG. 7, comprising (FIG. 7A) ATPase measurements on 4 triphosphorylated hairpins with a duplex region of 8, 10, 20, and 30 nucleotides with a UUCG hairpin. (FIG. 7B) ATPase measurements on 6 double stranded RNA duplexes with 5'hydroxyl of length 8, 10, 12, 14, 18, and 22. (FIG. 7C) ATPase measurements on 4 double stranded RNA duplexes with a 5'triphosphate of length 10, 12, and 22. Table 2 lists the RNA sequences used in this study. Similar kcat values were observed for RIG-I stimulated by the 5'ppp8L hairpin and GC8. However, in the case of the hairpin, a 5.2 nM $K_{m,RNA}$ was observed, approximately 20-fold smaller than GC8, perhaps because 5'ppp8L contains a 'UUCG' tetraloop, which may accommodate the HEL2i flexibility seen in the crystal structures.

FIGS. 10A through 10C, is a series of images showing ATPase activity of 5, 10, 25, and 50 nM RIG-I stimulated by hairpin and duplex RNA at ATP concentrations ranging from 0 to 5 mM. Measurements are reported as ATP molecules hydrolyzed per second. FIG. 10A demonstrates the results of varying concentrations of RIG-I stimulated by 1 µM of 5'ppp10L. Error bars report SEM from 4 experiments at each ATP concentration. FIG. 10B shows the results of varying concentrations of RIG-I stimulated by 1 µM of 5'pppGC22. Error bars report SEM from 4 experiments at each ATP concentration. FIG. 10C is a graph showing the kcat values from the fit to the hyperbolic form of the Briggs-Haldane equation are plotted at each enzyme concentration for 5'ppp10L and 5'pppGC22. Error bars report the standard error from the fit.

Figures 1A, 1B, 1C, 1D:
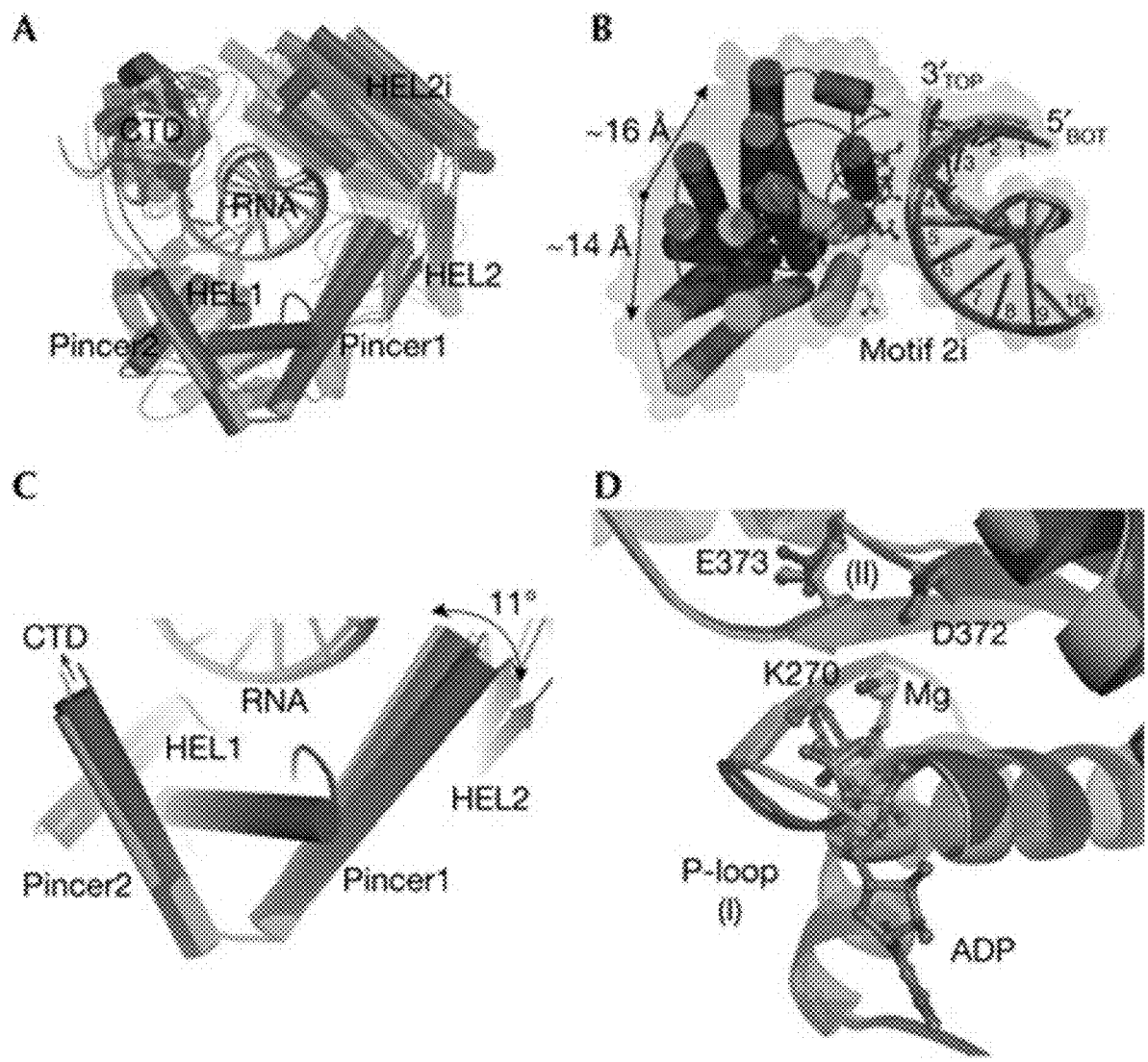
FIG. 1A depicts the alignment of the three conformations.
FIG. 1B depicts the interface between the HEL2i and the duplex RNA. Key residues in the HEL2i domain, Q511 and K508, are involved in RNA binding and are shown as sticks. Using residue E530 as the reference, there is a 14 Å movement of the HEL2i domain between conformations 1 and 2, and a 16 Å movement between conformations 2 and 3.
FIG. 1C is a close-up view of the pincer domain, highlighting the motions of pincer1 (the first α-helix). The change in the angle between pincer1 and pincer2 (the second α-helix) is 11°.
FIG. 1D depicts the ATP-binding pocket of the superimposed structures. Ligands ($SO_4^{2-}$ and ADP-$Mg^{2+}$) and the key residues (K270 from motif I; D372 and E373 from motif II) are shown as sticks.

Both transcribed and synthesized 5'ppp10L induce IFN to a similar degree, although the synthetic triphosphorylated RNA is slightly more active. Extra enzyme treatment and purification of transcribed 5'ppp10L does not impact IFN levels.

DETAILED DESCRIPTION

The present invention provides a nucleic acid molecule that can activate the interferon response of one or more pattern recognition receptors (PRRs). The invention is based on the identification of a minimal RNA substrate to which RIG-I binds whereby the substrate stimulates the ATPase activity by RIG-I and elicits an interferon response in vivo. Accordingly, the invention provides compositions and methods for inducing the interferon response of one or more PRRs. For example, the compositions and methods described herein may activate any PRR including, but not limited to, the RIG-I like receptor (RLR) class of PRRs, which include RIG-I, MDA5, and LGP2; NOD-like receptors (NLRs), C-type lectin receptors (CLRs), and toll-like receptors (TLRs). In one embodiment, the invention provides a nucleic acid molecule. Exemplary nucleic acids for use in this disclosure include ribonucleic acids (RNA), deoxyribonucleic acids (DNAs), peptide nucleic acids (PNAs), threose nucleic acids (TNAs), glycol nucleic acids (GNAs), locked nucleic acids (LNAs) or a hybrid thereof. As described herein, the nucleic acid molecule of the invention is not dependent on a particular nucleotide sequence. Rather, any nucleotide sequence may be used, provided that the sequence has the ability to form the structure of a nucleic acid molecule described herein.

In one embodiment, the nucleic acid molecule of the invention comprises a double stranded region. For example, in one embodiment, the nucleic acid molecule is a double stranded duplex. In one embodiment, the nucleic acid molecule of the invention is a single strand wherein a first region of the molecule hybridizes with a second region of the molecule to form a duplex. In certain instances, the hairpin structure of the nucleic acid molecule may improve the stability of the duplex.

In one embodiment, the nucleic acid molecule comprises a blunt end. In one embodiment, the nucleic acid molecule comprises a 5' triphosphate or a 5' diphosphate. In certain instances, the presence of one or more 5' triphosphate or 5' diphosphate may improve the binding affinity of the nucleic acid molecule.

In one embodiment, the invention provides a nucleic acid molecule which is capable of activating a PRR and inducing an IFN response in cells expressing a PRR. In one embodiment, the nucleic acid molecule of the present invention has a double-stranded section of less than 19 base pairs. In one embodiment, the nucleic acid molecule comprises at least one 5' triphosphate or at least one 5' diphosphate. In one embodiment, the nucleic acid molecule comprises at least one blunt end.

The present invention encompasses the use of the nucleic acid molecule to prevent and/or treat any disease, disorder, or condition in which inducing IFN production would be beneficial. For example, increased IFN production, by way of the nucleic acid molecule of the invention, may be beneficial to prevent or treat a wide variety of disorders, including, but not limited to, bacterial infection, viral infection, parasitic infection, cancer, autoimmune diseases, respiratory disorders, and the like.

In one embodiment, the invention provides a composition and method for the prevention and/or treatment of a viral infection, including, but not limited to, influenza, hepatitis, human papillomavirus, HIV, and the like. In one embodiment, the invention provides a composition and method for the treatment of a cancer, including, but not limited to, hematological malignancies including various leukemias and lymphomas, carcinomas, blastomas, and sarcomas. In one embodiment, the invention provides a composition and method for the treatment of an autoimmune disease, including but not limited to multiple sclerosis, psoriasis, arthritis, dermatitis, diabetes, lupus, colitis, Aicardi-Goutieres syndrome (AGS), and the like.

In one embodiment, the invention provides a composition and method for preventing and/or treating a respiratory disorder, including, acute lung injury (ALI), acute respiratory distress syndrome (ARDS), asthma, chronic obstructive pulmonary disease (COPD), obstructive sleep apnea (OSA), idiopathic pulmonary fibrosis (IPF), tuberculosis, pulmonary hypertension, pleural effusion, and lung cancer.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

The term "airway inflammation", as used herein, means a disease or condition related to inflammation on airway of subject. The airway inflammation may be caused or accompanied by allergy(ies), asthma, impeded respiration, cystic fibrosis (CF), chronic obstructive pulmonary diseases (COPD), allergic rhinitis (AR), acute respiratory distress syndrome (ARDS), microbial or viral infections, pulmonary hypertension, lung inflammation, bronchitis, cancer, airway obstruction, bronchoconstriction, and the like.

The term "autoimmune disease" as used herein is defined as a disorder that results from an autoimmune response. An autoimmune disease is the result of an inappropriate and excessive response to a self-antigen. Examples of autoimmune diseases include but are not limited to, Addison's disease, alopecia greata, ankylosing spondylitis, autoimmune hepatitis, autoimmune parotitis, Crohn's disease, diabetes (Type I), dystrophic epidermolysis bullosa, epididymitis, glomerulonephritis, Graves' disease, Guillain-Barr syndrome, Hashimoto's disease, hemolytic anemia, systemic lupus erythematosus, multiple sclerosis, myasthenia gravis, pemphigus vulgaris, psoriasis, rheumatic fever, rheumatoid arthritis, sarcoidosis, scleroderma, Sjogren's syndrome, spondyloarthropathies, thyroiditis, vasculitis, vitiligo, myxedema, pernicious anemia, ulcerative colitis, among others.

The term "cancer" as used herein is defined as disease characterized by the rapid and uncontrolled growth of aberrant cells. Cancer cells can spread locally or through the bloodstream and lymphatic system to other parts of the body.

Examples of various cancers include but are not limited to, breast cancer, prostate cancer, ovarian cancer, cervical cancer, skin cancer, pancreatic cancer, colorectal cancer, renal cancer, liver cancer, brain cancer, lymphoma, leukemia, lung cancer and the like.

The term "chronic obstructive pulmonary disease," or COPD, is used herein to refer to two lung diseases, chronic bronchitis and emphysema, that are characterized by obstruction to airflow that interferes with normal breathing. Both of these conditions frequently co-exist.

"Complementary" refers to the broad concept of sequence complementarity between regions of two nucleic acid strands or between two regions of the same nucleic acid strand. It is known that an adenine residue of a first nucleic acid region is capable of forming specific hydrogen bonds ("base pairing") with a residue of a second nucleic acid region which is antiparallel to the first region if the residue is thymine or uracil. Similarly, it is known that a cytosine residue of a first nucleic acid strand is capable of base pairing with a residue of a second nucleic acid strand which is antiparallel to the first strand if the residue is guanine A first region of a nucleic acid is complementary to a second region of the same or a different nucleic acid if, when the two regions are arranged in an antiparallel fashion, at least one nucleotide residue of the first region is capable of base pairing with a residue of the second region. Preferably, the first region comprises a first portion and the second region comprises a second portion, whereby, when the first and second portions are arranged in an antiparallel fashion, at least about 50%, and preferably at least about 75%, at least about 90%, or at least about 95% of the nucleotide residues of the first portion are capable of base pairing with nucleotide residues in the second portion. More preferably, all nucleotide residues of the first portion are capable of base pairing with nucleotide residues in the second portion.

The term "emphysema" is a major subset of the clinical entity known as COPD and is characterized by specific pathological changes in lung tissue over time. One hallmark of emphysema is the gradual, progressive, and irreversible destruction of the distal lung parenchyma leading to the destruction alveoli. Alveolar destruction leads to enlarged airspaces in the lung and consequently a reduced ability to transfer oxygen to the bloodstream. Emphysema is also characterized by a loss of elasticity in the lung making it difficult to maintain open airways. Both of these changes produce the clinical sequelae of emphysema comprising shortness of breath and difficulty exhaling, respectively.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA. Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

As used herein, the term "fragment," as applied to a nucleic acid, refers to a subsequence of a larger nucleic acid. A "fragment" of a nucleic acid can be at least about 5 nucleotides in length; for example, at least about 10 nucleotides to about 100 nucleotides; at least about 100 to about 500 nucleotides, at least about 500 to about 1000 nucleotides, at least about 1000 nucleotides to about 1500 nucleotides; or about 1500 nucleotides to about 2500 nucleotides; or about 2500 nucleotides (and any integer value in between).

"Homologous, homology" or "identical, identity" as used herein, refer to comparisons among amino acid and nucleic acid sequences. When referring to nucleic acid molecules, "homology," "identity," or "percent identical" refers to the percent of the nucleotides of the subject nucleic acid sequence that have been matched to identical nucleotides by a sequence analysis program. Homology can be readily calculated by known methods. Nucleic acid sequences and amino acid sequences can be compared using computer programs that align the similar sequences of the nucleic or amino acids and thus define the differences. In preferred methodologies, the BLAST programs (NCBI) and parameters used therein are employed, and the ExPaSy is used to align sequence fragments of genomic DNA sequences. However, equivalent alignment assessments can be obtained through the use of any standard alignment software.

As used herein, "homologous" refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same subunit, e.g., if a position in each of two DNA molecules is occupied by adenine, then they are homologous at that position. The homology between two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90% homology. By way of example, the DNA sequences 5'ATTGCC 3' and 5'TATGGC 3' share 50% homology. "Hybridization probes" are oligonucleotides capable of binding in a base-specific manner to a complementary strand of nucleic acid. Such probes include peptide nucleic acids, as described in Nielsen et al., 1991, Science 254, 1497-1500, and other nucleic acid analogs and nucleic acid mimetics. See U.S. Pat. No. 6,156,501.

The term "hybridization" refers to the process in which two single-stranded nucleic acids bind non-covalently to form a double-stranded nucleic acid; triple-stranded hybridization is also theoretically possible. Complementary sequences in the nucleic acids pair with each other to form a double helix. The resulting double-stranded nucleic acid is a "hybrid." Hybridization may be between, for example, two complementary or partially complementary sequences. The hybrid may have double-stranded regions and single stranded regions. The hybrid may be, for example, DNA:DNA, RNA:DNA or DNA:RNA. Hybrids may also be formed between modified nucleic acids. One or both of the nucleic acids may be immobilized on a solid support. Hybridization techniques may be used to detect and isolate specific sequences, measure homology, or define other characteristics of one or both strands.

The stability of a hybrid depends on a variety of factors including the length of complementarity, the presence of mismatches within the complementary region, the temperature and the concentration of salt in the reaction. Hybridizations are usually performed under stringent conditions, for example, at a salt concentration of no more than 1 M and a temperature of at least 25° C. For example, conditions of 5×SSPE (750 mM NaCl, 50 mM Na Phosphate, 5 mM EDTA, pH 7.4) or 100 mM MES, 1 M Na, 20 mM EDTA, 0.01% Tween-20 and a temperature of 25-50° C. are suitable for allele-specific probe hybridizations. In a particularly preferred embodiment, hybridizations are performed at 40-50° C. Acetylated BSA and herring sperm DNA may be added to hybridization reactions. Hybridization conditions suitable for microarrays are described in the Gene Expression Technical Manual and the GeneChip Mapping Assay Manual available from Affymetrix (Santa Clara, Calif.).

A first oligonucleotide anneals with a second oligonucleotide with "high stringency" if the two oligonucleotides anneal under conditions whereby only oligonucleotides which are at least about 75%, and preferably at least about 90% or at least about 95%, complementary anneal with one another. The stringency of conditions used to anneal two oligonucleotides is a function of, among other factors, temperature, ionic strength of the annealing medium, the incubation period, the length of the oligonucleotides, the G-C content of the oligonucleotides, and the expected degree of non-homology between the two oligonucleotides, if known. Methods of adjusting the stringency of annealing conditions are known (see, e.g. Sambrook et al., 2012, Molecular Cloning: A Laboratory Manual, Cold Spring Harbor Laboratory Press, Cold Spring Harbor, N.Y.).

As used herein, an "instructional material" includes a publication, a recording, a diagram, or any other medium of expression which can be used to communicate the usefulness of a compound, composition, vector, or delivery system of the invention in the kit for effecting alleviation of the various diseases or disorders recited herein. Optionally, or alternately, the instructional material can describe one or more methods of alleviating the diseases or disorders in a cell or a tissue of a mammal. The instructional material of the kit of the invention can, for example, be affixed to a container which contains the identified compound, composition, vector, or delivery system of the invention or be shipped together with a container which contains the identified compound, composition, vector, or delivery system. Alternatively, the instructional material can be shipped separately from the container with the intention that the instructional material and the compound be used cooperatively by the recipient.

As used herein, "isolate" refers to a nucleic acid obtained from an individual, or from a sample obtained from an individual. The nucleic acid may be analyzed at any time after it is obtained (e.g., before or after laboratory culture, before or after amplification.)

The term "label" as used herein refers to a luminescent label, a light scattering label or a radioactive label. Fluorescent labels include, but are not limited to, the commercially available fluorescein phosphoramidites such as Fluoreprime (Pharmacia), Fluoredite (Millipore) and FAM (ABI). See U.S. Pat. No. 6,287,778.

The term "mismatch," "mismatch control" or "mismatch probe" refers to a nucleic acid whose sequence is not perfectly complementary to a particular target sequence. The mismatch may comprise one or more bases. As used herein, the term "nucleic acid" refers to both naturally-occurring molecules such as DNA and RNA, but also various derivatives and analogs. Generally, the probes, hairpin linkers, and target polynucleotides of the present teachings are nucleic acids, and typically comprise DNA. Additional derivatives and analogs can be employed as will be appreciated by one having ordinary skill in the art.

The term "nucleotide base," as used herein, refers to a substituted or unsubstituted aromatic ring or rings. In certain embodiments, the aromatic ring or rings contain at least one nitrogen atom. In certain embodiments, the nucleotide base is capable of forming Watson-Crick and/or Hoogsteen hydrogen bonds with an appropriately complementary nucleotide base. Exemplary nucleotide bases and analogs thereof include, but are not limited to, naturally occurring nucleotide bases adenine, guanine, cytosine, 6 methyl-cytosine, uracil, thymine, and analogs of the naturally occurring nucleotide bases, e.g., 7-deazaadenine, 7-deazaguanine, 7-deaza-8-azaguanine, 7-deaza-8-azaadenine, N6 delta 2-isopentenyladenine (6iA), N6-delta 2-isopentenyl-2-methylthioadenine (2 ms6iA), N2-dimethylguanine (dmG), 7methylguanine (7mG), inosine, nebularine, 2-aminopurine, 2-amino-6-chloropurine, 2,6-diaminopurine, hypoxanthine, pseudouridine, pseudocytosine, pseudoisocytosine, 5-propynylcytosine, isocytosine, isoguanine, 7-deazaguanine, 2-thiopyrimidine, 6-thioguanine, 4-thiothymine, 4-thiouracil, 06-methylguanine, N6-methyladenine, 04-methylthymine, 5,6-dihydrothymine, 5,6-dihydrouracil, pyrazolo[3,4-D]pyrimidines (see, e.g., U.S. Pat. Nos. 6,143,877 and 6,127,121 and PCT published application WO 01/38584), ethenoadenine, indoles such as nitroindole and 4-methylindole, and pyrroles such as nitropyrrole. Certain exemplary nucleotide bases can be found, e.g., in Fasman, 1989, Practical Handbook of Biochemistry and Molecular Biology, pp. 385-394, CRC Press, Boca Raton, Fla., and the references cited therein.

The term "nucleotide," as used herein, refers to a compound comprising a nucleotide base linked to the C-1' carbon of a sugar, such as ribose, arabinose, xylose, and pyranose, and sugar analogs thereof. The term nucleotide also encompasses nucleotide analogs. The sugar may be substituted or unsubstituted. Substituted ribose sugars include, but are not limited to, those riboses in which one or more of the carbon atoms, for example the 2'-carbon atom, is substituted with one or more of the same or different Cl, F, —R, —OR, —NR2 or halogen groups, where each R is independently H, C1-C6 alkyl or C5-C14 aryl. Exemplary riboses include, but are not limited to, 2'-(C1-C6)alkoxyribose, 2'-(C5-C14)aryloxyribose, 2',3'-didehydroribose, 2'-deoxy-3'-haloribose, 2'-deoxy-3'-fluororibose, 2'-deoxy-3'-chlororibose, 2'-deoxy-3'-aminoribose, 2'-deoxy-3'-(C1-C6)alkylribose, 2'-deoxy-3'-(C1-C6)alkoxyribose and 2'-deoxy-3'-(C5-C14)aryloxyribose, ribose, 2'-deoxyribose, 2',3'-dideoxyribose, 2'-haloribose, 2'-fluororibose, 2'-chlororibose, and 2'-alkylribose, e.g., 2'-O-methyl, 4'-anomeric nucleotides, 1'-anomeric nucleotides, 2'-4'- and 3'-4'-linked and other "locked" or "LNA", bicyclic sugar modifications (see, e.g., PCT published application nos. WO 98/22489, WO 98/39352; and WO 99/14226). The term "nucleic acid" typically refers to large polynucleotides.

The term "oligonucleotide" typically refers to short polynucleotides, generally, no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

The term "overhang," as used herein, refers to terminal non-base pairing nucleotide(s) resulting from one strand or region extending beyond the terminus of the complementary strand to which the first strand or region forms a duplex. One or more polynucleotides that are capable of forming a duplex through hydrogen bonding can have overhangs. The single-stranded region extending beyond the 3' end of the duplex is referred to as an overhang.

The term "pattern recognition receptor," abbreviated as PRR, as used herein refers to a family of proteins that typically recognize pathogen-associated molecular patterns. PRRs may include members of the RIG-I like receptor (RLR) family, NOD-like receptor (NLRs) family, C-type lectin receptor (CLRs) family, or toll-like receptor (TLRs) family. In one embodiment of the present invention, the nucleic acid molecule described herein binds to a PRR, thereby resulting in an interferon response. It should be understood that a PRR includes any PRR fragment, variant, splice variant, mutant, or the like. In certain embodiments, the PRR is RIG-I.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning and amplification technology, and the like, and by synthetic means. An "oligonucleotide" as used herein refers to a short polynucleotide, typically less than 100 bases in length.

Conventional notation is used herein to describe polynucleotide sequences: the left-hand end of a single-stranded polynucleotide sequence is the 5'-end. The DNA strand having the same sequence as an mRNA is referred to as the "coding strand"; sequences on the DNA strand which are located 5' to a reference point on the DNA are referred to as "upstream sequences"; sequences on the DNA strand which are 3' to a reference point on the DNA are referred to as "downstream sequences." In the sequences described herein:

A=adenine,
G=guanine,
T=thymine,
C=cytosine,
U=uracil,
H=A, C or T/U,
R=A or G,
M=A or C,
K=G or T/U,
S=G or C,
Y=C or T/U,
W=A or T/U,
B=G or C or T/U,
D=A or G, or T/U,
V=A or G or C,
N=A or G or C or T/U.

The skilled artisan will understand that all nucleic acid sequences set forth herein throughout in their forward orientation, are also useful in the compositions and methods of the invention in their reverse orientation, as well as in their forward and reverse complementary orientation, and are described herein as well as if they were explicitly set forth herein.

"Primer" refers to a polynucleotide that is capable of specifically hybridizing to a designated polynucleotide template and providing a point of initiation for synthesis of a complementary polynucleotide. Such synthesis occurs when the polynucleotide primer is placed under conditions in which synthesis is induced, e.g., in the presence of nucleotides, a complementary polynucleotide template, and an agent for polymerization such as DNA polymerase. A primer is typically single-stranded, but may be double-stranded. Primers are typically deoxyribonucleic acids, but a wide variety of synthetic and naturally occurring primers are useful for many applications. A primer is complementary to the template to which it is designed to hybridize to serve as a site for the initiation of synthesis, but need not reflect the exact sequence of the template. In such a case, specific hybridization of the primer to the template depends on the stringency of the hybridization conditions. Primers can be labeled with a detectable label, e.g., chromogenic, radioactive, or fluorescent moieties and used as detectable moieties. Examples of fluorescent moieties include, but are not limited to, rare earth chelates (europium chelates), Texas Red, rhodamine, fluorescein, dansyl, phycocrytherin, phycocyanin, spectrum orange, spectrum green, and/or derivatives of any one or more of the above. Other detectable moieties include digoxigenin and biotin.

As used herein a "probe" is defined as a nucleic acid capable of binding to a target nucleic acid of complementary sequence through one or more types of chemical bonds, usually through complementary base pairing, usually through hydrogen bond formation. As used herein, a probe may include natural (i.e. A, G, U, C, or T) or modified bases (7-deazaguanosine, inosine, etc.). In addition, a linkage other than a phosphodiester bond may join the bases in probes, so long as it does not interfere with hybridization. Thus, probes may be peptide nucleic acids in which the constituent bases are joined by peptide bonds rather than phosphodiester linkages. The term "match," "perfect match," "perfect match probe" or "perfect match control" refers to a nucleic acid that has a sequence that is perfectly complementary to a particular target sequence. The nucleic acid is typically perfectly complementary to a portion (subsequence) of the target sequence. A perfect match (PM) probe can be a "test probe", a "normalization control" probe, an expression level control probe and the like. A perfect match control or perfect match is, however, distinguished from a "mismatch" or "mismatch probe."

The term "respiratory diseases", as used herein, means diseases or conditions related to, the respiratory system. Examples include, but not limited to, asthma, chronic obstructive pulmonary disease (COPD), airway inflammation, allergy(ies), impeded respiration, cystic fibrosis (CF), allergic rhinitis (AR), acute respiratory distress syndrome (ARDS), lung cancer, pulmonary hypertension, lung inflammation, bronchitis, airway obstruction, bronchoconstriction, microbial infection, and viral infection, such as SARS. Other respiratory diseases referred to herein include dyspnea, emphysema, wheezing, pulmonary fibrosis, hyper-responsive airways, increased adenosine or adenosine receptor levels, particularly those associated with infectious diseases, surfactant depletion, pulmonary vasoconstriction, impeded respiration, infantile respiratory distress syndrome (infantile RDS), allergic rhinitis, and the like.

The term "ribonucleotide" and the phrase "ribonucleic acid" (RNA), as used herein, refer to a modified or unmodified nucleotide or polynucleotide comprising at least one ribonucleotide unit. A ribonucleotide unit comprises an oxygen attached to the 2' position of a ribosyl moiety having a nitrogenous base attached in N-glycosidic linkage at the 1' position of a ribosyl moiety, and a moiety that either allows for linkage to another nucleotide or precludes linkage.

The term "target" as used herein refers to a molecule that has an affinity for a given molecule. Targets may be naturally-occurring or man-made molecules. Also, they can be employed in their unaltered state or as aggregates with other species. Targets may be attached, covalently or noncovalently, to a binding member, either directly or via a specific binding substance. Examples of targets which can be employed by this invention include, but are not restricted to, proteins, peptides, oligonucleotides and nucleic acids.

"Variant" as the term is used herein, is a nucleic acid sequence or a peptide sequence that differs in sequence from a reference nucleic acid sequence or peptide sequence respectively, but retains essential properties of the reference molecule. Changes in the sequence of a nucleic acid variant may not alter the amino acid sequence of a peptide encoded by the reference nucleic acid, or may result in amino acid substitutions, additions, deletions, fusions and truncations. A variant of a nucleic acid or peptide can be a naturally occurring such as an allelic variant, or can be a variant that is not known to occur naturally. Non-naturally occurring variants of nucleic acids and peptides may be made by mutagenesis techniques or by direct synthesis.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

The present invention provides a nucleic acid molecule, for example a short duplex nucleic acid molecule, which is capable of activating one or more PRRs and inducing an IFN response in cells expressing a PRR. In one embodiment, the nucleic acid molecule of the present invention comprises a double-stranded section of no more than 19 base pairs, and at least one blunt end. In one embodiment, the nucleic acid molecule comprises a 5' triphosphate or a 5' diphosphate. In one embodiment, the invention further provides the use of the nucleic acid molecule of the invention for inducing an IFN response in vitro and in vivo. In one embodiment, the nucleic acid molecule of the invention binds to RIG-I, or other PRRs, which in turn leads to increased IFN production.

Accordingly, the present invention provides the use of the nucleic acid molecule of the invention for preventing and/or treating diseases or conditions in which inducing IFN production would be beneficial, such as infections, tumors/cancers, inflammatory diseases, and disorders, and immune disorders.

In one embodiment, the present invention provides the use of the nucleic acid molecule of the invention for assessing the level of expression, level of activity, or both of a PRR, or other members of the PRR pathway, in a cell. For example, in one embodiment, the invention provides a method of diagnosing a disease or disorder comprising using the nucleic acid molecule to assess the PRR-mediated IFN production in a cell. In one embodiment, the invention provides a screening assay for identifying a compound that alters PRR-mediated IFN response by using the nucleic acid molecule to assess PRR-mediated IFN response before, during, and/or after contact with a compound of interest.

In one embodiment, the nucleic acid of the invention comprises intramolecular nucleotide base pairing (i.e., hairpin). Therefore, in certain aspects, the nucleic acid molecule of the invention is sometimes referred herein as a short hairpin nucleic acid molecule.

The present invention encompasses compositions and method for inducing an interferon response produced by any PRR, including but not limited to members of the RIG-I like receptor (RLR) family; NOD-like receptor (NLRs) family, C-type lectin receptor (CLRs) family, and toll-like receptor (TLRs) family. Thus, while in certain instances, the present invention is exemplified herein through stimulation of RIG-I, a skilled artisan would recognize that the present invention is equally applicable to the stimulation of any PRR known in the art, or discovered in the future.

Compositions

In one embodiment, the invention provides a nucleic acid molecule which is capable of inducing an IFN response in cells expressing a PRR. In one embodiment, the nucleic acid molecule of the present invention comprises a double-stranded section of no more than 19 base pairs and at least one blunt end. In one embodiment, the nucleic acid molecule comprises a 5' triphosphate or a 5' diphosphate.

In one embodiment, the nucleic acid molecule of the present invention has a double-stranded section of less than 19 base pairs, in one aspect less than 18 base pairs, in one aspect less than 16 base pairs, in one aspect less than 14 base pairs, in one aspect less than 12 base pairs, in one aspect less than 10 base pairs, in one aspect less than 8 base pairs, in one aspect less than 6 base pairs, in one aspect less than 4 base pairs. In certain embodiments, the double-stranded section comprises one or more mispaired bases. That is, Watson-Crick base pairing is not required at each and every nucleotide pair. In one embodiment, the double-stranded section comprises about 4-19 base pairs.

In some instances, the nucleic acid molecule can be of any sequence and comprises a hairpin structure and a blunt end, wherein the hairpin comprises a double-stranded section of less than 19 base pairs.

The nucleic acid molecule of the invention comprises nucleic acids from any source. A nucleic acid in the context of the present invention includes but is not limited to deoxyribonucleic acid (DNA), ribonucleic acid (RNA), peptide nucleic acid (PNA, threose nucleic acid (TNA), glycol nucleic acid (GNA), locked nucleic acid (LNA) or a hybrid thereof). DNA and RNA are naturally occurring in organisms, however, they may also exist outside living organisms or may be added to organisms. The nucleic acid may be of any origin, e.g., viral, bacterial, archae-bacterial, fungal, ribosomal, eukaryotic or prokaryotic. It may be nucleic acid from any biological sample and any organism, tissue, cell or sub-cellular compartment. It may be nucleic acid from any organism. The nucleic acid may be pre-treated before quantification, e.g., by isolation, purification or modification. Also artificial or synthetic nucleic acid may be used. The length of the nucleic acids may vary. The nucleic acids may be modified, e.g. may comprise one or more modified nucleobases or modified sugar moieties (e.g., comprising methoxy groups). The backbone of the nucleic acid may comprise one or more peptide bonds as in peptide nucleic acid (PNA). The nucleic acid may comprise a base analog such as non-purine or non-pyrimidine analog or nucleotide analog. It may also comprise additional attachments such as proteins, peptides and/or or amino acids.

In one embodiment, the nucleic acid molecule of the invention is a single stranded oligonucleotide that forms an intramolecular structure, i.e., a hairpin structure.

In one embodiment, the hairpin nucleic acid molecule forms a blunt end. In one embodiment, a blunt end refers to refers to, e.g., an RNA duplex where at least one end of the duplex lacks any overhang, e.g., a 3' dinucleotide overhang, such that both the 5' and 3' strand end together, i.e., are flush or as referred to herein, are blunt. The molecules of the invention have at least one blunt end. In some instances, the intramolecular structure produces a 3' overhang. In some instances, the intramolecular structure produces a 5' overhang.

In certain instances, the short hairpin nucleic acid molecule of the invention is an ideal stimulant because of the ability to re-anneal after being unwound, whereas the shorter palindromic duplexes that are not a hairpin would likely lose their ability to stimulate IFN production as soon as the duplex melted. However, the present invention is not limited to hairpin structures, as it is demonstrated herein that short double-stranded duplexes demonstrate the ability to bind to a PRR and stimulate an interferon response.

In some instances, the short hairpin nucleic acid molecule of the invention is designed that in some conditions, the intramolecular stem structure has reduced stability where the stem structure is unfolded. In this manner, the stem structure can be designed so that the stem structure can be relieved of its intramolecular base pairing and resemble more of a linear molecule.

In accordance with the present invention, there are provided predetermined stem oligonucleotide sequences containing stretches of complementary sequences that form the stem structure. In one embodiment, the stem comprises a double-stranded section that comprise in one aspect less than 19 base pairs, in one aspect less than 18 base pairs, in one aspect less than 16 base pairs, in one aspect less than 14 base pairs, in one aspect less than 12 base pairs, in one aspect less than 10 base pairs, in one aspect less than 8 base pairs, in one aspect less than 6 base pairs, in one aspect less than 4 base pairs, such that these complementary stretches anneal to provide a hairpin structure. In one embodiment, the double-stranded section comprises one or more base mispairs. That is, the double-stranded section need not comprise Watson-Crick base pairing at each and every base pair in order to produce the hairpin structure.

In one embodiment, the short hairpin nucleic acid molecule of the invention comprising: an antisense sequence and a sense sequence, wherein the sense sequence is substantially complementary to the antisense sequence; and a loop region connecting the antisense and sense sequences.

In certain aspects, the present invention includes a polynucleotide comprising a unimolecular RNA, such as a short hairpin RNA. The short hairpin RNA can be a unimolecular RNA that includes a sense sequence, a loop region, and an antisense sequence which together form a hairpin loop structure. Preferably, the antisense and sense sequences are substantially complementary to one other (about 80% complementary or more), where in certain embodiments the antisense and sense sequences are 100% complementary to each other. In certain embodiments, antisense and sense sequences each comprises less than 19 nucleotides in length, e.g., between 18 and 8 nucleotides in length. Additionally, the antisense and sense sequences within a unimolecular RNA of the invention can be the same length or differ in length. The loop can be any length, for example a length being 0, 1 or more, 2 or more, 4 or more, 5 or more, 8 or more, 10 or more, 15 or more, 20 or more, 40 or more, or 100 or more nucleotides in length.

Nucleic Acid Modification

The nucleic acid molecules of the present invention can be modified to improve stability in serum or in growth medium for cell cultures. In order to enhance the stability, the 3'-residues may be stabilized against degradation, e.g., they may be selected such that they consist of purine nucleotides, particularly adenosine or guanosine nucleotides. Alternatively, substitution of pyrimidine nucleotides by modified analogues, e.g., substitution of uridine by 2'-deoxythymidine is tolerated and does not affect function of the molecule.

In one embodiment of the present invention the nucleic acid molecule may contain at least one modified nucleotide analogue. For example, the ends may be stabilized by incorporating modified nucleotide analogues.

Non-limiting examples of nucleotide analogues include sugar- and/or backbone-modified ribonucleotides (i.e., include modifications to the phosphate-sugar backbone). For example, the phosphodiester linkages of natural RNA may be modified to include at least one of a nitrogen or sulfur heteroatom. In preferred backbone-modified ribonucleotides the phosphoester group connecting to adjacent ribonucleotides is replaced by a modified group, e.g., of phosphothioate group. In preferred sugar-modified ribonucleotides, the 2' OH-group is replaced by a group selected from H, OR, R, halo, SH, SR, $NH_2$, NHR, $NR_2$ or ON, wherein R is $C_1$-$C_6$ alkyl, alkenyl or alkynyl and halo is F, Cl, Br or I.

Other examples of modifications are nucleobase-modified ribonucleotides, i.e., ribonucleotides, containing at least one non-naturally occurring nucleobase instead of a naturally occurring nucleobase. Bases may be modified to block the activity of adenosine deaminase. Exemplary modified nucleobases include, but are not limited to, uridine and/or cytidine modified at the 5-position, e.g., 5-(2-amino)propyl uridine, 5-bromo uridine; adenosine and/or guanosines modified at the 8 position, e.g., 8-bromo guanosine; deaza nucleotides, e.g., 7-deaza-adenosine; O- and N-alkylated nucleotides, e.g., N6-methyl adenosine are suitable. It should be noted that the above modifications may be combined.

Modifications can be added to enhance stability, functionality, and/or specificity and to minimize immunostimulatory properties of the short hairpin nucleic acid molecule of the invention. For example, the overhangs can be unmodified, or can contain one or more specificity or stabilizing modifications, such as a halogen or O-alkyl modification of the 2' position, or internucleotide modifications such as phosphorothioate modification. The overhangs can be ribonucleic acid, deoxyribonucleic acid, or a combination of ribonucleic acid and deoxyribonucleic acid.

In some instances, the nucleic acid molecule comprises at least one of the following chemical modifications: 2'-H, 2'-O-methyl, or 2'-OH modification of one or more nucleotides; one or more phosphorothioate modifications of the backbone; and a non-nucleotide moiety; wherein the at least one chemical modification confers reduced immunostimulatory activity, increased serum stability, or both, as compared to a corresponding short hairpin nucleic acid molecule not having the chemical modification.

In certain embodiments, the pyrimidine nucleotides comprise 2'-O-methylpyrimidine nucleotides and/or 2'-deoxypyrimidine nucleotides.

In certain embodiments, some or all of the purine nucleotides can comprise 2'-O-methylpurine nucleotides and/or 2'-deoxy-purine nucleotides.

In certain embodiments, the chemical modification is present in nucleotides proximal to the 3' and/or 5' ends of the nucleic acid molecule of the invention.

In certain embodiments, a nucleic acid molecule of the invention can have enhanced resistance to nucleases. For increased nuclease resistance, a nucleic acid molecule, can include, for example, 2'-modified ribose units and/or phosphorothioate linkages. For example, the 2' hydroxyl group (OH) can be modified or replaced with a number of different "oxy" or "deoxy" substituents.

For increased nuclease resistance the nucleic acid molecules of the invention can include 2'-O-methyl, 2'-fluorine, 2'-O-methoxyethyl, 2'-O-aminopropyl, 2'-amino, and/or phosphorothioate linkages. Inclusion of locked nucleic acids (LNA), ethylene nucleic acids (ENA), e.g., 2'-4'-ethylene-bridged nucleic acids, and certain nucleobase modifications such as 2-amino-A, 2-thio (e.g., 2-thio-U), G-clamp modifications, can also increase binding affinity to a target.

In one embodiment, the nucleic acid molecule includes a 2'-modified nucleotide, e.g., a 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O-NMA). In one embodiment, the nucleic acid molecule includes at least one 2'-O-methyl-modified nucleotide, and in some embodiments, all of the nucleotides of the nucleic acid molecule include a 2'-O-methyl modification.

Examples of "oxy"-2' hydroxyl group modifications include alkoxy or aryloxy (OR, e.g., R=H, alkyl, cycloalkyl, aryl, aralkyl, heteroaryl or sugar); polyethyleneglycols (PEG), O(CH$_2$CH$_2$O)$_n$CH$_2$CH$_2$OR; "locked" nucleic acids (LNA) in which the 2' hydroxyl is connected, e.g., by a methylene bridge, to the 4' carbon of the same ribose sugar; amine, O-AMINE and aminoalkoxy, O(CH$_2$)$_n$AMINE, (e.g., AMINE=NH$_2$; alkylamino, dialkylamino, heterocyclyl amino, arylamino, diaryl amino, heteroaryl amino, or diheteroaryl amino, ethylene diamine, polyamino). It is noteworthy that oligonucleotides containing only the methoxyethyl group (MOE), (OCH$_2$CH$_2$OCH$_3$, a PEG derivative), exhibit nuclease stabilities comparable to those modified with the robust phosphorothioate modification.

"Deoxy" modifications include hydrogen (i.e. deoxyribose sugars); halo (e.g., fluoro); amino (e.g. NH$_2$; alkylamino, dialkylamino, heterocyclyl, arylamino, diaryl amino, heteroaryl amino, diheteroaryl amino, or amino acid); NH(CH$_2$CH$_2$NH)$_n$CH$_2$CH$_2$-AMINE (AMINE=NH$_2$; alkylamino, dialkylamino, heterocyclyl amino, arylamino, diaryl amino, heteroaryl amino, or diheteroaryl amino), —NHC(O)R (R=alkyl, cycloalkyl, aryl, aralkyl, heteroaryl or sugar), cyano; mercapto; alkyl-thio-alkyl; thioalkoxy; and alkyl, cycloalkyl, aryl, alkenyl and alkynyl, which may be optionally substituted with e.g., an amino functionality.

Preferred substitutents are 2'-methoxyethyl, 2'-OCH3, 2'-O-allyl, 2'-C-allyl, and 2'-fluoro.

One way to increase resistance is to identify cleavage sites and modify such sites to inhibit cleavage. For example, the dinucleotides 5'-UA-3', 5'-UG-3', 5'-CA-3', 5'-UU-3', or 5'-CC-3' can serve as cleavage sites. Enhanced nuclease resistance can therefore be achieved by modifying the 5' nucleotide, resulting, for example, in at least one 5'-uridine-adenine-3' (5'-UA-3') dinucleotide wherein the uridine is a 2'-modified nucleotide; at least one 5'-uridine-guanine-3' (5'-UG-3') dinucleotide, wherein the 5'-uridine is a 2'-modified nucleotide; at least one 5'-cytidine-adenine-3' (5'-CA-3') dinucleotide, wherein the 5'-cytidine is a 2'-modified nucleotide; at least one 5'-uridine-uridine-3' (5'-UU-3') dinucleotide, wherein the 5'-uridine is a 2'-modified nucleotide; or at least one 5'-cytidine-cytidine-3' (5'-CC-3') dinucleotide, wherein the 5'-cytidine is a 2'-modified nucleotide. The oligonucleotide molecule can include at least 2, at least 3, at least 4 or at least 5 of such dinucleotides. In certain embodiments, all the pyrimidines of a nucleic acid molecule carry a 2'-modification, and the nucleic acid molecule therefore has enhanced resistance to endonucleases.

With respect to phosphorothioate linkages that serve to increase protection against RNase activity, the nucleic acid molecule can include a phosphorothioate at least the first, second, or third internucleotide linkage at the 5' or 3' end of the nucleotide sequence. To maximize nuclease resistance, the 2' modifications can be used in combination with one or more phosphate linker modifications (e.g., phosphorothioate).

In certain embodiments, the inclusion of pyranose sugars in the nucleic acid backbone can also decrease endonucleolytic cleavage. The certain embodiments, inclusion of furanose sugars in the nucleic acid backbone can also decrease endonucleolytic cleavage.

In certain embodiments, the 5'-terminus can be blocked with an aminoalkyl group, e.g., a 5'-O-alkylamino substituent. Other 5' conjugates can inhibit 5'-3' exonucleolytic cleavage. While not being bound by theory, a 5' conjugate, may inhibit exonucleolytic cleavage by sterically blocking the exonuclease from binding to the 5'-end of oligonucleotide. Even small alkyl chains, aryl groups, or heterocyclic conjugates or modified sugars (D-ribose, deoxyribose, glucose etc.) can block 5'-3-exonucleases.

Thus, a nucleic acid molecule can include modifications so as to inhibit degradation, e.g., by nucleases, e.g., endonucleases or exonucleases, found in the body of a subject. These monomers are referred to herein as NRMs, or Nuclease Resistance promoting Monomers, the corresponding modifications as NRM modifications. In many cases these modifications will modulate other properties of the oligonucleotide molecule as well, e.g., the ability to interact with a protein, e.g., a transport protein, e.g., serum albumin.

One or more different NRM modifications can be introduced into a nucleic acid molecule or into a sequence of a nucleic acid molecule. An NRM modification can be used more than once in a sequence or in a nucleic acid molecule.

NRM modifications include some which can be placed only at the terminus and others which can go at any position. Some NRM modifications that can inhibit hybridization are preferably used only in terminal regions, and more preferably not at the cleavage site or in the cleavage region of a nucleic acid molecule.

Such modifications can be introduced into the terminal regions, e.g., at the terminal position or with 2, 3, 4, or 5 positions of the terminus, of a sequence which targets or a sequence which does not target a sequence in the subject.

In one embodiment, a nucleic acid molecule, includes a modification that improves targeting, e.g. a targeting modification described herein. Examples of modifications that target a nucleic acid molecule to particular cell types include carbohydrate sugars such as galactose, N-acetylgalactosamine, mannose; vitamins such as folates; other ligands such as RGDs and RGD mimics; and small molecules including naproxen, ibuprofen or other known protein-binding molecules.

A nucleic acid molecule can be constructed using chemical synthesis and/or enzymatic ligation reactions using procedures known in the art. For example, a nucleic acid molecule can be chemically synthesized using naturally occurring nucleotides or variously modified nucleotides designed to increase the biological stability of the molecules or to increase the physical stability of the binding between the nucleic acid molecule and target, e.g., phosphorothioate derivatives and acridine substituted nucleotides can be used. Other appropriate nucleic acid modifications are described herein. Alternatively, the nucleic acid molecule can be produced biologically using an expression vector.

The term "halo" refers to any radical of fluorine, chlorine, bromine or iodine.

The term "alkyl" refers to a hydrocarbon chain that may be a straight chain or branched chain, containing the indicated number of carbon atoms. For example, $C_1$-$C_{12}$ alkyl indicates that the group may have from 1 to 12 (inclusive) carbon atoms in it. The term "haloalkyl" refers to an alkyl in which one or more hydrogen atoms are replaced by halo, and includes alkyl moieties in which all hydrogens have been replaced by halo (e.g., perfluoroalkyl). Alkyl and haloalkyl groups may be optionally inserted with O, N, or S. The terms "aralkyl" refers to an alkyl moiety in which an alkyl hydrogen atom is replaced by an aryl group. Aralkyl includes groups in which more than one hydrogen atom has been replaced by an aryl group. Examples of "aralkyl" include benzyl, 9-fluorenyl, benzhydryl, and trityl groups.

The term "alkenyl" refers to a straight or branched hydrocarbon chain containing 2-8 carbon atoms and characterized in having one or more double bonds. Examples of a typical alkenyl include, but not limited to, allyl, propenyl, 2-butenyl, 3-hexenyl and 3-octenyl groups. The term "alkynyl" refers to a straight or branched hydrocarbon chain containing 2-8 carbon atoms and characterized in having one or more triple bonds. Some examples of a typical alkynyl are ethynyl, 2-propynyl, and 3-methylbutynyl, and propargyl. The $sp^2$ and $sp^3$ carbons may optionally serve as the point of attachment of the alkenyl and alkynyl groups, respectively.

The terms "alkylamino" and "dialkylamino" refer to —NH(alkyl) and —NH(alkyl)$_2$ radicals respectively. The term "aralkylamino" refers to a —NH(aralkyl) radical. The term "alkoxy" refers to an —O-alkyl radical, and the terms "cycloalkoxy" and "aralkoxy" refer to an —O-cycloalkyl and O-aralkyl radicals respectively. The term "siloxy" refers to a $R_3SiO$— radical. The term "mercapto" refers to an SH radical. The term "thioalkoxy" refers to an —S-alkyl radical.

The term "alkylene" refers to a divalent alkyl (i.e., —R—), e.g., —CH$_2$—, —CH$_2$CH$_2$—, and —CH$_2$CH$_2$CH$_2$—. The term "alkylenedioxo" refers to a divalent species of the structure —O—R—O—, in which R represents an alkylene.

The term "aryl" refers to an aromatic monocyclic, bicyclic, or tricyclic hydrocarbon ring system, wherein any ring atom can be substituted. Examples of aryl moieties include, but are not limited to, phenyl, naphthyl, anthracenyl, and pyrenyl.

The term "cycloalkyl" as employed herein includes saturated cyclic, bicyclic, tricyclic, or polycyclic hydrocarbon groups having 3 to 12 carbons, wherein any ring atom can be substituted. The cycloalkyl groups herein described may also contain fused rings. Fused rings are rings that share a common carbon-carbon bond or a common carbon atom (e.g., spiro-fused rings). Examples of cycloalkyl moieties include, but are not limited to, cyclohexyl, adamantyl, and norbornyl, and decalin.

The term "heterocyclyl" refers to a nonaromatic 3-10 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein any ring atom can be substituted. The heterocyclyl groups herein described may also contain fused rings. Fused rings are rings that share a common carbon-carbon bond or a common carbon atom (e.g., spiro-fused rings). Examples of heterocyclyl include, but are not limited to tetrahydrofuranyl, tetrahydropyranyl, piperidinyl, morpholino, pyrrolinyl and pyrrolidinyl.

The term "cycloalkenyl" as employed herein includes partially unsaturated, nonaromatic, cyclic, bicyclic, tricyclic, or polycyclic hydrocarbon groups having 5 to 12 carbons, preferably 5 to 8 carbons, wherein any ring atom can be substituted. The cycloalkenyl groups herein described may also contain fused rings. Fused rings are rings that share a common carbon-carbon bond or a common carbon atom (e.g., spiro-fused rings). Examples of cycloalkenyl moieties include, but are not limited to cyclohexenyl, cyclohexadienyl, or norbornenyl.

The term "heterocycloalkenyl" refers to a partially saturated, nonaromatic 5-10 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein any ring atom can be substituted. The heterocycloalkenyl groups herein described may also contain fused rings. Fused rings are rings that share a common carbon-carbon bond or a common carbon atom (e.g., spiro-fused rings). Examples of heterocycloalkenyl include but are not limited to tetrahydropyridyl and dihydropyran.

The term "heteroaryl" refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein any ring atom can be substituted. The heteroaryl groups herein described may also contain fused rings that share a common carbon-carbon bond.

The term "oxo" refers to an oxygen atom, which forms a carbonyl when attached to carbon, an N-oxide when attached to nitrogen, and a sulfoxide or sulfone when attached to sulfur.

The term "acyl" refers to an alkylcarbonyl, cycloalkylcarbonyl, arylcarbonyl, heterocyclylcarbonyl, or heteroarylcarbonyl substituent, any of which may be further substituted by substituents.

The term "substituents" refers to a group "substituted" on an alkyl, cycloalkyl, alkenyl, alkynyl, heterocyclyl, heterocycloalkenyl, cycloalkenyl, aryl, or heteroaryl group at any atom of that group. Suitable substituents include, without limitation, alkyl, alkenyl, alkynyl, alkoxy, halo, hydroxy, cyano, nitro, amino, $SO_3H$, sulfate, phosphate, perfluoroalkyl, perfluoroalkoxy, methylenedioxy, ethylenedioxy, carboxyl, oxo, thioxo, imino (alkyl, aryl, aralkyl), $S(O)_n$alkyl (where n is 0-2), $S(O)_n$aryl (where n is 0-2), $S(O)_n$heteroaryl (where n is 0-2), $S(O)_n$heterocyclyl (where n is 0-2), amine (mono-, di-, alkyl, cycloalkyl, aralkyl, heteroaralkyl, and combinations thereof), ester (alkyl, aralkyl, heteroaralkyl), amide (mono-, di-, alkyl, aralkyl, heteroaralkyl, and combinations thereof), sulfonamide (mono-, di-, alkyl, aralkyl, heteroaralkyl, and combinations thereof), unsubstituted aryl, unsubstituted heteroaryl, unsubstituted heterocyclyl, and unsubstituted cycloalkyl. In one aspect, the substituents on a group are independently any one single, or any subset of the aforementioned substituents. The terms "adeninyl, cytosinyl, guaninyl, thyminyl, and uracilyl" and the like refer to radicals of adenine, cytosine, guanine, thymine, and uracil.

A "protected" moiety refers to a reactive functional group, e.g., a hydroxyl group or an amino group, or a class of molecules, e.g., sugars, having one or more functional groups, in which the reactivity of the functional group is temporarily blocked by the presence of an attached protecting group. Protecting groups useful for the monomers and methods described herein can be found, e.g., in Greene, T. W., *Protective Groups in Organic Synthesis* (John Wiley and Sons: New York), 1981, which is hereby incorporated by reference.

For ease of exposition the term nucleotide or ribonucleotide is sometimes used herein in reference to one or more monomeric subunits of an oligonucleotide agent. It will be understood herein that the usage of the term "ribonucleotide" or "nucleotide" herein can, in the case of a modified RNA or nucleotide surrogate, also refer to a modified nucleotide, or surrogate replacement moiety at one or more positions.

In certain embodiments, the nucleic acid molecule of the invention preferably has one or more of the following properties:

(1) a 5' modification that includes one or more phosphate groups or one or more analogs of a phosphate group;

(2) despite modifications, even to a very large number of bases specifically base pair and form a duplex structure with a double-stranded region;

(3) despite modifications, even to a very large number, or all of the nucleosides, still have "RNA-like" properties, i.e., it will possess the overall structural, chemical and physical properties of an RNA molecule, even though not exclusively, or even partly, of ribonucleotide-based content. For example, all of the nucleotide sugars can contain e.g., 2'OMe, 2'fluoro in place of 2' hydroxyl. This deoxyribonucleotide-containing agent can still be expected to exhibit RNA-like properties. While not wishing to be bound by theory, an electronegative fluorine prefers an axial orientation when attached to the C2' position of ribose. This spatial preference of fluorine can, in turn, force the sugars to adopt a $C_{3'}$-endo pucker. This is the same puckering mode as observed in RNA molecules and gives rise to the RNA-characteristic A-family-type helix. Further, since fluorine is a good hydrogen bond acceptor, it can participate in the same hydrogen bonding interactions with water molecules that are known to stabilize RNA structures. (Generally, it is preferred that a modified moiety at the 2' sugar position will be able to enter into hydrogen-bonding which is more characteristic of the 2'-OH moiety of a ribonucleotide than the 2'-H moiety of a deoxyribonucleotide. In one embodiment, the oligonucleotide molecule will: exhibit a $C_{3'}$-endo pucker in all, or at least 50, 75, 80, 85, 90, or 95% of its sugars; exhibit a $C_{3'}$-endo pucker in a sufficient amount of its sugars that it can give rise to a the RNA-characteristic A-family-type helix; will have no more than 20, 10, 5, 4, 3, 2, or 1 sugar which is not a $C_{3'}$-endo pucker structure.

2'-modifications with C3'-endo sugar pucker include 2'-OH, 2'-O-Me, 2'-O-methoxyethyl, 2'-O-aminopropyl, 2'-F, 2'-O—CH2-CO—NHMe, 2'-O—CH2-CH2-O—CH2-CH2-N(Me)2, and LNA.

2'-modifications with a C2'-endo sugar pucker include 2'-H, 2'-Me, 2'-S-Me, 2'-Ethynyl, 2'-ara-F.

Sugar modifications can also include L-sugars and 2'-5'-linked sugars.

Nucleic acid agents discussed herein include otherwise unmodified RNA and DNA as well as RNA and DNA that have been modified, e.g., to improve efficacy, and polymers of nucleoside surrogates. Unmodified RNA refers to a molecule in which the components of the nucleic acid, namely sugars, bases, and phosphate moieties, are the same or essentially the same as that which occur in nature, preferably as occur naturally in the human body. The art has referred to rare or unusual, but naturally occurring, RNAs as modified RNAs, see, e.g., Limbach et al. (*Nucleic Acids Res.*, 1994, 22:2183-2196). Such rare or unusual RNAs, often termed modified RNAs, are typically the result of a post-transcriptional modification and are within the term unmodified RNA as used herein. Modified RNA, as used herein, refers to a molecule in which one or more of the components of the nucleic acid, namely sugars, bases, and phosphate moieties, are different from that which occur in nature, preferably different from that which occurs in the human body. While they are referred to as "modified RNAs" they will of course, because of the modification, include molecules that are not, strictly speaking, RNAs. Nucleoside surrogates are molecules in which the ribophosphate backbone is replaced with a non-ribophosphate construct that allows the bases to be presented in the correct spatial relationship such that hybridization is substantially similar to what is seen with a ribophosphate backbone, e.g., non-charged mimics of the ribophosphate backbone. Examples of all of the above are discussed herein.

As nucleic acids are polymers of subunits or monomers, many of the modifications described below occur at a position which is repeated within a nucleic acid, e.g., a modification of a base, or a phosphate moiety, or a non-linking O of a phosphate moiety. In some cases the modification will occur at all of the subject positions in the nucleic acid but in many, and in fact in most cases it will not. By way of example, a modification may only occur at a 3' or 5' terminal position, in a terminal region, e.g., at a position on a terminal nucleotide, or in the last 2, 3, 4, 5, or 10 nucleotides of a strand. The ligand can be attached at the 3' end, the 5' end, or at an internal position, or at a combination of these positions. For example, the ligand can be at the 3' end and the 5' end; at the 3' end and at one or more internal positions; at the 5' end and at one or more internal positions; or at the 3' end, the 5' end, and at one or more internal positions. For example, a phosphorothioate modification at a non-linking O position may only occur at one or both termini, or may only occur in a terminal region, e.g., at a position on a terminal nucleotide or in the last 2, 3, 4, 5, or 10 nucleotides of the nucleic acid. The 5' end can be phosphorylated.

Modifications and nucleotide surrogates are discussed below.

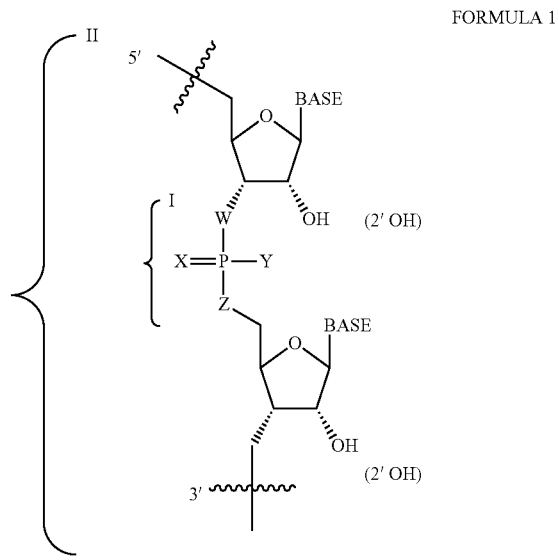

FORMULA 1

The scaffold presented above in Formula 1 represents a portion of a ribonucleic acid. The basic components are the ribose sugar, the base, the terminal phosphates, and phosphate internucleotide linkers. Where the bases are naturally occurring bases, e.g., adenine, uracil, guanine or cytosine, the sugars are the unmodified 2' hydroxyl ribose sugar (as depicted) and W, X, Y, and Z are all O, Formula 1 represents a naturally occurring unmodified oligoribonucleotide.

Unmodified oligoribonucleotides may be less than optimal in some applications, e.g., unmodified oligoribonucleotides can be prone to degradation by e.g., cellular nucleases. Nucleases can hydrolyze nucleic acid phosphodiester bonds. However, chemical modifications to one or more of the above RNA components can confer improved properties, and, for example, can render oligoribonucleotides more stable to nucleases. Unmodified oligoribonucleotides may also be less than optimal in terms of offering tethering points for attaching ligands or other moieties to a nucleic acid agent.

Modified nucleic acids and nucleotide surrogates can include one or more of:

(i) alteration, e.g., replacement, of one or both of the non-linking (X and Y) phosphate oxygens and/or of one or more of the linking (W and Z) phosphate oxygens (When the phosphate is in the terminal position, one of the positions W or Z will not link the phosphate to an additional element in a naturally occurring ribonucleic acid. However, for simplicity of terminology, except where otherwise noted, the W position at the 5' end of a nucleic acid and the terminal Z position at the 3' end of a nucleic acid, are within the term "linking phosphate oxygens" as used herein);

(ii) alteration, e.g., replacement, of a constituent of the ribose sugar, e.g., of the 2' hydroxyl on the ribose sugar, or wholesale replacement of the ribose sugar with a structure other than ribose, e.g., as described herein;

(iii) wholesale replacement of the phosphate moiety (bracket I) with "dephospho" linkers;

(iv) modification or replacement of a naturally occurring base;

(v) replacement or modification of the ribose-phosphate backbone (bracket II);

(vi) modification of the 3' end or 5' end of the RNA, e.g., removal, modification or replacement of a terminal phosphate group or conjugation of a moiety, such as a fluorescently labeled moiety, to either the 3' or 5' end of RNA.

The terms replacement, modification, alteration, and the like, as used in this context, do not imply any process limitation, e.g., modification does not mean that one must start with a reference or naturally occurring ribonucleic acid and modify it to produce a modified ribonucleic acid but rather modified simply indicates a difference from a naturally occurring molecule.

It is understood that the actual electronic structure of some chemical entities cannot be adequately represented by only one canonical form (i.e. Lewis structure). While not wishing to be bound by theory, the actual structure can instead be some hybrid or weighted average of two or more canonical forms, known collectively as resonance forms or structures. Resonance structures are not discrete chemical entities and exist only on paper. They differ from one another only in the placement or "localization" of the bonding and nonbonding electrons for a particular chemical entity. It can be possible for one resonance structure to contribute to a greater extent to the hybrid than the others. Thus, the written and graphical descriptions of the embodiments of the present invention are made in terms of what the art recognizes as the predominant resonance form for a particular species. For example, any phosphoroamidate (replacement of a nonlinking oxygen with nitrogen) would be represented by X=O and Y=N in the above figure.

Specific modifications are discussed in more detail below.

The Phosphate Group

The phosphate group is a negatively charged species. The charge is distributed equally over the two non-linking oxygen atoms (i.e., X and Y in Formula 1 above). However, the phosphate group can be modified by replacing at least one of the oxygens with a different substituent. One result of this modification to RNA phosphate backbones can be increased resistance of the oligoribonucleotide to nucleolytic breakdown. Thus while not wishing to be bound by theory, it can be desirable in some embodiments to introduce alterations which result in either an uncharged linker or a charged linker with unsymmetrical charge distribution.

Examples of modified phosphate groups include phosphorothioate, phosphoroselenates, borano phosphates, borano phosphate esters, hydrogen phosphonates, phosphoroamidates, alkyl or aryl phosphonates and phosphotriesters. Phosphorodithioates have both non-linking oxygens replaced by sulfur. Unlike the situation where only one of X or Y is altered, the phosphorus center in the phosphorodithioates is achiral which precludes the formation of oligoribonucleotides diastereomers. Diastereomer formation can result in a preparation in which the individual diastereomers exhibit varying resistance to nucleases. Further, the hybridization affinity of RNA containing chiral phosphate groups can be lower relative to the corresponding unmodified RNA species. Thus, while not wishing to be bound by theory, modifications to both X and Y which eliminate the chiral center, e.g., phosphorodithioate formation, may be desirable in that they cannot produce diastereomer mixtures. Thus, X can be any one of S, Se, B, C, H, N, or OR (R is alkyl or aryl). Thus Y can be any one of S, Se, B, C, H, N, or OR (R is alkyl or aryl). Replacement of X and/or Y with sulfur is preferred.

The phosphate linker can also be modified by replacement of a linking oxygen (i.e., W or Z in Formula 1) with nitrogen (bridged phosphoroamidates), sulfur (bridged phosphorothioates) and carbon (bridged methylenephosphonates). The replacement can occur at a terminal oxygen (position W (3') or position Z (5')). Replacement of W with carbon or Z with nitrogen is preferred.

Candidate agents can be evaluated for suitability as described below.

The Sugar Group A modified RNA can include modification of all or some of the sugar groups of the ribonucleic acid. For example, the 2' hydroxyl group (OH) can be modified or replaced with a number of different "oxy" or "deoxy" substituents. While not being bound by theory, enhanced stability is expected since the hydroxyl can no longer be deprotonated to form a 2' alkoxide ion. The 2' alkoxide can catalyze degradation by intramolecular nucleophilic attack on the linker phosphorus atom. Again, while not wishing to be bound by theory, it can be desirable to some embodiments to introduce alterations in which alkoxide formation at the 2' position is not possible.

Examples of "oxy"-2' hydroxyl group modifications include alkoxy or aryloxy (OR, e.g., R=H, alkyl, cycloalkyl, aryl, aralkyl, heteroaryl or sugar); polyethyleneglycols (PEG), $O(CH_2CH_2O)_nCH_2CH_2OR$; "locked" nucleic acids (LNA) in which the 2' hydroxyl is connected, e.g., by a methylene bridge or ethylene bridge (e.g., 2'-4'-ethylene bridged nucleic acid (ENA)), to the 4' carbon of the same ribose sugar; amino, O-AMINE (AMINE=$NH_2$; alkylamino, dialkylamino, heterocyclyl, arylamino, diaryl amino, heteroaryl amino, or diheteroaryl amino, ethylene diamine, polyamino) and aminoalkoxy, $O(CH_2)_nAMINE$, (e.g., $AMINE=NH_2$; alkylamino, dialkylamino, heterocyclyl, arylamino, diaryl amino, heteroaryl amino, or diheteroaryl amino, ethylene diamine, polyamino). It is noteworthy that oligonucleotides containing only the methoxyethyl group (MOE), ($OCH_2CH_2OCH_3$, a PEG derivative), exhibit nuclease stabilities comparable to those modified with the robust phosphorothioate modification.

"Deoxy" modifications include hydrogen (i.e. deoxyribose sugars); halo (e.g., fluoro); amino (e.g. $NH_2$; alkylamino, dialkylamino, heterocyclyl, arylamino, diaryl amino, heteroaryl amino, diheteroaryl amino, or amino acid); $NH(CH_2CH_2NH)_nCH_2CH_2$-AMINE ($AMINE=NH_2$; alkylamino, dialkylamino, heterocyclyl, arylamino, diaryl amino, heteroaryl amino, or diheteroaryl amino), —NHC(O)R (R=alkyl, cycloalkyl, aryl, aralkyl, heteroaryl or sugar), cyano; mercapto; alkyl-thio-alkyl; thioalkoxy; and alkyl, cycloalkyl, aryl, alkenyl and alkynyl, which may be optionally substituted with e.g., an amino functionality. Preferred substitutents are 2'-methoxyethyl, 2'-OCH3, 2'-O-allyl, 2'-C-allyl, and 2'-fluoro.

The sugar group can also contain one or more carbons that possess the opposite stereochemical configuration than that of the corresponding carbon in ribose. Thus, a modified RNA can include nucleotides containing e.g., arabinose, as the sugar. Modified RNAs can also include "abasic" sugars, which lack a nucleobase at C-1'. These abasic sugars can also contain modifications at one or more of the constituent sugar atoms.

To maximize nuclease resistance, the 2' modifications can be used in combination with one or more phosphate linker modifications (e.g., phosphorothioate). The so-called "chimeric" oligonucleotides are those that contain two or more different modifications.

The modification can also entail the wholesale replacement of a ribose structure with another entity (an SRMS) at one or more sites in the nucleic acid agent.

Candidate modifications can be evaluated as described below.

Replacement of the Phosphate Group

The phosphate group can be replaced by non-phosphorus containing connectors (cf. Bracket I in Formula 1 above). While not wishing to be bound by theory, it is believed that since the charged phosphodiester group is the reaction center in nucleolytic degradation, its replacement with neutral structural mimics should impart enhanced nuclease stability. Again, while not wishing to be bound by theory, it can be desirable, in some embodiment, to introduce alterations in which the charged phosphate group is replaced by a neutral moiety.

Examples of moieties which can replace the phosphate group include siloxane, carbonate, carboxymethyl, carbamate, amide, thioether, ethylene oxide linker, sulfonate, sulfonamide, thioformacetal, formacetal, oxime, methyleneimino, methylenemethylimino, methylenehydrazo, methylenedimethylhydrazo and methyleneoxymethylimino. Preferred replacements include the methylenecarbonylamino and methylenemethylimino groups.

Candidate modifications can be evaluated as described below.

Replacement of Ribophosphate Backbone

Oligonucleotide-mimicking scaffolds can also be constructed wherein the phosphate linker and ribose sugar are replaced by nuclease resistant nucleoside or nucleotide surrogates (see Bracket II of Formula 1 above). While not wishing to be bound by theory, it is believed that the absence of a repetitively charged backbone diminishes binding to proteins that recognize polyanions (e.g. nucleases). Again, while not wishing to be bound by theory, it can be desirable in some embodiment, to introduce alterations in which the bases are tethered by a neutral surrogate backbone.

Examples include the mophilino, cyclobutyl, pyrrolidine and peptide nucleic acid (PNA) nucleoside surrogates. A preferred surrogate is a PNA surrogate. Candidate modifications can be evaluated as described below.

Terminal Modifications

The 3' and 5' ends of an oligonucleotide can be modified. Such modifications can be at the 3' end, 5' end or both ends of the molecule. They can include modification or replacement of an entire terminal phosphate or of one or more of the atoms of the phosphate group. E.g., the 3' and 5' ends of an oligonucleotide can be conjugated to other functional molecular entities such as labeling moieties, e.g., fluorophores (e.g., pyrene, TAMRA, fluorescein, Cy3 or Cy5 dyes) or protecting groups (based e.g., on sulfur, silicon, boron or ester). The functional molecular entities can be attached to the sugar through a phosphate group and/or a spacer. The terminal atom of the spacer can connect to or replace the linking atom of the phosphate group or the C-3' or C-5' O, N, S or C group of the sugar. Alternatively, the spacer can connect to or replace the terminal atom of a nucleotide surrogate (e.g., PNAs). These spacers or linkers can include e.g., —$(CH_2)_n$—, —$(CH_2)_nN$—, —$(CH_2)_nO$—, —$(CH_2)$—S—, $O(CH_2CH_2O)_nCH_2CH_2OH$ (e.g., n=3 or 6), abasic sugars, amide, carboxy, amine, oxyamine, oxyimine, thioether, disulfide, thiourea, sulfonamide, or morpholino, or biotin and fluorescein reagents. While not wishing to be bound by theory, it is believed that conjugation of certain moieties can improve transport, hybridization, and specificity properties. Again, while not wishing to be bound by theory, it may be desirable to introduce terminal alterations that improve nuclease resistance. Other examples of terminal modifications include dyes, intercalating agents (e.g. acridines), cross-linkers (e.g. psoralene, mitomycin C), porphyrins (TPPC4, texaphyrin, Sapphyrin), polycyclic aromatic hydrocarbons (e.g., phenazine, dihydrophenazine), artificial endonucleases (e.g. EDTA), lipophilic carriers (e.g., cholesterol, cholic acid, adamantane acetic acid, 1-pyrene butyric acid, dihydrotestosterone, 1,3-Bis-O(hexadecyl)glycerol, geranyloxyhexyl group, hexadecylglycerol, borneol, menthol, 1,3-propanediol, heptadecyl group, palmitic acid, myristic acid, O3-(oleoyl)lithocholic acid, O3-(oleoyl)cholenic acid, dimethoxytrityl, or phenoxazine) and peptide conjugates (e.g., antennapedia peptide, Tat peptide), alkylating agents, phosphate, amino, mercapto, PEG (e.g., PEG-40K), MPEG, $[MPEG]_2$, polyamino, alkyl, substituted alkyl, radiolabeled markers, enzymes, haptens (e.g. biotin), transport/absorption facilitators (e.g., aspirin, vitamin E, folic acid), synthetic ribonucleases (e.g., imidazole, bisimidazole, histamine, imidazole clusters, acridine-imidazole conjugates, Eu3+ complexes of tetraazamacrocycles).

Terminal modifications can be added for a number of reasons, including as discussed elsewhere herein to modulate activity or to modulate resistance to degradation. Preferred modifications include the addition of a methylphosphonate at the 3'-most terminal linkage; a 3' C5-aminoalkyl-dT; 3' cationic group; or another 3' conjugate to inhibit 3'-5' exonucleolytic degradation.

Terminal modifications useful for modulating activity include modification of the 5' end with phosphate or phosphate analogs. For example, in certain embodiments, oligonucleotide agents are 5' phosphorylated or include a phosphoryl analog at the 5' terminus. Suitable modifications include: 5'-monophosphate ((HO)2(O)P—O-5'); 5'-diphosphate ((HO)2(O)P—O—P(HO)(O)—O-5'); 5'-triphosphate ((HO)2(O)P—O—(HO)(O)P—O—P(HO)(O)—O-5'); 5'-guanosine cap (7-methylated or non-methylated) (7m-G-O-5'-(HO)(O)P—O—(HO)(O)P—O—P(HO)(O)—O-5'); 5'-adenosine cap (Appp), and any modified or unmodified nucleotide cap structure (N—O-5'-(HO)(O)P—O—(HO)(O)P—O—P(HO)(O)—O-5'); 5'-monothiophosphate (phosphorothioate; (HO)2(S)P—O-5'); 5'-monodithiophosphate (phosphorodithioate; (HO)(HS)(S)P—O-5'), 5'-phosphorothiolate ((HO)2(O)P—S-5'); any additional combination of oxygen/sulfur replaced monophosphate, diphosphate and triphosphates (e.g. 5'-alpha-thiotriphosphate, 5'-gamma-thiotriphosphate, etc.), 5'-phosphoramidates ((HO)2(O)P—NH-5', (HO)(NH2)(O)P—O-5'), 5'-alkylphosphonates (R=alkyl=methyl, ethyl, isopropyl, propyl, etc., e.g. RP(OH)(O)—O-5'-, (OH)2(O)P-5'-CH2-), 5'-alkyletherphosphonates (R=alkylether=methoxymethyl (MeOCH2-), ethoxymethyl, etc., e.g. RP(OH)(O)—O-5'-).

Terminal modifications can also be useful for monitoring distribution, and in such cases the preferred groups to be added include fluorophores, e.g., fluorscein or an Alexa dye, e.g., Alexa 488. Terminal modifications can also be useful for enhancing uptake, useful modifications for this include cholesterol. Terminal modifications can also be useful for cross-linking anantagomir to another moiety; modifications useful for this include mitomycin C.

Candidate modifications can be evaluated as described below.

The Bases

Adenine, guanine, cytosine and uracil are the most common bases found in RNA. These bases can be modified or replaced to provide RNA's having improved properties. For example, nuclease resistant oligoribonucleotides can be prepared with these bases or with synthetic and natural nucleobases (e.g., inosine, thymine, xanthine, hypoxanthine, nubularine, isoguanisine, or tubercidine) and any one of the above modifications. Alternatively, substituted or modified analogs of any of the above bases, e.g., "unusual bases" and "universal bases" described herein, can be employed. Examples include without limitation 2-aminoadenine, 6-methyl and other alkyl derivatives of adenine and guanine, 2-propyl and other alkyl derivatives of adenine and guanine, 5-halouracil and cytosine, 5-propynyl uracil and cytosine, 6-azo uracil, cytosine and thymine, 5-uracil (pseudouracil), 4-thiouracil, 5-halouracil, 5-(2-aminopropyl)uracil, 5-amino allyl uracil, 8-halo, amino, thiol, thioalkyl, hydroxyl and other 8-substituted adenines and guanines, 5-trifluoromethyl and other 5-substituted uracils and cytosines, 7-methylguanine, 5-substituted pyrimidines, 6-azapyrimidines and N-2, N-6 and 0-6 substituted purines, including 2-aminopropyladenine, 5-propynyluracil and 5-propynylcytosine, dihydrouracil, 3-deaza-5-azacytosine, 2-aminopurine, 5-alkyluracil, 7-alkylguanine, 5-alkyl cytosine, 7-deazaadenine, N6,N6-dimethyladenine, 2,6-diaminopurine, 5-amino-allyl-uracil, N3-methyluracil, substituted 1,2,4-triazoles, 2-pyridinone, 5-nitroindole, 3-nitropyrrole, 5-methoxyuracil, uracil-5-oxyacetic acid, 5-methoxycarbonylmethyluracil, 5-methyl-2-thiouracil, 5-methoxycarbonylmethyl-2-thiouracil, 5-methylaminomethyl-2-thiouracil, 3-(3-amino-3carboxypropyl)uracil, 3-methylcytosine, 5-methylcytosine, $N^4$-acetyl cytosine, 2-thiocytosine, N6-methyladenine, N6-isopentyladenine, 2-methylthio-N6-isopentenyladenine, N-methylguanines, or O-alkylated bases. Further purines and pyrimidines include those disclosed in U.S. Pat. No. 3,687,808, those disclosed in the Concise Encyclopedia Of Polymer Science And Engineering, pages 858-859, Kroschwitz, J. I., ed. John Wiley & Sons, 1990, and those disclosed by Englisch et al., Angewandte Chemie, International Edition, 1991, 30, 613.

Candidate modifications can be evaluated as described below.

Evaluation of Candidate Nucleic Acid Agents

One can evaluate a candidate nucleic acid molecule, for a selected property by exposing the molecule or modified molecule and a control molecule to the appropriate conditions and evaluating for the presence of the selected property. For example, resistance to a degradent can be evaluated as follows. A candidate modified nucleic acid molecule can be exposed to degradative conditions, e.g., exposed to a milieu, which includes a degradative agent, e.g., a nuclease. For example, one can use a biological sample, e.g., one that is similar to a milieu, which might be encountered, in therapeutic use, e.g., blood or a cellular fraction, e.g., a cell-free homogenate or disrupted cells. The candidate and control can then be evaluated for resistance to degradation by any of a number of approaches. For example, the candidate and control could be labeled, preferably prior to exposure, with, e.g., a radioactive or enzymatic label, or a fluorescent label, such as Cy3 or Cy5. Control and modified nucleic acid molecules can be incubated with the degradative agent, and optionally a control, e.g., an inactivated, e.g., heat inactivated, degradative agent. A physical parameter, e.g., size, of the modified and control molecules are then determined. They can be determined by a physical method, e.g., by polyacrylamide gel electrophoresis or a sizing column, to assess whether the molecule has maintained its original length, or assessed functionally. Alternatively, Northern blot analysis can be used to assay the length of an unlabeled modified molecule.

A functional assay can also be used to evaluate the candidate agent. A functional assay can be applied initially or after an earlier non-functional assay, (e.g., assay for resistance to degradation) to determine if the modification alters the ability of the molecule to activate PRR activity. For example, a cell, e.g., a mammalian cell, such as a mouse or human cell, can be co-transfected with a plasmid encoding a PRR, and a candidate nucleic acid molecule. In one embodiment, the candidate oligonucleotide molecule can be assayed for its ability to activate RIG-I ATPase activity and/or IFN production, as described elsewhere herein.

RNA may be produced enzymatically or by partial/total organic synthesis, any modified ribonucleotide can be introduced by in vitro enzymatic or organic synthesis. In one embodiment, the nucleic acid molecule of the invention is prepared chemically. Methods of synthesizing RNA molecules are known in the art, in particular, the chemical synthesis methods as described in Verma and Eckstein (1998) Annul Rev. Biochem. 67:99-134.

In one embodiment, the nucleic acid molecule is synthesized either in vivo, in situ, or in vitro. Endogenous RNA polymerase of the cell may mediate transcription in vivo or in situ, or cloned RNA polymerase can be used for transcription in vivo or in vitro. For transcription from a transgene in vivo or an expression construct, a regulatory region (e.g., promoter, enhancer, silencer, splice donor and acceptor, polyadenylation) may be used to transcribe the RNA molecule. Activity of the RNA molecule may be induced by specific transcription in an organ, tissue, or cell type; stimulation of an environmental condition (e.g., infection, stress, temperature, chemical inducers); and/or engineering transcription at a developmental stage or age.

Methods

The invention includes methods of introducing nucleic acids, vectors, and host cells to a subject. Physical methods of introducing nucleic acids include injection of a solution containing the nucleic acid molecule, bombardment by particles covered by the nucleic acid molecule, soaking the cell or organism in a solution of the nucleic acid molecule, or electroporation of cell membranes in the presence of the nucleic acid molecule. A viral construct packaged into a viral particle would accomplish both efficient introduction of an expression construct into the cell and transcription of RNA encoded by the expression construct. Other methods known in the art for introducing nucleic acids to cells may be used, such as lipid-mediated carrier transport, chemical-mediated transport, such as calcium phosphate, and the like. Thus the nucleic acid may be introduced along with components that perform one or more of the following activities: enhance nucleic acid uptake by the cell, stabilize the duplex, or other-wise increase activity of the nucleic acid molecule.

Methods of introducing nucleic acids into a cell are known in the art. The nucleic acid molecule of the invention can be readily introduced into a host cell, e.g., mammalian, bacterial, yeast, or insect cell by any method in the art. For example, the nucleic acid molecule can be transferred into a host cell by physical, chemical, or biological means.

Physical methods for introducing a nucleic acid into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al. (2001, Molecular Cloning: A Laboratory Manual, Cold Spring Harbor Laboratory, New York).

Biological methods for introducing a nucleic acid into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a nucleic acid into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

In certain instances, the nucleic acid is delivered via a polymeric delivery vehicle. For example, the nucleic acid molecule may be complexed with a polymer based micelle, capsule, microparticle, nanoparticle, or the like. The complex may then be contacted to a cell in vivo, in vitro, or ex vivo, thereby introducing the nucleic acid molecule to the cell. Exemplary polymeric delivery systems are well known in the art (see for example U.S. Pat. No. 6,013,240). Polymeric delivery reagents are commercially available, including exemplary reagents obtainable from Polyplus-transfection Inc (New York, N.Y.).

In the case where a non-viral delivery system is utilized, an exemplary delivery vehicle is a liposome. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Lipids suitable for use can be obtained from commercial sources. For example, dimyristyl phosphatidylcholine ("DMPC") can be obtained from Sigma, St. Louis, Mo.; dicetyl phosphate ("DCP") can be obtained from K & K Laboratories (Plainview, N.Y.); cholesterol ("Choi") can be obtained from Calbiochem-Behring; dimyristyl phosphatidylglycerol ("DMPG") and other lipids may be obtained from Avanti Polar Lipids, Inc. (Birmingham, Ala.). Stock solutions of lipids in chloroform or chloroform/methanol can be stored at about −20° C. Chloroform is used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., 1991 Glycobiology 5: 505-10). However, compositions that have different structures in solution than the normal vesicular structure are also encompassed. For example, the lipids may assume a micellar structure or merely exist as nonuniform aggregates of lipid molecules. Also contemplated are lipofectamine-nucleic acid complexes.

Regardless of the method used to introduce the nucleic acid molecule into a host cell or otherwise expose a cell to the molecule of the present invention, in order to confirm the presence of the nucleic acid in the host cell, a variety of assays may be performed. Such assays include, for example, "molecular biological" assays well known to those of skill in the art, such as Southern and Northern blotting, RT-PCR and PCR.

The nucleic acid molecule of the invention may be directly introduced into the cell (i.e., intracellularly); or introduced extracellularly into a cavity, interstitial space, into the circulation of an organism, introduced orally, or may be introduced by bathing a cell or organism in a solution containing the nucleic acid molecule. Vascular or extravascular circulation, the blood or lymph system, and the cerebrospinal fluid are sites where the nucleic acid molecule may be introduced.

Alternatively, vectors, e.g., transgenes encoding the nucleic acid molecule of the invention can be engineered into a host cell or transgenic animal using art recognized techniques.

The present invention provides a method of inducing an IFN response in a cell. For example, in certain embodiments, the method induces a type I IFN response. Type I IFNs include, for example IFN-α, IFN-β, IFN-κ, IFN-δ, IFN-ε, IFN-τ, IFN-ω, and IFN-ζ.

The present application provides the in vitro use of the nucleic acid molecule of the invention. In particular, the present application provides the use of at least one nucleic acid molecule for inducing an IFN response, including for example a type I IFN response, in vitro. The present application also provides the use of at least one nucleic acid molecule for inducing apoptosis of a tumor cell in vitro.

The present invention provides an in vitro method for stimulating an IFN response, including for example a type I IFN response in a cell comprising contacting a cell with at least one nucleic acid molecule of the invention.

The cells may express a PRR endogenously and/or exogenously from an exogenous nucleic acid (RNA or DNA). The exogenous DNA may be a plasmid DNA, a viral vector, or a portion thereof. The exogenous DNA may be integrated into the genome of the cell or may exist extra-chromosomally. The cells include, but are not limited to, primary immune cells, primary non-immune cells, and cell lines. Immune cells include, but are not limited to, peripheral blood mononuclear cells (PBMC), plasmacytoid dendritric cells (PDC), myeloid dendritic cells (MDC), macrophages, monocytes, B cells, natural killer cells, granulocytes, CD4+ T cells, CD8+ T cells, and NKT cells. Non-immune cells include, but are not limited to, fibroblasts, endothelial cells, epithelial cells, and tumor cells. Cell lines may be derived from immune cells or non-immune cells.

The present invention provides an in vitro method for inducing apoptosis of a tumor cell, comprising contacting a tumor cell with at least one nucleic acid molecule of the invention. The tumor cell may be a primary tumor cell freshly isolated from a vertebrate animal having a tumor or a tumor cell line.

In one embodiment, the present invention provides for both prophylactic and therapeutic methods of inducing an IFN response a patient. It is understood that "treatment" or "treating" as used herein, is defined as the application or administration of a therapeutic agent (e.g., a nucleic acid molecule) to a patient, or application or administration of a therapeutic agent to an isolated tissue or cell line from a patient, who has a disease or disorder, a symptom of disease or disorder or a predisposition toward a disease or disorder, with the purpose to cure, heal, alleviate, relieve, alter, remedy, ameliorate, improve or affect the disease or disorder, the symptoms of the disease or disorder, or the predisposition toward disease.

In one embodiment, the present application provides the in vivo use of the nucleic acid molecule of the invention. In one embodiment, the present application provides at least one nucleic acid molecule of the invention for inducing an IFN response, including for example a type I IFN response, in a vertebrate animal, in particular, a mammal. The present application further provides at least one nucleic acid molecule of the invention for inducing apoptosis of a tumor cell in a vertebrate animal, in particular, a mammal. The present application additionally provides at least one nucleic acid molecule of the invention for preventing and/or treating a disease and/or disorder in a vertebrate animal, in particular, a mammal, in medical and/or veterinary practice. The invention also provides at least one nucleic acid molecule of the invention for use as a vaccine adjuvant.

In certain embodiments, the composition and method of the invention are used as a research tool. For example, the nucleic acid molecule may be used in vitro or in vivo, to evaluate the effects of increased PRR activity and/or increased IFN production.

Furthermore, the present application provides the use of at least one nucleic acid molecule of the invention for the preparation of a pharmaceutical composition for inducing an IFN response, including for example a type I IFN response in a vertebrate animal, in particular, a mammal. The present application further provides the use of at least one nucleic acid molecule of the invention for the preparation of a pharmaceutical composition for inducing apoptosis of a tumor cell in a vertebrate animal, in particular, a mammal. The present application additionally provides the use of at least one nucleic acid molecule of the invention for the preparation of a pharmaceutical composition for preventing and/or treating a disease and/or disorder in a vertebrate animal, in particular, a mammal, in medical and/or veterinary practice.

The present invention encompasses the use of the nucleic acid molecule to prevent and/or treat any disease, disorder, or condition in which inducing IFN production would be beneficial. For example, increased IFN production, by way of the nucleic acid molecule of the invention, may be beneficial to prevent or treat a wide variety of disorders, including, but not limited to, bacterial infection, viral infection, parasitic infection, cancer, immune disorders, respiratory disorders, and the like.

Infections include, but are not limited to, viral infections, bacterial infections, anthrax, parasitic infections, fungal infections and prion infection.

Viral infections include, but are not limited to, infections by hepatitis C, hepatitis B, influenza virus, herpes simplex virus (HSV), human immunodeficiency virus (HIV), respiratory syncytial virus (RSV), vesicular stomatitis virus (VSV), cytomegalovirus (CMV), poliovirus, encephalomyocarditis virus (EMCV), human papillomavirus (HPV) and smallpox virus. In one embodiment, the infection is an upper respiratory tract infection caused by viruses and/or bacteria, in particular, flu, more specifically, bird flu.

Bacterial infections include, but are not limited to, infections by streptococci, staphylococci, *E. Coli*, and *pseudomonas*. In one embodiment, the bacterial infection is an intracellular bacterial infection which is an infection by an intracellular bacterium such as mycobacteria (tuberculosis), *chlamydia, mycoplasma, listeria*, and an facultative intracelluar bacterium such as *Staphylococcus aureus*.

Parasitic infections include, but are not limited to, worm infections, in particular, intestinal worm infection, microeukaryotes, and vector-borne diseases, including for example Leishmaniasis.

In a preferred embodiment, the infection is a viral infection or an intracellular bacterial infection. In a more preferred embodiment, the infection is a viral infection by hepatitis C, hepatitis B, influenza virus, RSV, HPV, HSV1, HSV2, and CMV.

Tumors include both benign and malignant tumors (i.e., cancer). Cancers include, but are not limited to biliary tract cancer, brain cancer, breast cancer, cervical cancer, choriocarcinoma, colon cancer, endometrial cancer, esophageal cancer, gastric cancer, intraepithelial neoplasm, leukemia, lymphoma, liver cancer, lung cancer, melanoma, myelomas, neuroblastoma, oral cancer, ovarian cancer, pancreatic cancer, prostate cancer, rectal cancer, sarcoma, skin cancer, testicular cancer, thyroid cancer and renal cancer.

In certain embodiments, the cancer is selected from hairy cell leukemia, chronic myelogenous leukemia, cutaneous T-cell leukemia, chronic myeloid leukemia, non-Hodgkin's lymphoma, multiple myeloma, follicular lymphoma, malignant melanoma, squamous cell carcinoma, renal cell carcinoma, prostate carcinoma, bladder cell carcinoma, breast carcinoma, ovarian carcinoma, non-small cell lung cancer, small cell lung cancer, hepatocellular carcinoma, basaliom, colon carcinoma, cervical dysplasia, and Kaposi's sarcoma (AIDS-related and non-AIDS related).

Immune disorders include, but are not limited to, allergies, autoimmune disorders, and immunodeficiencies.

Allergies include, but are not limited to, respiratory allergies, contact allergies and food allergies.

Autoimmune diseases include, but are not limited to, multiple sclerosis, diabetes mellitus, arthritis (including rheumatoid arthritis, juvenile rheumatoid arthritis, osteoarthritis, psoriatic arthritis), encephalomyelitis, myasthenia gravis, systemic lupus erythematosis, autoimmune thyroiditis, dermatisis (including atopic dermatitis and eczematous dermatitis), psoriasis, Siogren's Syndrome, Crohn's disease, aphthous ulcer, iritis, conjunctivitis, keratoconjunctivitis, ulcerative colitis, asthma, allergic asthma, cutaneous lupus erythematosus, scleroderma, vaginitis, proctitis, drug eruptions, leprosy reversal reactions, erythema nodosum leprosum, autoimmune uveitis, allergic encephalomyelitis, acute necrotizing hemorrhagic encephalopathy, idiopathic bilateral progressive sensorineural hearing loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Graves' disease, sarcoidosis, primary biliary cirrhosis, uveitis posterior, and interstitial lung fibrosis.

Immunodeficiencies include, but are not limited to, spontaneous immunodeficiency, acquired immunodeficiency (including AIDS), drug-induced immunodeficiency or immunosuppression (such as that induced by immunosuppressants used in transplantation and chemotherapeutic agents used for treating cancer), and immunosuppression caused by chronic hemodialysis, trauma or surgical procedures.

Respiratory disorders include, but are not limited to, acute lung injury (ALI), acute respiratory distress syndrome (ARDS), asthma, chronic obstructive pulmonary disease (COPD), obstructive sleep apnea (OSA), idiopathic pulmonary fibrosis (IPF), tuberculosis, pulmonary hypertension, pleural effusion, and lung cancer.

In certain embodiments, the nucleic acid molecule of the invention is used in combination with one or more pharmaceutically active agents such as immunostimulatory agents, anti-viral agents, antibiotics, anti-fungal agents, anti-parasitic agents, anti-tumor agents, cytokines, chemokines, growth factors, anti-angiogenic factors, chemotherapeutic agents, antibodies and gene silencing agents. Preferably, the pharmaceutically active agent is selected from the group consisting of an immunostimulatory agent, an anti-bacterial agent, an anti-viral agent, an anti-inflammatory agent and an anti-tumor agent. The more than one pharmaceutically active agents may be of the same or different category.

In one embodiment, the nucleic acid molecule of the invention is used in combination with an antigen, an anti-viral vaccine, an anti-bacterial vaccine, and/or an anti-tumor vaccine, wherein the vaccine can be prophylactic and/or therapeutic. The nucleic acid molecule can serve as an adjuvant.

In another embodiment, the nucleic acid is used in combination with retinoic acid and/or type I IFN (IFN-α and/or IFN-β). Without being bound by any theory, retinoid acid, IFN-α and/or IFN-β are capable of sensitizing cells for IFN-β production, possibly through the upregulation of PRR expression.

In other embodiments, the nucleic acid molecule of the invention is for use in combination with one or more prophylactic and/or therapeutic treatments of diseases and/or disorders such as infection, tumor, and immune disorders. The treatments may be pharmacological and/or physical (e.g., surgery, radiation).

Vertebrate animals include, but are not limited to, fish, amphibians, birds, and mammals. Mammals include, but are not limited to, rats, mice, cats, dogs, horses, sheep, cattle, cows, pigs, rabbits, non-human primates, and humans. In a preferred embodiment, the mammal is human.

In one embodiment, the nucleic acid molecule of the invention is used in combination with an anti-viral vaccine, wherein the vaccine can be prophylactic and/or therapeutic.

Administration/Dosing

The regimen of administration may affect what constitutes an effective amount. The therapeutic formulations may be administered to the subject either prior to or after a diagnosis of disease. Further, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the compositions of the present invention to a subject, preferably a mammal, more preferably a human, may be carried out using known procedures, at dosages and for periods of time effective to prevent or treat disease. An effective amount of the therapeutic compound necessary to achieve a therapeutic effect may vary according to factors such as the activity of the particular compound employed; the time of administration; the rate of excretion of the compound; the duration of the treatment; other drugs, compounds or materials used in combination with the compound; the state of the disease or disorder, age, sex, weight, condition, general health and prior medical history of the subject being treated, and like factors well-known in the medical arts. Dosage regimens may be adjusted to provide the optimum therapeutic response. For example, several divided doses may be administered daily or the dose may be proportionally reduced as indicated by the exigencies of the therapeutic situation. A non-limiting example of an effective dose range for a therapeutic compound of the invention is from about 1 and 5,000 mg/kg of body weight/per day. One of ordinary skill in the art would be able to study the relevant factors and make the determination regarding the effective amount of the therapeutic compound without undue experimentation.

The compound may be administered to a subject as frequently as several times daily, or it may be administered less frequently, such as once a day, once a week, once every two weeks, once a month, or even less frequently, such as once every several months or even once a year or less. It is understood that the amount of compound dosed per day may be administered, in non-limiting examples, every day, every other day, every 2 days, every 3 days, every 4 days, or every 5 days. For example, with every other day administration, a 5 mg per day dose may be initiated on Monday with a first subsequent 5 mg per day dose administered on Wednesday, a second subsequent 5 mg per day dose administered on Friday, and so on. The frequency of the dose will be readily apparent to the skilled artisan and will depend upon any number of factors, such as, but not limited to, the type and severity of the disease being treated, the type and age of the animal, etc.

Actual dosage levels of the active ingredients in the pharmaceutical compositions of this invention may be varied so as to obtain an amount of the active ingredient that is effective to achieve the desired therapeutic response for a particular subject, composition, and mode of administration, without being toxic to the subject.

A medical doctor, e.g., physician or veterinarian, having ordinary skill in the art may readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In particular embodiments, it is especially advantageous to formulate the compound in dosage unit form for ease of administration and uniformity of dosage. Dosage unit form as used herein refers to physically discrete units suited as unitary dosages for the subjects to be treated; each unit containing a predetermined quantity of therapeutic compound calculated to produce the desired therapeutic effect in association with the required pharmaceutical vehicle. The dosage unit forms of the invention are dictated by and directly dependent on (a) the unique characteristics of the therapeutic compound and the particular therapeutic effect to be achieved, and (b) the limitations inherent in the art of compounding/formulating such a therapeutic compound for the treatment of a disease in a subject.

In one embodiment, the compositions of the invention are administered to the subject in dosages that range from one to five times per day or more. In another embodiment, the compositions of the invention are administered to the subject in range of dosages that include, but are not limited to, once every day, every two, days, every three days to once a week, and once every two weeks. It will be readily apparent to one skilled in the art that the frequency of administration of the various combination compositions of the invention will vary from subject to subject depending on many factors including, but not limited to, age, disease or disorder to be treated, gender, overall health, and other factors. Thus, the invention should not be construed to be limited to any particular dosage regime and the precise dosage and composition to be administered to any subject will be determined by the attending physical taking all other factors about the subject into account.

Compounds of the invention for administration may be in the range of from about 1 mg to about 10,000 mg, about 20 mg to about 9,500 mg, about 40 mg to about 9,000 mg, about 75 mg to about 8,500 mg, about 150 mg to about 7,500 mg, about 200 mg to about 7,000 mg, about 3050 mg to about 6,000 mg, about 500 mg to about 5,000 mg, about 750 mg to about 4,000 mg, about 1 mg to about 3,000 mg, about 10 mg to about 2,500 mg, about 20 mg to about 2,000 mg, about 25 mg to about 1,500 mg, about 50 mg to about 1,000 mg, about 75 mg to about 900 mg, about 100 mg to about 800 mg, about 250 mg to about 750 mg, about 300 mg to about 600 mg, about 400 mg to about 500 mg, and any and all whole or partial increments therebetween.

In some embodiments, the dose of a compound of the invention is from about 1 mg and about 2,500 mg. In some embodiments, a dose of a compound of the invention used in compositions described herein is less than about 10,000 mg, or less than about 8,000 mg, or less than about 6,000 mg, or less than about 5,000 mg, or less than about 3,000 mg, or less than about 2,000 mg, or less than about 1,000 mg, or less than about 500 mg, or less than about 200 mg, or less than about 50 mg. Similarly, in some embodiments, a dose of a second compound (i.e., a drug used for treating the same or another disease as that treated by the compositions of the invention) as described herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof.

In one embodiment, the present invention is directed to a packaged pharmaceutical composition comprising a container holding a therapeutically effective amount of a compound or conjugate of the invention, alone or in combination with a second pharmaceutical agent; and instructions for using the compound or conjugate to treat, prevent, or reduce one or more symptoms of a disease in a subject.

The term "container" includes any receptacle for holding the pharmaceutical composition. For example, in one embodiment, the container is the packaging that contains the pharmaceutical composition. In other embodiments, the container is not the packaging that contains the pharmaceutical composition, i.e., the container is a receptacle, such as a box or vial that contains the packaged pharmaceutical composition or unpackaged pharmaceutical composition and the instructions for use of the pharmaceutical composition. Moreover, packaging techniques are well known in the art. It should be understood that the instructions for use of the pharmaceutical composition may be contained on the packaging containing the pharmaceutical composition, and as such the instructions form an increased functional relationship to the packaged product. However, it should be understood that the instructions may contain information pertaining to the compound's ability to perform its intended function, e.g., treating or preventing a disease in a subject, or delivering an imaging or diagnostic agent to a subject.

Pharmaceutical Compositions

The present invention provides a pharmaceutical composition comprising at least one nucleic acid molecule of the present invention and a pharmaceutically acceptable carrier. The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Although the description of pharmaceutical compositions provided herein are principally directed to pharmaceutical compositions which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as non-human primates, cattle, pigs, horses, sheep, cats, and dogs.

Pharmaceutical compositions that are useful in the methods of the invention may be prepared, packaged, or sold in formulations suitable for ophthalmic, oral, rectal, vaginal, parenteral, topical, pulmonary, intranasal, buccal, or another route of administration. Other contemplated formulations include projected nanoparticles, liposomal preparations, resealed erythrocytes containing the active ingredient, and immunologically-based formulations.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

In addition to the active ingredient, a pharmaceutical composition of the invention may further comprise one or more additional pharmaceutically active agents. Other active agents useful in the present invention include anti-inflammatories, including corticosteroids, and immunosuppressants, chemotherapeutic agents, antibiotics, antivirals, antifungals, and the like.

Controlled- or sustained-release formulations of a pharmaceutical composition of the invention may be made using conventional technology, using for example proteins equipped with pH sensitive domains or protease-cleavable fragments. In some cases, the dosage forms to be used can be provided as slow or controlled-release of one or more active ingredients therein using, for example, hydroxypropylmethyl cellulose, other polymer matrices, gels, permeable membranes, osmotic systems, multilayer coatings, microparticles, liposomes, or microspheres or a combination thereof to provide the desired release profile in varying proportions. Suitable controlled-release formulations known to those of ordinary skill in the art, including those described herein, can be readily selected for use with the pharmaceutical compositions of the invention. Thus, single unit dosage forms suitable for oral administration, such as tablets, capsules, gel-caps, and caplets, which are adapted for controlled-release are encompassed by the present invention.

Most controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased subject compliance. In addition, controlled-release formulations can be used to affect the time of onset of action or other characteristics, such as blood level of the drug, and thus can affect the occurrence of side effects.

Most controlled-release formulations are designed to initially release an amount of drug that promptly produces the desired therapeutic effect, and gradually and continually release of other amounts of drug to maintain this level of therapeutic effect over an extended period of time. In order to maintain this constant level of drug in the body, the drug must be released from the dosage form at a rate that will replace the amount of drug being metabolized and excreted from the body.

Controlled-release of an active ingredient can be stimulated by various inducers, for example pH, temperature, enzymes, water or other physiological conditions or compounds. The term "controlled-release component" in the context of the present invention is defined herein as a compound or compounds, including, but not limited to, polymers, polymer matrices, gels, permeable membranes, liposomes, or microspheres or a combination thereof that facilitates the controlled-release of the active ingredient.

In certain embodiments, the formulations of the present invention may be, but are not limited to, short-term, rapid-offset, as well as controlled, for example, sustained release, delayed release and pulsatile release formulations.

The term sustained release is used in its conventional sense to refer to a drug formulation that provides for gradual release of a drug over an extended period of time, and that may, although not necessarily, result in substantially constant blood levels of a drug over an extended time period. The period of time may be as long as a month or more and should be a release that is longer that the same amount of agent administered in bolus form.

For sustained release, the compounds may be formulated with a suitable polymer or hydrophobic material that provides sustained release properties to the compounds. As such, the compounds for use the method of the invention may be administered in the form of microparticles, for example, by injection or in the form of wafers or discs by implantation.

In a preferred embodiment of the invention, the compounds of the invention are administered to a subject, alone or in combination with another pharmaceutical agent, using a sustained release formulation.

The term delayed release is used herein in its conventional sense to refer to a drug formulation that provides for an initial release of the drug after some delay following drug administration and that mat, although not necessarily, includes a delay of from about 10 minutes up to about 12 hours.

The term pulsatile release is used herein in its conventional sense to refer to a drug formulation that provides release of the drug in such a way as to produce pulsed plasma profiles of the drug after drug administration.

The term immediate release is used in its conventional sense to refer to a drug formulation that provides for release of the drug immediately after drug administration.

As used herein, short-term refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes and any or all whole or partial increments thereof after drug administration after drug administration.

As used herein, rapid-offset refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes, and any and all whole or partial increments thereof after drug administration.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in Remington's Pharmaceutical Sciences (1985, Genaro, ed., Mack Publishing Co., Easton, Pa.), which is incorporated herein by reference.

The composition of the invention may comprise a preservative from about 0.005% to 2.0% by total weight of the composition. The preservative is used to prevent spoilage in the case of exposure to contaminants in the environment. Examples of preservatives useful in accordance with the invention included but are not limited to those selected from the group consisting of benzyl alcohol, sorbic acid, parabens, imidurea and combinations thereof. A particularly preferred preservative is a combination of about 0.5% to 2.0% benzyl alcohol and 0.05% to 0.5% sorbic acid.

The composition preferably includes an anti-oxidant and a chelating agent that inhibits the degradation of the compound. Preferred antioxidants for some compounds are BHT, BHA, alpha-tocopherol and ascorbic acid in the preferred range of about 0.01% to 0.3% and more preferably BHT in the range of 0.03% to 0.1% by weight by total weight of the composition. Preferably, the chelating agent is present in an amount of from 0.01% to 0.5% by weight by total weight of the composition. Particularly preferred chelating agents include edetate salts (e.g. disodium edetate) and citric acid in the weight range of about 0.01% to 0.20% and more preferably in the range of 0.02% to 0.10% by weight by total weight of the composition. The chelating agent is useful for chelating metal ions in the composition that may be detrimental to the shelf life of the formulation. While BHT and disodium edetate are the particularly preferred antioxidant and chelating agent respectively for some compounds, other suitable and equivalent antioxidants and chelating agents may be substituted therefore as would be known to those skilled in the art.

Liquid suspensions may be prepared using conventional methods to achieve suspension of the active ingredient in an aqueous or oily vehicle. Aqueous vehicles include, for example, water, and isotonic saline. Oily vehicles include, for example, almond oil, oily esters, ethyl alcohol, vegetable oils such as *arachis*, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, hydroxypropylmethylcellulose. Known dispersing or wetting agents include, but are not limited to, naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g., polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin, and acacia. Known preservatives include, but are not limited to, methyl, ethyl, or n-propyl-para-hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

Liquid solutions of the active ingredient in aqueous or oily solvents may be prepared in substantially the same manner as liquid suspensions, the primary difference being that the active ingredient is dissolved, rather than suspended in the solvent. As used herein, an "oily" liquid is one which comprises a carbon-containing liquid molecule and which exhibits a less polar character than water. Liquid solutions of the pharmaceutical composition of the invention may comprise each of the components described with regard to liquid suspensions, it being understood that suspending agents will not necessarily aid dissolution of the active ingredient in the solvent. Aqueous solvents include, for example, water, and isotonic saline. Oily solvents include, for example, almond oil, oily esters, ethyl alcohol, vegetable oils such as *arachis*, olive, sesame, or coconut oil, fractionated vegetable oils, and mineral oils such as liquid paraffin.

Powdered and granular formulations of a pharmaceutical preparation of the invention may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of dispersing or wetting agent, a suspending agent, and a preservative. Additional excipients, such as fillers and sweetening, flavoring, or coloring agents, may also be included in these formulations.

A pharmaceutical composition of the invention may also be prepared, packaged, or sold in the form of oil-in-water emulsion or a water-in-oil emulsion. The oily phase may be a vegetable oil such as olive or *arachis* oil, a mineral oil such as liquid paraffin, or a combination of these. Such compositions may further comprise one or more emulsifying agents such as naturally occurring gums such as gum acacia or gum tragacanth, naturally-occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions may also contain additional ingredients including, for example, sweetening or flavoring agents.

Methods for impregnating or coating a material with a chemical composition are known in the art, and include, but are not limited to methods of depositing or binding a chemical composition onto a surface, methods of incorporating a chemical composition into the structure of a material during the synthesis of the material (i.e., such as with a physiologically degradable material), and methods of absorbing an aqueous or oily solution or suspension into an absorbent material, with or without subsequent drying.

Routes of administration of any of the compositions of the invention include oral, nasal, rectal, parenteral, sublingual, transdermal, transmucosal (e.g., sublingual, lingual, (trans) buccal, (trans)urethral, vaginal (e.g., trans- and perivaginally), (intra)nasal, and (trans)rectal), intravesical, intrapulmonary, intraduodenal, intragastrical, intrathecal, subcutaneous, intramuscular, intradermal, intra-arterial, intravenous, intrabronchial, inhalation, and topical administration.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

For oral application, particularly suitable are tablets, dragees, liquids, drops, suppositories, or capsules, caplets and gelcaps. Other formulations suitable for oral administration include, but are not limited to, a powdered or granular formulation, an aqueous or oily suspension, an aqueous or oily solution, a paste, a gel, toothpaste, a mouthwash, a coating, an oral rinse, or an emulsion. The compositions intended for oral use may be prepared according to any method known in the art and such compositions may contain one or more agents selected from the group consisting of inert, non-toxic pharmaceutically excipients that are suitable for the manufacture of tablets. Such excipients include, for example an inert diluent such as lactose; granulating and disintegrating agents such as cornstarch; binding agents such as starch; and lubricating agents such as magnesium stearate.

Tablets may be non-coated or they may be coated using known methods to achieve delayed disintegration in the gastrointestinal tract of a subject, thereby providing sustained release and absorption of the active ingredient. By way of example, a material such as glyceryl monostearate or glyceryl distearate may be used to coat tablets. Further by way of example, tablets may be coated using methods described in U.S. Pat. Nos. 4,256,108; 4,160,452; and 4,265,874 to form osmotically controlled release tablets. Tablets may further comprise a sweetening agent, a flavoring agent, a coloring agent, a preservative, or some combination of these in order to provide for pharmaceutically elegant and palatable preparation.

Hard capsules comprising the active ingredient may be made using a physiologically degradable composition, such as gelatin. Such hard capsules comprise the active ingredient, and may further comprise additional ingredients including, for example, an inert solid diluent such as calcium carbonate, calcium phosphate, or kaolin.

Soft gelatin capsules comprising the active ingredient may be made using a physiologically degradable composition, such as gelatin. Such soft capsules comprise the active ingredient, which may be mixed with water or an oil medium such as peanut oil, liquid paraffin, or olive oil.

For oral administration, the compositions of the invention may be in the form of tablets or capsules prepared by conventional means with pharmaceutically acceptable excipients such as binding agents; fillers; lubricants; disintegrates; or wetting agents. If desired, the tablets may be coated using suitable methods and coating materials such as OPADRY™ film coating systems available from Colorcon, West Point, Pa. (e.g., OPADRY™ OY Type, OYC Type, Organic Enteric OY—P Type, Aqueous Enteric OY-A Type, OY-PM Type and OPADRY™ White, 32K18400).

Liquid preparation for oral administration may be in the form of solutions, syrups or suspensions. The liquid preparations may be prepared by conventional means with pharmaceutically acceptable additives such as suspending agents (e.g., sorbitol syrup, methyl cellulose or hydrogenated edible fats); emulsifying agent (e.g., lecithin or acacia); non-aqueous vehicles (e.g., almond oil, oily esters or ethyl alcohol); and preservatives (e.g., methyl or propyl p-hydroxy benzoates or sorbic acid). Liquid formulations of a pharmaceutical composition of the invention which are suitable for oral administration may be prepared, packaged, and sold either in liquid form or in the form of a dry product intended for reconstitution with water or another suitable vehicle prior to use.

A tablet comprising the active ingredient may, for example, be made by compressing or molding the active ingredient, optionally with one or more additional ingredients. Compressed tablets may be prepared by compressing, in a suitable device, the active ingredient in a free-flowing form such as a powder or granular preparation, optionally mixed with one or more of a binder, a lubricant, an excipient, a surface active agent, and a dispersing agent. Molded tablets may be made by molding, in a suitable device, a mixture of the active ingredient, a pharmaceutically acceptable carrier, and at least sufficient liquid to moisten the mixture. Pharmaceutically acceptable excipients used in the manufacture of tablets include, but are not limited to, inert diluents, granulating and disintegrating agents, binding agents, and lubricating agents. Known dispersing agents include, but are not limited to, potato starch and sodium starch glycollate. Known surface-active agents include, but are not limited to, sodium lauryl sulphate. Known diluents include, but are not limited to, calcium carbonate, sodium carbonate, lactose, microcrystalline cellulose, calcium phosphate, calcium hydrogen phosphate, and sodium phosphate. Known granulating and disintegrating agents include, but are not limited to, corn starch and alginic acid. Known binding agents include, but are not limited to, gelatin, acacia, pre-gelatinized maize starch, polyvinylpyrrolidone, and hydroxypropyl methylcellulose. Known lubricating agents include, but are not limited to, magnesium stearate, stearic acid, silica, and talc.

Granulating techniques are well known in the pharmaceutical art for modifying starting powders or other particulate materials of an active ingredient. The powders are typically mixed with a binder material into larger permanent free-flowing agglomerates or granules referred to as a "granulation." For example, solvent-using "wet" granulation processes are generally characterized in that the powders are combined with a binder material and moistened with water or an organic solvent under conditions resulting in the formation of a wet granulated mass from which the solvent must then be evaporated.

Melt granulation generally consists in the use of materials that are solid or semi-solid at room temperature (i.e. having a relatively low softening or melting point range) to promote granulation of powdered or other materials, essentially in the absence of added water or other liquid solvents. The low melting solids, when heated to a temperature in the melting point range, liquefy to act as a binder or granulating medium. The liquefied solid spreads itself over the surface of powdered materials with which it is contacted, and on cooling, forms a solid granulated mass in which the initial materials are bound together. The resulting melt granulation may then be provided to a tablet press or be encapsulated for preparing the oral dosage form. Melt granulation improves the dissolution rate and bioavailability of an active (i.e. drug) by forming a solid dispersion or solid solution.

U.S. Pat. No. 5,169,645 discloses directly compressible wax-containing granules having improved flow properties. The granules are obtained when waxes are admixed in the melt with certain flow improving additives, followed by cooling and granulation of the admixture. In certain embodiments, only the wax itself melts in the melt combination of the wax(es) and additives(s), and in other cases both the wax(es) and the additives(s) will melt.

The present invention also includes a multi-layer tablet comprising a layer providing for the delayed release of one or more compounds of the invention, and a further layer providing for the immediate release of a medication for treatment of a disease. Using a wax/pH-sensitive polymer mix, a gastric insoluble composition may be obtained in which the active ingredient is entrapped, ensuring its delayed release.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, intraocular, intravitreal, subcutaneous, intraperitoneal, intramuscular, intrasternal injection, intratumoral, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e. powder or granular) form for reconstitution with a suitable vehicle (e.g. sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt.

An obstacle for topical administration of pharmaceuticals is the stratum corneum layer of the epidermis. The stratum corneum is a highly resistant layer comprised of protein, cholesterol, sphingolipids, free fatty acids and various other lipids, and includes cornified and living cells. One of the factors that limit the penetration rate (flux) of a compound through the stratum corneum is the amount of the active substance that can be loaded or applied onto the skin surface. The greater the amount of active substance which is applied per unit of area of the skin, the greater the concentration gradient between the skin surface and the lower layers of the skin, and in turn the greater the diffusion force of the active substance through the skin. Therefore, a formulation containing a greater concentration of the active substance is more likely to result in penetration of the active substance through the skin, and more of it, and at a more consistent rate, than a formulation having a lesser concentration, all other things being equal.

Formulations suitable for topical administration include, but are not limited to, liquid or semi-liquid preparations such as liniments, lotions, oil-in-water or water-in-oil emulsions such as creams, ointments or pastes, and solutions or suspensions. Topically administrable formulations may, for example, comprise from about 1% to about 10% (w/w) active ingredient, although the concentration of the active ingredient may be as high as the solubility limit of the active ingredient in the solvent. Formulations for topical administration may further comprise one or more of the additional ingredients described herein.

Enhancers of permeation may be used. These materials increase the rate of penetration of drugs across the skin. Typical enhancers in the art include ethanol, glycerol monolaurate, PGML (polyethylene glycol monolaurate), dimethylsulfoxide, and the like. Other enhancers include oleic acid, oleyl alcohol, ethoxydiglycol, laurocapram, alkanecarboxylic acids, dimethylsulfoxide, polar lipids, or N-methyl-2-pyrrolidone.

One acceptable vehicle for topical delivery of some of the compositions of the invention may contain liposomes. The composition of the liposomes and their use are known in the art (for example, see U.S. Pat. No. 6,323,219).

In alternative embodiments, the topically active pharmaceutical composition may be optionally combined with other ingredients such as adjuvants, anti-oxidants, chelating agents, surfactants, foaming agents, wetting agents, emulsifying agents, viscosifiers, buffering agents, preservatives, and the like. In another embodiment, a permeation or penetration enhancer is included in the composition and is effective in improving the percutaneous penetration of the active ingredient into and through the stratum corneum with respect to a composition lacking the permeation enhancer. Various permeation enhancers, including oleic acid, oleyl alcohol, ethoxydiglycol, laurocapram, alkanecarboxylic acids, dimethylsulfoxide, polar lipids, or N-methyl-2-pyrrolidone, are known to those of skill in the art. In another aspect, the composition may further comprise a hydrotropic agent, which functions to increase disorder in the structure of the stratum corneum, and thus allows increased transport across the stratum corneum. Various hydrotropic agents, such as isopropyl alcohol, propylene glycol, or sodium xylene sulfonate, are known to those of skill in the art.

The topically active pharmaceutical composition should be applied in an amount effective to affect desired changes. As used herein "amount effective" shall mean an amount sufficient to cover the region of skin surface where a change is desired. An active compound should be present in the amount of from about 0.0001% to about 15% by weight volume of the composition. More preferable, it should be present in an amount from about 0.0005% to about 5% of the composition; most preferably, it should be present in an amount of from about 0.001% to about 1% of the composition. Such compounds may be synthetically- or naturally derived.

A pharmaceutical composition of the invention may be prepared, packaged, or sold in a formulation suitable for rectal administration. Such a composition may be in the form of, for example, a suppository, a retention enema preparation, and a solution for rectal or colonic irrigation.

Suppository formulations may be made by combining the active ingredient with a non-irritating pharmaceutically acceptable excipient which is solid at ordinary room temperature (i.e., about 20° C.) and which is liquid at the rectal temperature of the subject (i.e., about 37° C. in a healthy human). Suitable pharmaceutically acceptable excipients include, but are not limited to, cocoa butter, polyethylene glycols, and various glycerides. Suppository formulations may further comprise various additional ingredients including, but not limited to, antioxidants, and preservatives.

Retention enema preparations or solutions for rectal or colonic irrigation may be made by combining the active ingredient with a pharmaceutically acceptable liquid carrier. As is well known in the art, enema preparations may be administered using, and may be packaged within, a delivery device adapted to the rectal anatomy of the subject. Enema preparations may further comprise various additional ingredients including, but not limited to, antioxidants, and preservatives.

A pharmaceutical composition of the invention may be prepared, packaged, or sold in a formulation suitable for vaginal administration. With respect to the vaginal or perivaginal administration of the compounds of the invention, dosage forms may include vaginal suppositories, creams, ointments, liquid formulations, pessaries, tampons, gels, pastes, foams or sprays. The suppository, solution, cream, ointment, liquid formulation, pessary, tampon, gel, paste, foam or spray for vaginal or perivaginal delivery comprises a therapeutically effective amount of the selected active agent and one or more conventional nontoxic carriers suitable for vaginal or perivaginal drug administration. The vaginal or perivaginal forms of the present invention may be manufactured using conventional processes as disclosed in Remington: The Science and Practice of Pharmacy, supra (see also drug formulations as adapted in U.S. Pat. Nos. 6,515,198; 6,500,822; 6,417,186; 6,416,779; 6,376,500; 6,355,641; 6,258,819; 6,172,062; and 6,086,909). The vaginal or perivaginal dosage unit may be fabricated to disintegrate rapidly or over a period of several hours. The time period for complete disintegration may be in the range of from about 10 minutes to about 6 hours, e.g., less than about 3 hours.

Methods for impregnating or coating a material with a chemical composition are known in the art, and include, but are not limited to methods of depositing or binding a chemical composition onto a surface, methods of incorporating a chemical composition into the structure of a material during the synthesis of the material (i.e., such as with a physiologically degradable material), and methods of absorbing an aqueous or oily solution or suspension into an absorbent material, with or without subsequent drying.

Douche preparations or solutions for vaginal irrigation may be made by combining the active ingredient with a pharmaceutically acceptable liquid carrier. As is well known in the art, douche preparations may be administered using, and may be packaged within, a delivery device adapted to the vaginal anatomy of the subject.

Douche preparations may further comprise various additional ingredients including, but not limited to, antioxidants, antibiotics, antifungal agents, and preservatives.

A pharmaceutical composition of the invention may be prepared, packaged, or sold in a formulation suitable for pulmonary administration via the buccal cavity. Such a formulation may comprise dry particles which comprise the active ingredient and which have a diameter in the range from about 0.5 to about 7 nanometers, and preferably from about 1 to about 6 nanometers. Such compositions are conveniently in the form of dry powders for administration using a device comprising a dry powder reservoir to which a stream of propellant may be directed to disperse the powder or using a self-propelling solvent/powder-dispensing container such as a device comprising the active ingredient dissolved or suspended in a low-boiling propellant in a sealed container. Preferably, such powders comprise particles wherein at least 98% of the particles by weight have a diameter greater than 0.5 nanometers and at least 95% of the particles by number have a diameter less than 7 nanometers. More preferably, at least 95% of the particles by weight have a diameter greater than 1 nanometer and at least 90% of the particles by number have a diameter less than 6 nanometers. Dry powder compositions preferably include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic or solid anionic surfactant or a solid diluent (preferably having a particle size of the same order as particles comprising the active ingredient).

Pharmaceutical compositions of the invention formulated for pulmonary delivery may also provide the active ingredient in the form of droplets of a solution or suspension. Such formulations may be prepared, packaged, or sold as aqueous or dilute alcoholic solutions or suspensions, optionally sterile, comprising the active ingredient, and may conveniently be administered using any nebulization or atomization device. Such formulations may further comprise one or more additional ingredients including, but not limited to, a flavoring agent such as saccharin sodium, a volatile oil, a buffering agent, a surface active agent, or a preservative such as methylhydroxybenzoate. The droplets provided by this route of administration preferably have an average diameter in the range from about 0.1 to about 200 nanometers.

The formulations described herein as being useful for pulmonary delivery are also useful for intranasal delivery of a pharmaceutical composition of the invention.

Another formulation suitable for intranasal administration is a coarse powder comprising the active ingredient and having an average particle from about 0.2 to 500 micrometers. Such a formulation is administered in the manner in which snuff is taken i.e. by rapid inhalation through the nasal passage from a container of the powder held close to the nares.

Formulations suitable for nasal administration may, for example, comprise from about as little as 0.1% (w/w) and as much as 100% (w/w) of the active ingredient, and may further comprise one or more of the additional ingredients described herein.

A pharmaceutical composition of the invention may be prepared, packaged, or sold in a formulation suitable for buccal administration. Such formulations may, for example, be in the form of tablets or lozenges made using conventional methods, and may, for example, 0.1 to 20% (w/w) active ingredient, the balance comprising an orally dissolvable or degradable composition and, optionally, one or more of the additional ingredients described herein. Alternately, formulations suitable for buccal administration may comprise a powder or an aerosolized or atomized solution or suspension comprising the active ingredient. Such powdered, aerosolized, or aerosolized formulations, when dispersed, preferably have an average particle or droplet size in the range from about 0.1 to about 200 nanometers, and may further comprise one or more of the additional ingredients described herein.

Diagnosing and Screening Assay

In one embodiment, the present invention provides compositions and methods for detecting a PRR in a biological sample and diagnosing a disease or disorder associated with a PRR in a subject. In one embodiment, the present invention provides compositions and methods for diagnosing a disease or disorder associated with an IFN response in a subject.

In one embodiment, the method comprises assessing the presence and/or activity of a PRR in a subject using a nucleic acid molecule of the invention. For example, a cell or biological sample is isolated from the subject and the cell or biological sample is contacted with a nucleic acid molecule of the invention to determine whether the cell or biological sample is able to induce an IFN response.

In one embodiment, the assay comprises using a nucleic acid molecule of the invention to determine whether a cell or a biological sample comprising a cell exhibits PRR activity. For example, the cell or biological sample is contacted with a nucleic acid molecule of the invention to determine whether the cell or biological sample is able to induce an IFN response. Without wishing to be bound by any particular theory, a cell or biological sample that induces an IFN response in the presence of a nucleic acid molecule of the invention compared to a cell or biological sample that does not induce an IFN response means that the cell or biological sample that induces an IFN response comprises a PRR.

In one aspect, the present invention is directed to a screening assay to identify compounds that stimulate or inhibit PRR activity. In another aspect, the present invention is directed to a screening assay to identify compounds that induce or inhibit an IFN response.

In one embodiment, the invention provides a method of screening a library of agents to identify an agent that induces or inhibits an IFN response. For example, the method comprises contacting a cell or biological sample with a nucleic acid molecule of the invention in the presence or absence of a test compound. Without wishing to be bound by any particular theory, a cell or biological sample that induces an IFN response or increases an IFN response in the presence of a nucleic molecule of the invention and the test agent identifies the test agent as one that induces IFN response. For example, in one embodiment, the level of IFN response in the presence of a nucleic acid molecule of the invention is a baseline level for an IFN response. An agent that induces an IFN response is identified when the level of IFN response is increased when the cell or biological sample is combined with the nucleic acid molecule of the invention and the test agent. On the other hand, an agent that inhibits an IFN response is identified when the level of IFN response is decreased when the cell or biological sample is combined with the nucleic acid molecule of the invention and the test agent.

The test agents can be obtained using any of the numerous approaches in combinatorial-library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds (Lam et al., 1997, Anticancer Drug Des. 12:45).

Examples of methods for the synthesis of molecular libraries can be found in the art, for example, in: DeWitt et al., 1993, Proc. Natl. Acad. USA 90:6909; Erb et al., 1994, Proc. Natl. Acad. Sci. USA 91:11422; Zuckermann et al., 1994, J. Med. Chem. 37:2678; Cho et al., 1993, Science 261:1303; Carrell et al., 1994, Angew. Chem. Int. Ed. Engl. 33:2059; Carell et al., 1994, Angew. Chem. Int. Ed. Engl. 33:2061; and Gallop et al., 1994, J. Med. Chem. 37:1233.

Libraries of compounds may be presented in solution (e.g., Houghten, 1992, Biotechniques 13:412-421), or on beads (Lam, 1991, Nature 354:82-84), chips (Fodor, 1993, Nature 364:555-556), bacteria (Ladner U.S. Pat. No. 5,223,409), spores (Ladner U.S. Pat. No. '409), plasmids (Cull et al., 1992, Proc. Natl. Acad. Sci. USA 89:1865-1869) or on phage (Scott and Smith, 1990, Science 249:386-390; Devlin, 1990, Science 249:404-406; Cwirla et al., 1990, Proc. Natl. Acad. Sci. USA 87:6378-6382; Felici, 1991, J. Mol. Biol. 222:301-310; and Ladner supra).

In situations where "high-throughput" modalities are preferred, it is typical that new chemical entities with useful properties are generated by identifying a chemical compound (called a "lead compound") with some desirable property or activity, creating variants of the lead compound, and evaluating the property and activity of those variant compounds. The current trend is to shorten the time scale for all aspects of drug discovery.

In one embodiment, high throughput screening methods involve providing a library containing a large number of compounds (candidate compounds) potentially having the desired activity. Such "combinatorial chemical libraries" are then screened in one or more assays, as described herein, to identify those library members (particular chemical species or subclasses) that display a desired characteristic activity. The compounds thus identified can serve as conventional "lead compounds" or can themselves be used as potential or actual therapeutics.

Kits

The invention also provides kits stimulating PRR activity and inducing an IFN response, as elsewhere described herein. In one embodiment, the kit includes a composition comprising a nucleic acid molecule, as elsewhere described herein, and instructions for its use. The instructions will generally include information about the use of the compositions in the kit for the stimulation of PRR activity. The instructions may be printed directly on a container inside the kit (when present), or as a label applied to the container, or as a separate sheet, pamphlet, card, or folder supplied in or with the container.

The invention also provides kits for the treatment or prevention of a disease, disorder, or condition in which IFN production would be beneficial. In one embodiment, the kit includes a composition (e.g. a pharmaceutical composition) comprising a nucleic acid molecule, as elsewhere described herein, and instructions for its use. The instructions will generally include information about the use of the compositions in the kit for the treatment or prevention of a disease or disorder or symptoms thereof. The instructions may be printed directly on a container inside the kit (when present), or as a label applied to the container, or as a separate sheet, pamphlet, card, or folder supplied in or with the container.

EXPERIMENTAL EXAMPLES

The invention is further described in detail by reference to the following experimental examples. These examples are provided for purposes of illustration only, and are not intended to be limiting unless so specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

Example 1: Defining the Functional Determinants for RNA Surveillance by RIG-I Retinoic acid inducible gene-I (RIG-I) is an intracellular RNA sensor that engages the innate immune machinery in response to infection by a variety of RNA viruses. The pathogen associated molecular pattern (PAMP) for RIG-I is generally defined as duplex RNA containing a 5'triphosphate moiety. The results presented herein demonstrate an additional two distinct conformations of a RIG-I: dsRNA complex that illustrate the structural dynamics of RNA duplex recognition and its relevance to the catalytic ATPase activity of RIG-I. Reported herein, are the crystal structure of distinct conformations of a RIG-I:dsRNA complex, which shows that HEL2i-mediated scanning allows RIG-I to sense the length of RNA targets. While the Hel1-RNA-CTD form a rigid sandwich-like fold, the Hel2i domain of RIG-I exhibits a high degree of flexibility in surveying the substrate, making contacts with six to ten base pairs of the RNA. To elucidate the significance of this scanning mechanism, the ability of RNA duplexes to stimulate the ATP hydrolysis activity of RIG-I and elicit an interferon response was measured. Short RNA hairpins and palindromic duplexes of lengths between 8 and 30 base pairs and with 5'ends of either a hydroxyl group or triphosphate were tested. The results presented herein provide biophysical and in vivo evidence that RIG-I activity is stimulated exclusively via interaction with the 5' ends of duplex substrates, whereas interactions with internal "stem" regions of these substrates are likely non-productive. The data indicate RIG-I surveys and recognizes 5' ends of dsRNA as a monomer without RNA-induced oligomerization. These results reveal that the minimal functional unit of the RIG-I:RNA complex is a monomer that binds at the terminus of a duplex RNA substrate. This behaviour is markedly different from the RIG-I paralog melanoma differentiation-associated gene 5 (MDA5), which forms cooperative filaments.

The materials and methods employed in these experiments are now described.

Cloning, Expression, and Purification

Purification of the full-length human RIG-I and the N-terminal CARDs (residues 1-229) deletion construct was described previously (Luo et al., 2011, Cell 147:409-422; Luo et al., 2012b, Structure, 20:1983-1988). Briefly, the constructs were cloned into the pET-SUMO vector (Invitrogen) and transformed into Rosetta II(DE3) *E. coli* cells (Novagen). The proteins were expressed in LB media upon the addition of 0.5 mM isopropyl-β-D-thiogalactopyranoside (IPTG) and grown at 18° C. overnight for 20 hours. The cells were then lysed with a microfluidizer at 15,000 psi, clarified by centrifugation, and purified by batch binding with Ni-NTA beads (Qiagen). After collection and elution from Biorad polyprep columns, the RIG-I constructs were concentrated on a HiTrap Heparin HP column (GE Healthcare) and gel filtered over a HiPrep 16/60 Superdex 200 column (GE Healthcare) in buffer containing 25 mM Hepes, pH 7.4, 150 mM NaCl, 5% glycerol, 5 mM β-ME. RIG-I preparations were concentrated to between 5-10 mg/mL with a 50 k MW cutoff Amicon centrifugal concentrator (Millipore), and concentrations were determined spectrophotometrically, using the extinction coefficients of $\varepsilon=99,700$ M-1 cm-1 for full length RIG-I and an $\varepsilon=60,280$ M-1 cm-1 for the RIG-I (ΔCARDs:1-229)N-terminal deletion construct. The extinction coefficients were calculated theoretically from the RIG-I sequence and guanidinium chloride denaturation of protein preparations. The RIG-I preparations were flash frozen with liquid nitrogen and stored at −80° C.

RNA Synthesis and Transcription

The 5'OH 'GC' Palindromic RNA Duplexes were Made by RNA Synthesis (Sigma). The 5'ppp 'GC' palindromic RNA duplexes were made by in vitro runoff transcription using DNA templates (SIGMA) with a 2'O-methyl modification on the penultimate nucleotide of the template strand (Kao et al., 1999, RNA, 5: 1268-72). The LMW poly I:C was ordered from Invivogen. The 2'O-methyl modification on the penultimate nucleotide of the template strand prevents T7 terminal transferase activity as previously described (Kao et al., 1999, RNA, 5: 1268-72). Incorporation of 2'-OMe modifications within the DNA template prevents addition of +1 and +2 nucleotides by T7 RNA polymerase and results in transcription of RNA molecules with defined, uniform 3'-ends, which is obviously essential for studies of RIG-I binding and stimulation. All synthesized and transcribed RNA constructs were purified on 20% denaturing polyacrylamide gels. LMW polyI:C (Invivogen) was dissolved in buffer containing Hepes (pH 7.4), 150 mM NaCl, 5% glycerol, 5 mM BME to a final concentration of 10 mg/ml. 500 μl of this solution was loaded on an analytical 10.300 Superdex 200 Column (GE) and eluted at 0.25 ml/min while collecting 1 ml fractions. Concentrations were determined spectrophotometrically.

All hairpin RNAs were purified by 8M urea PAGE. After gel extraction, the re-annealing step was performed at low RNA concentrations by heating the RNA at 96° C. for 2 mins and rapidly cooling on ice. It is notable that these hairpins are stabilized by a terminal UUCG tetraloop, which is known to promote exclusive hairpin formation by short duplexes, including those as short as four base-pairs (Cheong et al, 1990, Nature, 346: 680-682; Nozinovic et al, 2010, Nucleic Acids Res, 38: 683-694).

Crystallization, Data Collection, Structure Determination and Refinement.

The crystallization and data collection of RIG-I (ΔCARDs:1-229) binary and ternary complexes were performed as described previously, with modifications (Luo et al., 2011, Cell 147:409-422). Structures were determined by molecular replacement using pdb:2ykg as a model. Briefly, the RIG-I (ΔCARDs:1-229) complex with 5'OH-GC10 duplex was preassembled by incubating at a protein:RNA molar ratio of 1:1.5 on ice for 1 hour and then purified with a HiPrep 16/60 Superdex 200 column (GE Healthcare). The crystals of the binary complex of RIG-I (ΔCARDs:1-229): 5'OH-GC10 were grown at 13° C. by mixing equal volumes of precipitating solution (0.1 M Bicine, pH 9.0, 22.5% polyethylene glycol 6,000) and RIG-I (ΔCARDs:1-229): 5'OH-GC10 complex (2-3 mg ml$^{-1}$) using the sitting drop method. The crystals grew into needle clusters within a week and were harvested within two weeks. The crystals were soaked in a cryoprotecting solution containing 0.1 M Bicine, pH 9.0, 30% polyethylene glycol 6,000 for 12 hours before being flash frozen with liquid nitrogen. To grow the crystals of the ternary complex of RIG-I (ΔCARDs:1-229):5'OH-GC10:ADP-Mg$^2$, the binary complex of RIG-I (ΔCARDs: 1-229):5'OH-GC10 was first incubated with 2.5 mM ADP and 2.5 mM MgCl$_2$ at 2-3 mg ml$^{-1}$ for half an hour to one hour on ice, mixed with equal volumes of precipitating solution (0.1 M Bicine, pH 9.0, 26-28% polyethylene glycol 6,000) and then grown at 13° C. Crystals also grew into needle clusters within three days and were harvested within two weeks. Crystals were soaked in a cryoprotecting solution containing 0.1 M Bicine, pH 9.0, 30% polyethylene glycol 6,000 briefly before being flash frozen with liquid nitrogen. Diffraction intensities were recorded at NE-CAT beamline ID-24 at the Advanced Photon Source (Argonne National Laboratory, Argonne, Ill.). Integration, scaling and merging of the intensities were carried out by using the programs XDS (Kabsch, 2010, Acta Crystallogr D Biol Crystallogr 66:125-132) and SCALA (Evans, 2006, Acta Crystallogr D Biol Crystallogr 62:72-82).

Initial attempts to use the structure of RIG-I (ΔCARDs: 1-229): 5'OH-GC10 (PDB: 2ykg) as search model for molecular replacement were not successful. Rather, successful phasing was accomplished through molecular replacement by using the subgroups (HEL1: aa 236-455, HEL2-HEL2i: aa 456-793, CTD: aa 794-925, and dsRNA) of RIG-I (ΔCARDs:1-229): 5'OH-GC10 (PDB: 2ykg) as search models in Phaser (McCoy, 2007, Acta Crystallogr D Biol Crystallogr 63:32-41). Refinement cycles were carried out using Phenix Refine (Adams et al., 2010, Acta Crystallogr D Biol Crystallogr 66:213-221) and REFMAC5 (Murshudov et al., 1997, Acta Crystallogr D Biol Crystallogr 53:240-255) with four TLS (translation, liberation, screw-rotation displacement) groups (HEL1: aa 236-455, HEL2-HEL2i: aa 456-793, CTD: aa 794-925, and dsRNA). Refinement cycles were interspersed with model rebuilding using Coot (Emsley and Cowtan, 2004, Acta Crystallogr D Biol Crystallogr 60:2126-2132). The quality of the structures was analyzed with PROCHECK (Laskowski et al., 1993, J Appl Cryst 26:283-291). A summary of the data collection and structure refinement statistics is given in Table 1. During the crystallographic studies, it was noticed that crystals with RIG-I:dsRNA captured in the conformation 1, the binary complex of RIG-I and 5'OH-GC10, is always associated with the longest c axis (225.1 Å) of the unit cells (conformation 2, 219.8 Å and conformation 3, 207.8 Å), Figures were prepared by using the program Pymol (DeLano, 2002, The PyMOL User's Manual: DeLano Scientific, Palo Alto, Calif., USA),

TABLE 1

Crystallographic and structure refinement statistics.

| Structure | RIG-I (ΔCARDs 1-229): GC10 (Conformation 1) | RIG-I (ΔCARDs 1-229): GC10:SO$_4$ (Conformation 2)$^b$ | RIG-I (ΔCARDs 1-229): GC10:ADP-Mg (Conformation 3) |
|---|---|---|---|
| Data collection | | | |
| Space group | P2$_1$2$_1$2$_1$ | P2$_1$2$_1$2$_1$ | P2$_1$2$_1$2$_1$ |
| Cell dimensions (Å) | 48.5, 78.0, 225.1 | 47.6, 76.2, 219.8 | 48.3, 76.1, 207.8 |
| Resolution (Å) | 48.5-2.8 (2.9-2.8)$^a$ | 47.6-2.5 (2.6-2.5) | 48.3-2.5 (2.6-2.5) |
| R merge (%) | 6.4 (70.6) | 7.5 (62.3) | 6.4 (57.3) |
| I/σ | 16.2 (1.8) | 14.5 (1.5) | 11.4 (1.9) |
| Completeness (%) | 99.3 (98.6) | 93.8 (58.8) | 98.1 (98.9) |
| Redundancy | 5.0 (4.8) | 5.0 (2.2) | 3.4 (3.1) |
| Refinement | | | |
| Resolution (Å) | 25.0-2.8 | 45.0-2.5 | 25.0-2.5 |
| R work/R free (%) | 22.2/27.9 | 22.4/27.5 | 22.9/28.8 |
| No. atoms | 5,380 | 5,517 | 5,369 |
| Protein | 4,947 | 4,985 | 4,857 |
| RNA/ADP-Mg$^{2+}$ | 424 | 424 | 424/28 |
| Water | 9 | 99 | 60 |
| B-factors (Å$^2$) | 74.7 | 57.9 | 66.2 |
| Protein | 75.1 | 58.1 | 66.4 |

TABLE 1-continued

Crystallographic and structure refinement statistics.

| Structure | RIG-I (ΔCARDs 1-229): GC10 (Conformation 1) | RIG-I (ΔCARDs 1-229): GC10:SO$_4$ (Conformation 2)[b] | RIG-I (ΔCARDs 1-229): GC10:ADP-Mg (Conformation 3) |
|---|---|---|---|
| Ligand | 71.7 | 65.7 | 70.2 |
| Solvent | 74.6 | 48.7 | 51.9 |
| Ramachandran analysis | | | |
| Favored | 86.3 | 94.2 | 89.1 |
| Additionally allowed | 12.8 | 4.8 | 10.4 |
| Outliers | 0.9 | 1.0 | 0.5 |
| R.m.s. deviations | | | |
| Bond lengths (Å) | 0.099 | 0.086 | 0.097 |
| Bond angles (°) | 1.6 | 1.3 | 1.5 |
| PDB ID | 3zd6 | 2ykg | 3zd7 |

[a]Statistics for the highest resolution shell is shown in parenthesis
[b]Reference data taken from RCSB Protein Data Bank (ID: 2YKG) (Luo et al., 2011, Cell 147:409-422)

Analytical Ultracentrifugation-Sedimentation (SV) Experiments

Mixtures were loaded into SV chambers and equilibrated at 20° C. for 1 h before beginning the experiment. The sedimentation of the RIG-I:hairpin complexes was monitored by absorbance at 260 nm, and the protein without RNA was monitored by absorbance at 280 nm.

Full length RIG-I protein was mixed with 5'ppp10L, 5'ppp20L, 5'ppp30L and 5'pppGC22 RNAs at a ratio of 4.5 μM RIG-I:1.5 μM RNA (or RIG-I alone) in 450 μl aliquots in buffer containing 25 mM HEPES pH 7.4, 150 mM NaCl, 2 mM MgCl2, and 5 mM BME. The SV experiments were run at 40,000 rpm in a Beckman Optima XL-I analytical ultracentrifuge. Partial specific volumes for RIG-I and RIG-I:RNA complexes and buffer density and viscosity parameters were calculated in SEDNTERP. Data analyses were performed in SEDFIT (Schuck, 2000, Biophysical Journal, 78: 1609-1619; Schuck et al, 2002, Biophysical Journal, 82: 1096-1111).

NADH-Coupled ATPase Experiments

ATPase activity of RIG-I was measured with the NADH-coupled ATPase assay adapted from previously described protocols (Luo et al., 2011, Cell 147:409-422). Experiments were set up in 50 μl reaction volumes in 96 well format using Corning clear half-area flat bottom plates (#3695). Each 50 μl reaction contained 10 μl of 5×NADH enzyme buffer (1 mM NADH, 100 U of lactate dehydrogenase/mL, 500 U/mL of pyruvate kinase/mL, and 2.5 mM phosphoenolpyruvate), 5-10 nM of RIG-I, 5 μl of varying amounts of either RNA or ATP, and a remaining volume of 25 mM 3-(N-morpholino)propanesulfonic acid (MOPS) pH 7.4, 150 mM KCl, 2 mM DTT, and 0.1% Triton X-100. The rate of ATP hydrolysis was indirectly determined by monitoring the loss of NADH by reading the absorbance at 340 nm using a Biotek Synergy H1 plate reader. For both the Km,ATP and the Km,RNA experiments, RIG-I and the RNA constructs were allowed to equilibrate for at least 2 hours before addition of ATP. Detergent was required to record reproducible ATPase rates in the 96-well Corning clear bottom plates, especially at low concentrations of RIG-I. The initial velocities (v0) at various RNA concentrations were plotted and fit to the following quadratic solution to the Briggs-Haldane equation:

$$y = y_0 + (amp) * \frac{[M_t] + [S_t] + K_m - \sqrt{([M_t] + [S_t] + K_m)^2 - 4[M_t][S_t]}}{2[M_t]} \quad (1)$$

[$M_t$] is the total protein concentration, [$S_t$] is the total [RNA], $y_0$ is 135 the basal activity, amp is the kcat (minus the basal activity), and Km is the apparent Michaelis constant for substrate activation. The $y_0$ was constrained to the average basal activity from the entire set of 0 nM RNA, 5 mM ATP wells. The initial velocities ($v_0$) at various ATP concentrations were plotted and fit to the hyperbolic form of the above equation:

$$y = \frac{(amp) * [ATP]}{K_M + [ATP]} \quad (2)$$

Figure 3:
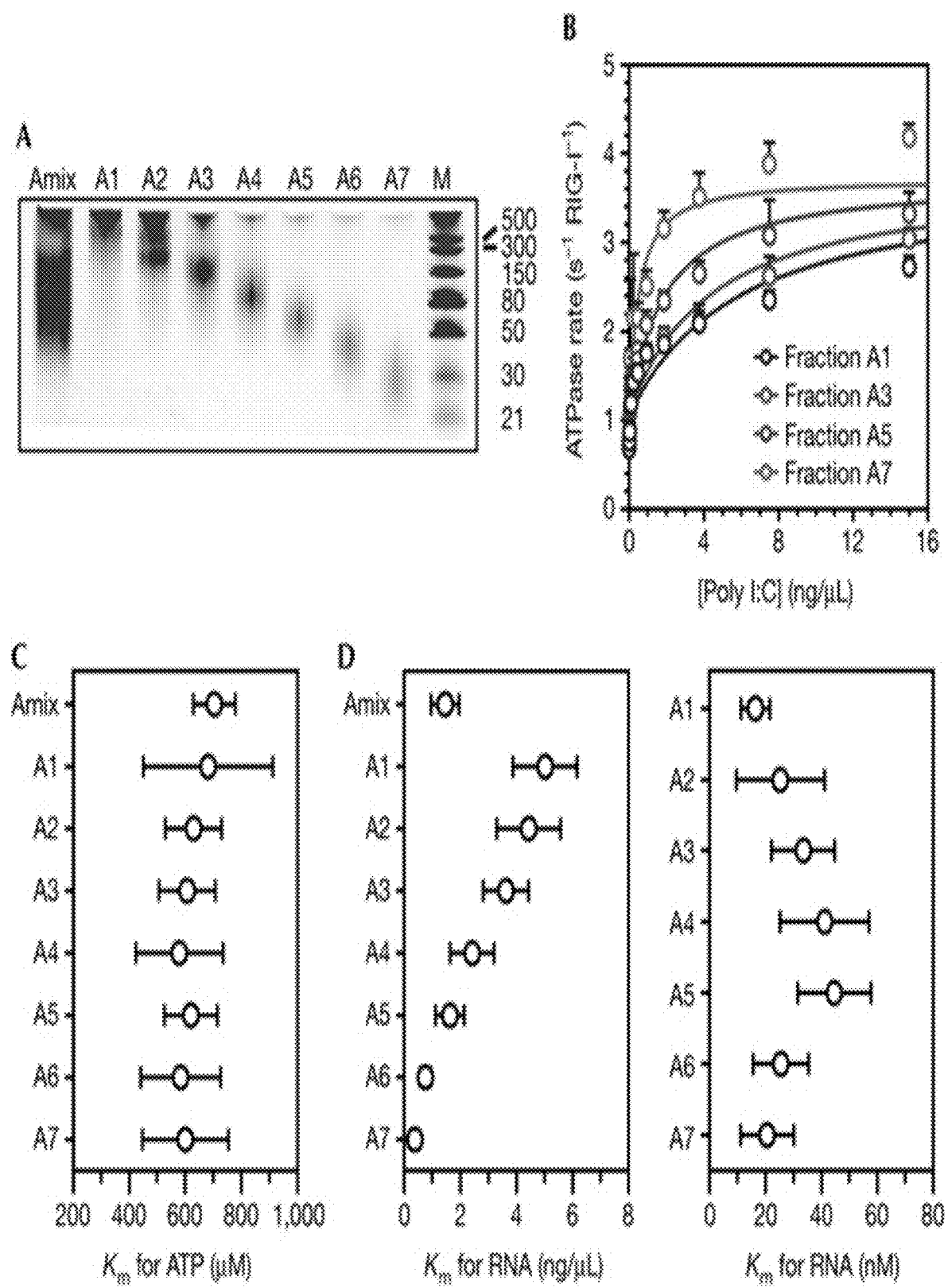
FIG. 3, comprising

For the ATPase experiments in which the ATP concentration was varied, the RNA concentration were held at 500 nM for the short RNA duplexes (FIG. 4 and FIG. 7), 500 ng/μL for the poly I:C experiments (FIG. 6), and 15 ng/μL for the poly I:C fractions (FIG. 3). Although 15 ng/μL was suboptimal for the longer polyIC fractions, it was the highest that could be managed for all of the fractions from a single gel filtration experiment. One row from a 96 well plate constituted a single experiment with the following 12 ATP solutions in μM (final concentrations listed) derived from a two-thirds dilution series: 0, 30.2, 50.4, 84.0, 140.0, 233.3, 388.8, 648, 1080, 1800, 3000, and 5000.

Figure 6:
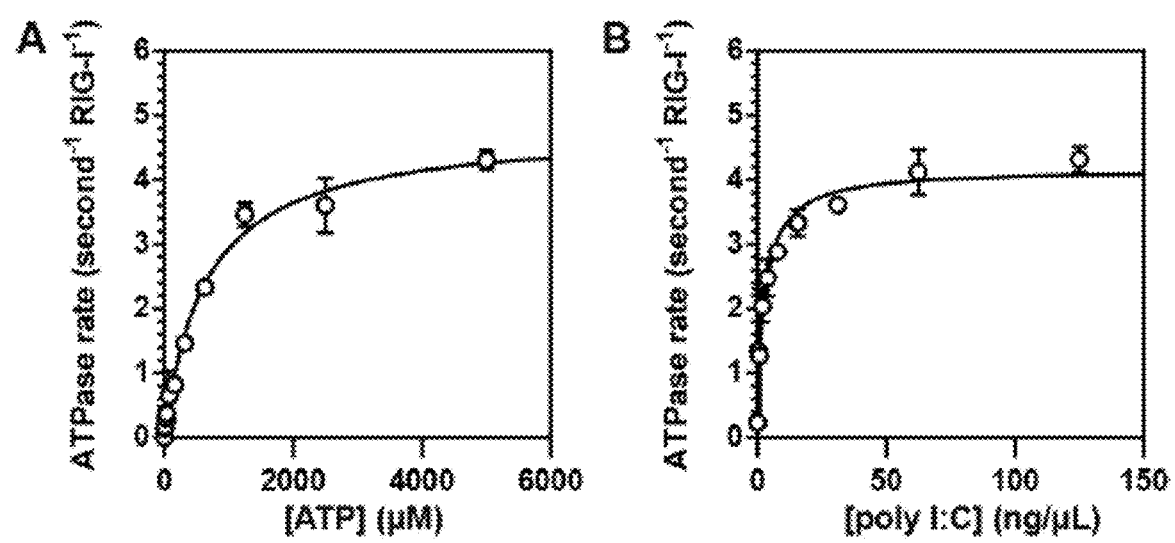
FIG. 6, comprising
Figure 7:
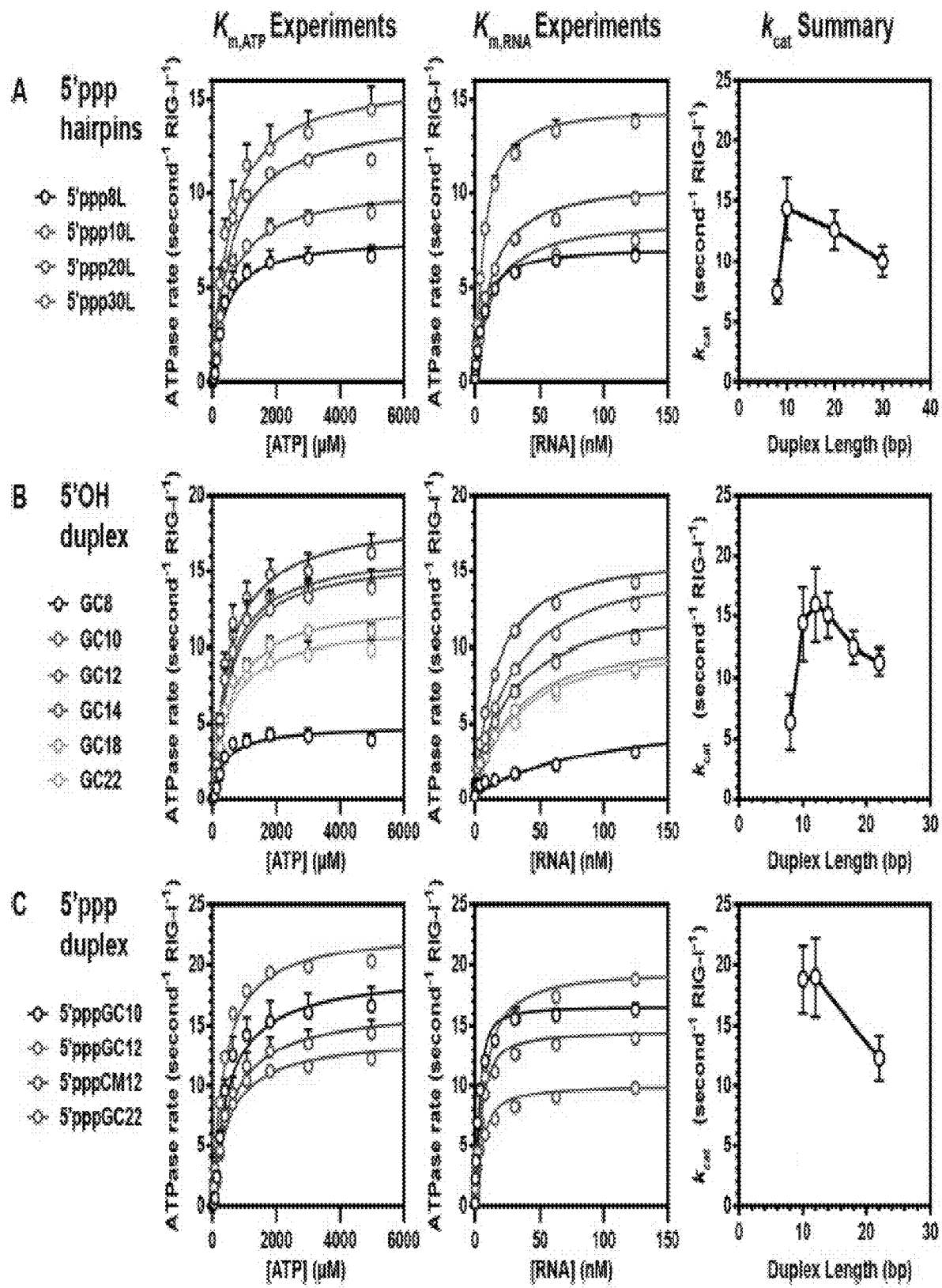
FIG. 7A through FIG. 7C, depicts the results of $K_{m,ATP}$ and $K_{m,RNA}$ ATPase experiments on short duplex RNA. ATPase activity of RIG-I stimulated by various length RNAs including 5'triphosphorylated hairpins, 5'hydroxyl duplexes, and 5'triphosphorylated duplexes. The $K_{m,ATP}$ of RIG-I (10 nM enzyme) stimulated by each RNA was measured by varying the ATP concentrations ranging from 0 to 5 mM at 500 nM RNA. The $K_{m,RNA}$ of RIG-I (5 nM enzyme) stimulated by each RNA was measured by varying the RNA concentrations ranging from 0 to 500 nM at 5 mM ATP. A small basal activity (0 nM RNA) is measured for RIG-I of less than 1 per second. Error bars for the Km,ATP and Km,RNA experiments report the standard error of the mean from 4 experiments. The last column of graphs plots the average kcat values calculated from Briggs-Haldane fits from both the $K_{m,ATP}$ and $K_{m,RNA}$ experiments. Error bars for the kcat summary report the standard deviation measured across 6 experiments, in which each experiment was comprised of an averaged duplicate dataset for each RNA or ATP concentration.

For the ATPase experiments in which the RNA concentration was varied, the ATP concentration was held at 5 mM, approximately 10-fold above the Km,ATP measured for each RNA fraction. One row from a 96-well plate constituted a single experiment with the following 12 RNA concentrations in nM (or ng/μl for poly I:C, final concentrations listed) from a two-fold dilution series: 0, 0.5, 1.0, 2.0, 3.9, 7.8, 15.6, 31.2, 62.5, 125, 250, and 500 (FIG. 4, FIG. 6, and FIG. 7). For the gel filtered poly I:C fractions the following 12 RNA concentrations in 155 ng/μL (final concentrations listed) were used from a two-fold dilution series: 0, 0.01, 0.03, 0.06, 0.12, 0.23, 0.47, 0.94, 1.88, 3.75, 7.50, 15 (FIG. 3). In order to calculate the nM amounts of each poly I:C fraction for FIG. 3D, the following estimates were made for the duplex lengths of fractions A1-A7 respectively based on the semi-denaturing polyacrylamide gel and molecular weight standards shown in FIG. 3A: 500, 360, 180, 90, 60, 40, and 25. The nM concentration ranges used for the analysis of the gel filtered poly I:C fractions is shown in Table 3.

Cell Culture IFN-β Response.

293T cells transfected with pUNO-RIG-I, pRL-TK and IFN-β/firefly luciferase reporter were seeded at 15,000 cells per well, with each well containing 5 µl of Lyovec (Invivogen) and either RNA hairpin or poly I:C. For luciferase measurements, the Promega Dual Luciferase Reporter assay system was used to quantify the cellular levels of firefly and Renilla luciferase.

Batches of 293T cells were grown to 70-80% confluency in 10 cm dishes in Dulbecco's Modified Eagle Medium (DMEM; Invitrogen) containing 10% heat-inactivated fetal calf serum (Hyclone) and non-essential amino acids (Invitrogen). For RIG-I transfections of 10 cm dishes of 293T cells, one 800 µl aliquot of Opti-MEM containing 4 µg of pUNO-RIG-I, 1 µg of pRL-TK, and 5 µg of an IFN-β/Firefly luciferase reporter plasmid was mixed with a second 800 µl aliquot of Opti-MEM containing 50 µl of lipofectamine. After 45 minutes, the 1.6 mL aliquot was diluted four-fold with Opti-MEM and then added to a 10 cm dish of 293T cells. The transfection was allowed to proceed for 6-8 hours, and then 10 mL of fresh DMEM was added to the plate. The cells were split twice into 15 cm dishes over the course of three days in 3 µg/µL blasticidin, and then used for transfections in 96 well plates containing RNA hairpins or poly I:C fractions.

The 293T cells, in DMEM without blasticidin, and transfected with pUNO-RIG-I, pRL-TK, and IFN-β/Firefly luciferase reporter, were seeded at 15,000 cells per well, with each well containing 5 µl of Lyovec (Invivogen), and the following final concentrations of 5'ppp RNA hairpin in nM: 39.1, 78.1, 156.3, 312.5, 625 or the following final concentrations of poly I:C in total ng per well: 15.6, 31.3, 62.5, 125, 250, 500. In each experiment, the RNA hairpin or poly I:C was tested three times at each concentration (or total RNA amount). Luminescence measurements were assayed between 16-24 hours after stimulation by the RNA.

For luciferase measurements, the Promega Dual Luciferase Reporter assay system was used to quantitate the cellular levels of firefly and Renilla luciferase. Briefly, media was aspirated from each 96 well plate and replaced with 60 µL, of passive lysis buffer. After 15 minutes at room temperature, lysates were collected, clarified by centrifugation, and then 20 µl of lysate was assayed for firefly and Renilla luciferase using the luminometer from a Biotek Synergy H1 plate reader with a dual injector. The Renilla luciferase is an internal control for each experiment and set of transfections, and the ratio of firefly luciferase over Renilla luciferase is reported herein.

Accession Code

The atomic coordinates and structure factors of the binary complex of RIG-I 191 (ΔCARDs:1-229): 5'OH-GC10 and the ternary complex of RIG-I (ΔCARDs:1-229): 5'OH-GC10: ADP-Mg$^2$ have been deposited with the RCSB Protein Data Bank under the accession codes 3zd6 and 3zd7. The ternary complex of RIG-I (ΔCARDs:1-229): 5'OH-GC10: $SO_4^{2+}$ is already available under the accession code 2ykg and has been previously published (Luo et al., 2011, Cell 147:409-422).

The results of the experiments are now described.

Further description of the data presented herein may be found in Kohlway et al., 2013, EMBO Rep, 14(9): 772-9, the contents of which are incorporated herein by reference in its entirety.

HEL2i Movements Contribute to dsRNA Recognition

To understand the conformational changes that RIG-I undergoes during RNA recognition and surveillance, the conformations of RIG-I (ΔCARDs: 1-229) was visualized in complex with 5'OH-GC10 (FIG. 1A, Table 1), which show well-ordered scanning movements of the HEL2i domain along the duplex RNA backbone. Conformation 1 is the binary complex of RIG-I (ΔCARDs:1-229): 5'OH-GC10, in which the ATP-binding pocket is empty and HEL2i stays in the most compact state (FIG. 1A; pdb:3zd6). Conformation 2 is the previously reported crystal structure and is the ternary complex of RIG-I (ΔCARDs:1-229): 5'OH-GC10: $SO_4^{2-}$, in which the sulphate ion occupies the ATP-binding pocket and HEL2i adopts an intermediate state (FIG. 1A, pdb:2ykg) (Luo et al., 2011, Cell 147:409-422). Conformation 3 is also a ternary complex of RIG-I (ΔCARDs:1-229): 5'OH-GC10: ADP-Mg$^{2+}$, in which ADP-Mg$^{2+}$ occupies the ATP-binding pocket and HEL2i adopts the most extended state (FIG. 1A; pdb:3zd7).

Figure 1E:
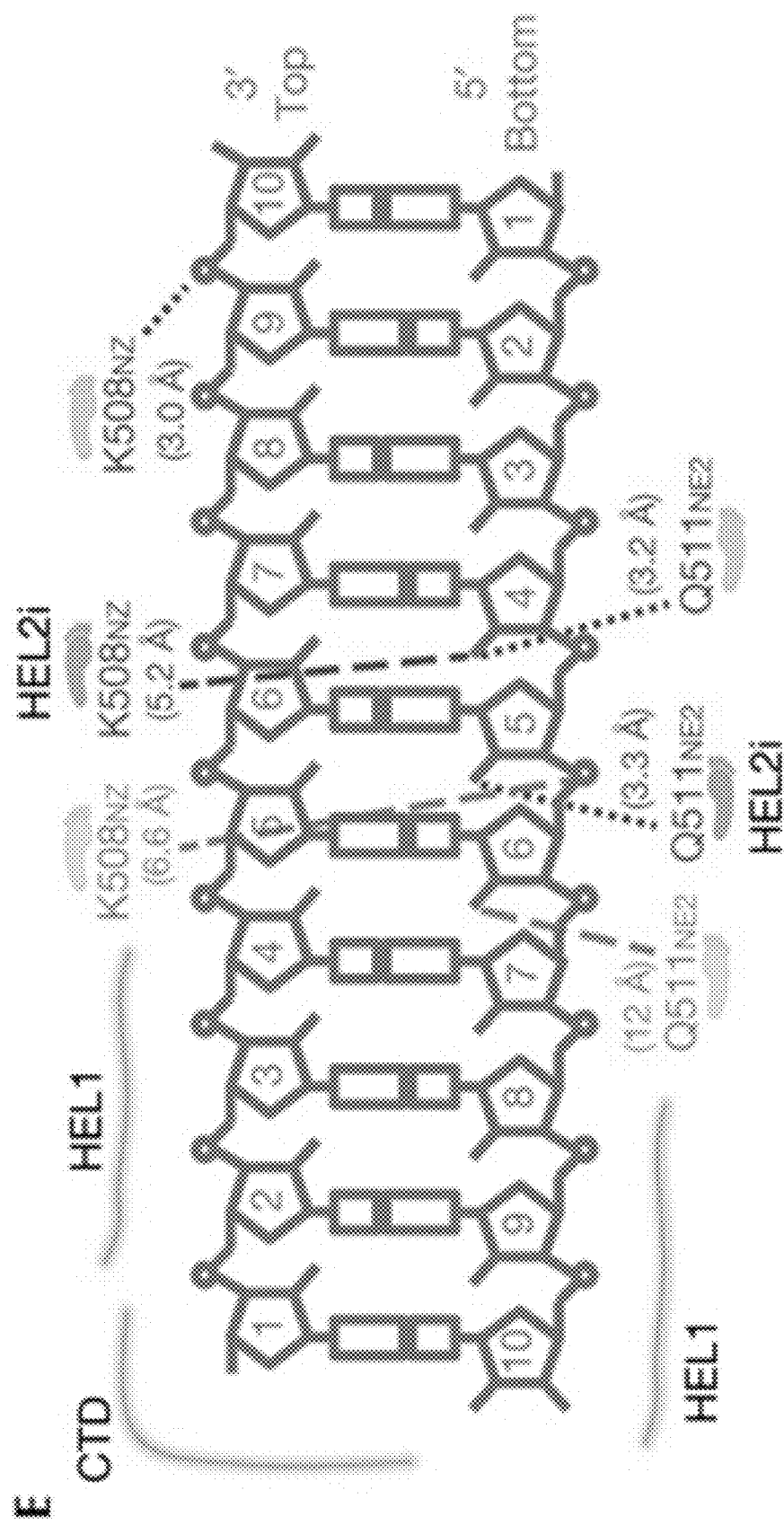

An alignment of the three RIG-I:RNA structures reveals that, while the HEL1-RNA-CTD forms a rigid sandwich-like fold, the HEL2i domain of RIG-I is flexible and makes sequential contacts with several base pairs along the RNA duplex. Specifically, the HEL2i domain scans along the duplex backbone between bases four through six of the 3' bottom strand (that is, the 'tracking strand' for SF2 helicase proteins) when transitioning between conformations, and then makes contact with the top strand in the extended, ADP-bound conformation (FIG. 1B). Two residues of the HEL2i domain, K508 and Q511, engage the RNA duplex: Q511 does not form contacts with the RNA backbone in conformation 1; in conformation 2, Q511 interacts with the 2'—OH group of the fifth base of the bottom strand; in conformation 3, Q511 reaches the 2'OH group of the fourth base as the HEL2i domain slides along one face of the RNA duplex. K508 comes into close contact with the RNA only in the extended conformation 3, forming a salt bridge with the phosphate at position 9 on the 5' top strand (FIG. 1E).

During scanning, the pincer domain facilitates coordinated motion of HEL2-HEL2i relative to HEL1 by engaging in a swinging motion along the more N-terminal α-helix whereas the C-terminal arm of the pincer serves as an anchor by remaining rigidly stacked against HEL1 (FIG. 1C). Subtle changes in the ATP-binding pocket among the conformations are also observed, including movements of the phosphate-binding loop and K270 of motif I, suggesting that the pincer and HEL2i motions might be linked to ATP-binding and hydrolysis (FIG. 1D) (Luo et al., 2012b, Structure, 20:1983-1988). Collectively, these conformations show dynamic opening and closing motions of the HEL2i domain along a 10 base pair stretch of RNA. This led to the further investigation of two questions: (1) How important are more RNA pairings that extend beyond this central core of 10 base pairs at the helical terminus? That is, do more base pairs contribute to duplex RNA binding, stimulation of in vitro ATPase activity, or RIG-I-mediated IFN production? (2) How many RIG-I molecules are necessary per RNA molecule to activate both ATPase activity and an IFN response?

RIG-I Binds Duplex RNA Termini as a Monomer

Figure 2:
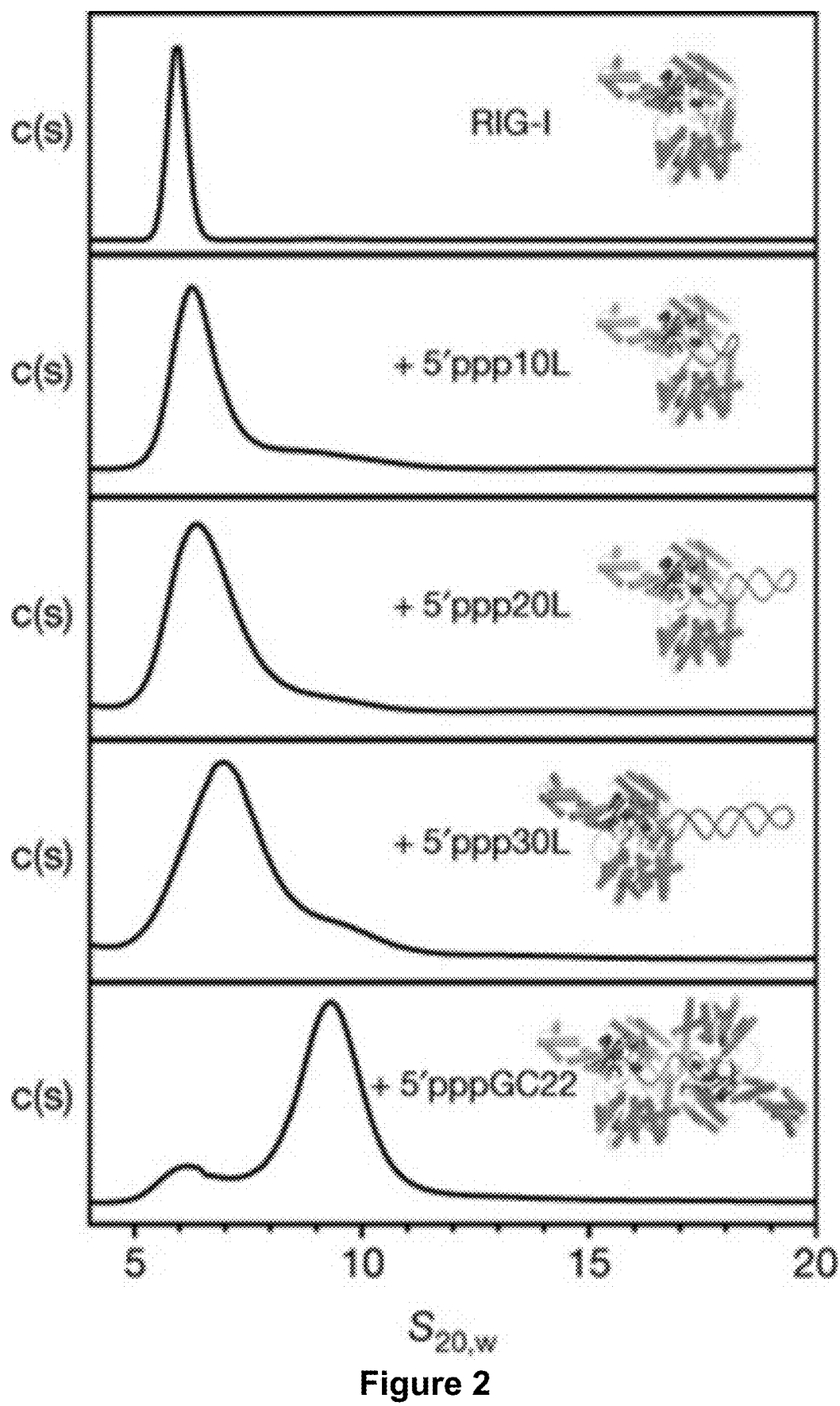
FIG. 2 is a set of graphs depicting the results of an experiment demonstrating that RIG-I binds hairpins with one triphosphate with a 1:1 stoichiometry. Hydrodynamic analysis of RIG-I in complex with 5'ppp10L, 5'ppp20L, 5'ppp30L and 5'pppGC22 RNA. c(s) distributions for each SV experiment were plotted against the sedimentation coefficient ($s_{20,w}$). Peak $s_{20,w}$ values for each distribution are 6.0 for RIG-I alone and 6.2, 6.4, 6.9 and 9.3 for RIG-I: 5'ppp10L, 5'ppp20L, 5'ppp30L and 5'pppGC22 complexes, respectively. Estimated molecular weights from Sedfit are 106 kDa ($f/f_0$=1.31), 113 kDa ($f/f_0$=1.31), 121 kDa ($f/f_0$=1.53), 133 kDa ($f/f_0$=1.57) and 228 kDa ($f/f_0$=1.45), respectively. Models of RIG-I bound to each RNA construct are shown next to each c(s) distribution. RIG-I, retinoic acid-inducible gene-I; SV, sedimentation velocity.

To study RIG-I binding to the internal duplex RNA regions, a family of structurally well-defined RNA hairpins was synthesized in which the duplex length was varied, but one terminus was blocked by the presence of a structured, RNA tetraloop. A hydrodynamic method, sedimentation velocity (SV), was employed to monitor populations of RIG-I and RIG-I:RNA complexes that form in the solution using hairpin duplexes of 10, 20 and 30 base pairs in length, each bearing a single 5'triphosphorylated end (5'ppp10L, 5'ppp20L, and 5'ppp30L, Table 2). In addition, we examined RIG-I binding to a 22mer duplex RNA that contains two 5'triphosphorylated ends (5'pppGC22). It was observed that, at micromolar concentrations of protein and RNA, RIG-I formed 1:1 complexes with each hairpin tested, regardless of duplex length (FIG. 2). Specifically, peak $s_{20,w}$ (standardized to 20° C. and water) values of 6.0 for RIG-I alone, and 6.2, 6.4 and 6.9 for excess RIG-I with hairpins of lengths 10, 20 and 30, respectively, were determined. By contrast, the complex of RIG-I with 5'pppGC22 had a $s_{20,w}$ of 9.3, indicating a 2:1 protein:RNA stoichiometry.

Kowalinksi et at (Kowalinski et al., 2011, Cell 147:423-435) also demonstrated that RIG-I binds with a 2:1 stoichiometry to a longer dsRNA that has two blunt termini (61mer). This is consistent with the present SV analysis, and taken together, these results show that RIG-I specifically recognizes the base-paired terminus of duplex RNA, and that RIG-I does not form protein—protein-mediated oligomers even in the presence of RNA (and ADP/ATP analogs, as shown in Luo et al (Luo et al., 2012b, Structure, 20:1983-1988)). Internal binding within the duplex is neither strongly favorable nor required for strong monomeric binding at the 5' end.

TABLE 2

Nucleic acid molecules used

| Name | Sequence and Chemical Composition |
|---|---|
| GC8 | 5'OH-GCGCGCGC-3' (SEQ ID NO: 1) |
| GC10 | 5'OH-GCGCGCGCGC-3' (SEQ ID NO: 2) |
| GC12 | 5'OH-GCGCGCGCGCGC-3' (SEQ ID NO: 3) |
| GC14 | 5'OH-GCGCGCGCGCGCGC-3' (SEQ ID NO: 4) |
| GC18 | 5'OH-GCGCGCGCGCGCGCGCGC-3' (SEQ ID NO: 5) |
| GC22 | 5'OH-GCGCGCGCGCGCGCGCGCGCGC-3' (SEQ ID NO: 6) |
| 5'pppGC10 | 5'ppp-GGCGCGCGCC-3' (SEQ ID NO: 7) |
| 5'pppGC12 | 5'ppp-GGCGCGCGCGCC-3' (SEQ ID NO: 8) |
| 5'pppCM12 | 5'ppp-GGACGUACGUCC-3' (SEQ ID NO: 9) |
| 5'pppGC22 | 5'ppp-GGCGCGCGCGCGCGCGCGCGCC-3' (SEQ ID NO: 10) |
| 5'ppp8L | 5'ppp-GGCGCGGC UUCG GCCGCG CC-3' (SEQ ID NO: 11) |
| 5'ppp10L | 5'ppp-GGACGUACGU UUCG ACGUACGUCC-3' (SEQ ID NO: 12) |
| 5'ppp10L | 5'pppGGAUCGAUCGAUCGAUCGGCUUCGGCCGAUCG AUCGAUCGAUCC-3' (SEQ ID NO: 13) |
| 5'ppp30L | 5'pppGGAUCGAUCGAUCGAUCGGCAUCGAUCGGCUUC GGCCGAUCGAUGCCGAUCGAUCGAUCGAUCC-3' (SEQ ID NO: 14) |
| polyI: C | 5'OH-I$^n$: C$^n$-3' (0.02- 1 kilo base pairs) |

RIG-I ATPase Activity is Dependent on Poly I:C Ends

To calibrate the present findings with those in the literature, RIG-I:RNA interactions were examined using a polymer that is more typically used in studies of RIG-I. Specifically, RNA-stimulated ATPase activity was analyzed using poly I:C, which is a synthetic analogue of double-stranded RNA that is commonly used for experimental stimulation of an IFN response. The ATPase activity of RIG-I is strictly dependent on the concentration of RNA, therefore the enzymatic activity of RIG-I can be used as a metric for productive binding to poly I:C, or any other RNA polymer. Poly I:C is a mixture of lengths and RNA conformational states, and it was thus hypothesized that RIG-I ATPase activity will be more efficiently stimulated by shorter poly I:C fragments because they have more accessible ends per base pair. To test this hypothesis, an analysis of RIG-I ATPase stimulation by low-molecular weight (LMW) poly I:C (FIG. 6), which is a mixture of ~25-500 base pair fragments, was conducted. To reduce heterogeneity of the poly I:C sample, the poly I:C was fractionated on an analytical Superdex 200 column to create seven fractions of decreasing size (FIG. 3A). The mean length of each fraction was estimated, making the assumption that each fraction was a discrete size, and thereby converted between ng/μl and nanomolar amounts of poly I:C strands (Table 3). Individual fractions were tested for the ability to stimulate RIG-I ATPase activity by varying the poly I:C fraction concentration at 5 mil ATP ($K_{m,RNA}$, FIG. 3B) or by varying the ATP concentration at 15 ng/μl poly I:C fraction ($K_{m,ATP}$, FIG. 3C). Remarkably, a clear trend was found, demonstrating that shorter poly I:C fragments stimulated RIG-I ATPase activity more effectively. The $K_{m,RNA}$ for every fraction was plotted in terms of both rig/and nM poly strands (FIG. 3D). Whereas the $K_{m,RNA}$ spanned a 10-fold range when expressed in ng/μl, the $K_{m,RNA}$ varied approximately two-fold or less when expressed in molarity of poly I:C strands. In fact, an identical $K_{m,RNA}$ value of 20 nM was observed for both fractions A1 and A7, which are at two extremes in terms of length, and the $K_{m,RNA}$ values for the other fractions were similar to this, within error. Furthermore, $K_{m,ATP}$ values for each fraction of poly I:C (at saturating number of ends) were between ~600 and 700 μM ATP (FIG. 3C). These data demonstrate that RIG-I ATPase activity is dependent on the number of duplex ends that are available in each poly I:C fraction, and they corroborate the view that internal duplex regions are not critical for the enzymatic function of RIG-I.

TABLE 3

Poly I:C ng/μl to nanomolar concentrations. The estimates for the length of each fraction of poly I:C as well as the approximate molecular weights (FIG. 3A). The ng/μl concentrations used in the poly I:C $K_{m,RNA}$ experiment were converted to nanomolar of poly I:C strands based on the estimated length and molecular weights of each poly I:C strand.

| Poly I:C (ng/μL) | A1 (nM) | A2 (nM) | A3 (nM) | A4 (nM) | A5 (nM) | A6 (nM) | A7 (nM) |
|---|---|---|---|---|---|---|---|
| 0.00 | 0.00 | 0.00 | 0.00 | 0.00 | 0.00 | 0.00 | 0.00 |
| 0.01 | 0.04 | 0.06 | 0.12 | 0.24 | 0.36 | 0.55 | 0.87 |
| 0.03 | 0.09 | 0.12 | 0.24 | 0.48 | 0.73 | 1.09 | 1.75 |
| 0.06 | 0.17 | 0.24 | 0.48 | 0.97 | 1.45 | 2.18 | 3.49 |
| 0.12 | 0.35 | 0.48 | 0.97 | 1.94 | 2.91 | 4.36 | 6.98 |
| 0.23 | 0.70 | 0.97 | 1.94 | 3.88 | 5.82 | 8.73 | 13.96 |
| 0.47 | 1.40 | 1.94 | 3.88 | 7.76 | 11.64 | 17.45 | 27.93 |
| 0.94 | 2.79 | 3.88 | 7.76 | 15.51 | 23.27 | 34.91 | 55.85 |
| 1.88 | 5.59 | 7.76 | 15.51 | 31.03 | 46.54 | 69.82 | 111.71 |
| 3.75 | 11.17 | 15.51 | 31.03 | 62.06 | 93.09 | 139.63 | 223.41 |
| 7.50 | 22.34 | 31.03 | 62.06 | 124.12 | 186.18 | 279.26 | 446.82 |
| 15.00 | 44.68 | 62.06 | 124.12 | 248.24 | 372.35 | 558.53 | 893.65 |
| Length | 500 | 360 | 180 | 90 | 60 | 40 | 25 |
| MW | 335703 | 241706.16 | 120853.08 | 60426.54 | 40284.36 | 26856.24 | 16785.15 |

The Minimal RNA for Stimulating RIG-I ATPase Activity

To more precisely define the minimal duplex length for enzymatic activation of RIG-I, the steady-state kinetic parameters for RIG-I activation by RNA hairpins and double-stranded duplexes ranging in size from 8 to 30 base pairs, was measured with and without a 5'triphosphate (RNAs listed in Table 2). In order to evaluate the respective roles of ATP and RNA in activation of the RIG-I:RNA complex, the Michaelis constant for ATP ($K_{m,ATP}$) at saturating RNA (500 nM) and the Michaelis constant for RNA ($K_{m,RNA}$) at saturating ATP (5 mM) was measured for each RNA construct ($k_{cat}$, $K_{m,ATP}$ and $K_{m,RNA}$ summary in Table 4).

Four 5'triphosphorylated RNA hairpins with duplex lengths of 8, 10, 20 and 30 base pairs were tested for stimulation of RIG-I ATPase activity (FIG. 4 and FIG. 7). The 5'ppp8L and 5'ppp10L hairpins displayed the largest disparity in $k_{cat}$, doubling from 7.45 s$^{-1}$ to 14.32 s$^{-1}$ (ATP molecules hydrolysed per second per molecule of RIG-I) on the addition of only two base pairs. The two larger constructs, 5'ppp20L and 5'ppp30L, were slightly less effective at stimulation than 5'ppp10L, with $k_{cat}$ values of 12.59 s$^{-1}$ and 9.98 s$^{-1}$, respectively. It is interesting that, the 5'ppp8L hairpin stimulated RIG-I ATPase activity to a lesser degree than 5'ppp10L. This result is intriguing in the context of the structural data, as it provides further support for the hypothesis that two extra base pairs beyond the footprint of RIG-I, as in the 5'ppp10L hairpin, likely provide the HEL2i domain with the required room for full flexibility and the coordinated internal motions that lead to efficient ATP hydrolysis.

In order to more comprehensively evaluate the RNA length dependence for RIG-I ligands, six 'GC' palindromic, blunt-ended, 5'hydroxyl RNA duplexes with lengths of 8, 10, 12, 14, 18 and 22 were tested for stimulation of RIG-I ATPase activity (FIG. 4 and FIG. 7). Remarkably, the $k_{cat}$ values at saturating ATP and RNA concentrations followed the same trends as the 5'triphosphorylated hairpins. The peak ATPase activity occurred with stimulation from GC12, albeit with negligible differences in comparison to stimulation from GC10 or GC14. Taken together, the length dependence of the $k_{cat}$ for the palindromic, 5'hydroxyl duplexes were qualitatively similar to the 5'triphosphorylated hairpins. In each case, robust ATPase activity for RIG-I stimulation was observed with RNA of at least 10 base pairs in length, regardless of the presence of a 5'-triphosphate moiety, and activity declined slightly with increasing duplex length.

TABLE 4

RNA stimulated ATP hydrolysis by RIG-I.

| RNA construct | $k_{cat}$ ± SD(s$^{-1}$RIG-I$^{-1}$) | $K_{m,ATP}$ ± SD(μM) | $K_{m,RNA}$ ± SD(nM) |
|---|---|---|---|
| 5'ppp8L | 7.45 ± 0.90 | 454 ± 18 | 5.16 ± 0.40 |
| 5'ppp10L | 14.3 ± 2.5 | 556 ± 65 | 4.46 ± 0.50 |
| 5'ppp20L | 12.6 ± 1.6 | 604 ± 40 | 10.1 ± 0.50 |
| 5'ppp30L | 9.98 ± 1.3 | 622 ± 100 | 10.8 ± 1.0 |
| GC8 | 7.34 ± 2.6 | 425 ± 66 | 91.4 ± 15 |
| GC10 | 14.4 ± 3.0 | 511 ± 55 | 24.4 ± 1.5 |
| GC12 | 15.9 ± 3.1 | 528 ± 38 | 13.1 ± 1.0 |
| GC14 | 15.1 ± 1.9 | 537 ± 31 | 23.2 ± 1.3 |
| GC18 | 12.5 ± 1.3 | 600 ± 37 | 26.7 ± 3.4 |
| GC22 | 11.3 ± 1.1 | 570 ± 75 | 27.3 ± 1.1 |
| 5'pppGC10 | 18.8 ± 2.8 | 498 ± 35 | 1.16 ± 0.20 |
| 5'pppGC12 | 20.5 ± 3.3 | 535 ± 55 | 2.33 ± 0.20 |
| 5'pppCM12 | 15.9 ± 1.8 | 591 ± 57 | 2.62 ± 0.10 |
| 5'pppGC22 | 12.3 ± 1.9 | 536 ± 39 | 3.58 ± 1.0 |
| LMW poly I:C | 4.90 ± 0.50 | 690 ± 130 | 2.40 ± 1.1 (ng/μl) |

***Note that for the poly I:C $K_{m,ATP}$, the poly I:C concentration was kept at 500 ng/μl. For the poly I:C $K_{m,RNA}$, the poly I:C concentration was varied up to 500 ng/μl.

5'ppp Enhances RNA Binding, but not ATP Hydrolysis

The trends in $k_{cat}$ values for the 5'triphosphorylated hairpins and the 5'hydroxyl duplexes were similar despite tighter RNA binding (reflected by smaller $K_{m,RNA}$ values) by the 5'triphosphorylated hairpins. This finding reveals that the 5'triphosphate might function primarily at the step of binding and that it does not have a major impact on ATP hydrolysis. To further investigate the function of the triphosphate, three 'GC' palindromic blunt-ended RNA duplexes with 5'triphosphates of lengths 10, 12 and 22 were tested for stimulation of RIG-I ATPase activity, as well as a 5'triphosphorylated 12-mer, 5'pppCM12, containing a palindromic but non-uniform sequence including all four nucleotides (FIG. 4 and FIG. 7). Although the $k_{cat}$ for 5'pppGC10 and 5'pppGC12 were marginally higher than GC10 and GC12, the measured $k_{cat}$ for 5'pppCM12 was identical to GC12, and the $k_{cat}$ for 5'pppGC22 was within the experimental error of the $k_{cat}$ for GC22. These data further demonstrate that the triphosphate has a minimal effect on the $k_{cat}$ values for RIG-I ATP hydrolysis when all ligands are saturating.

Figures 4A, 4B:
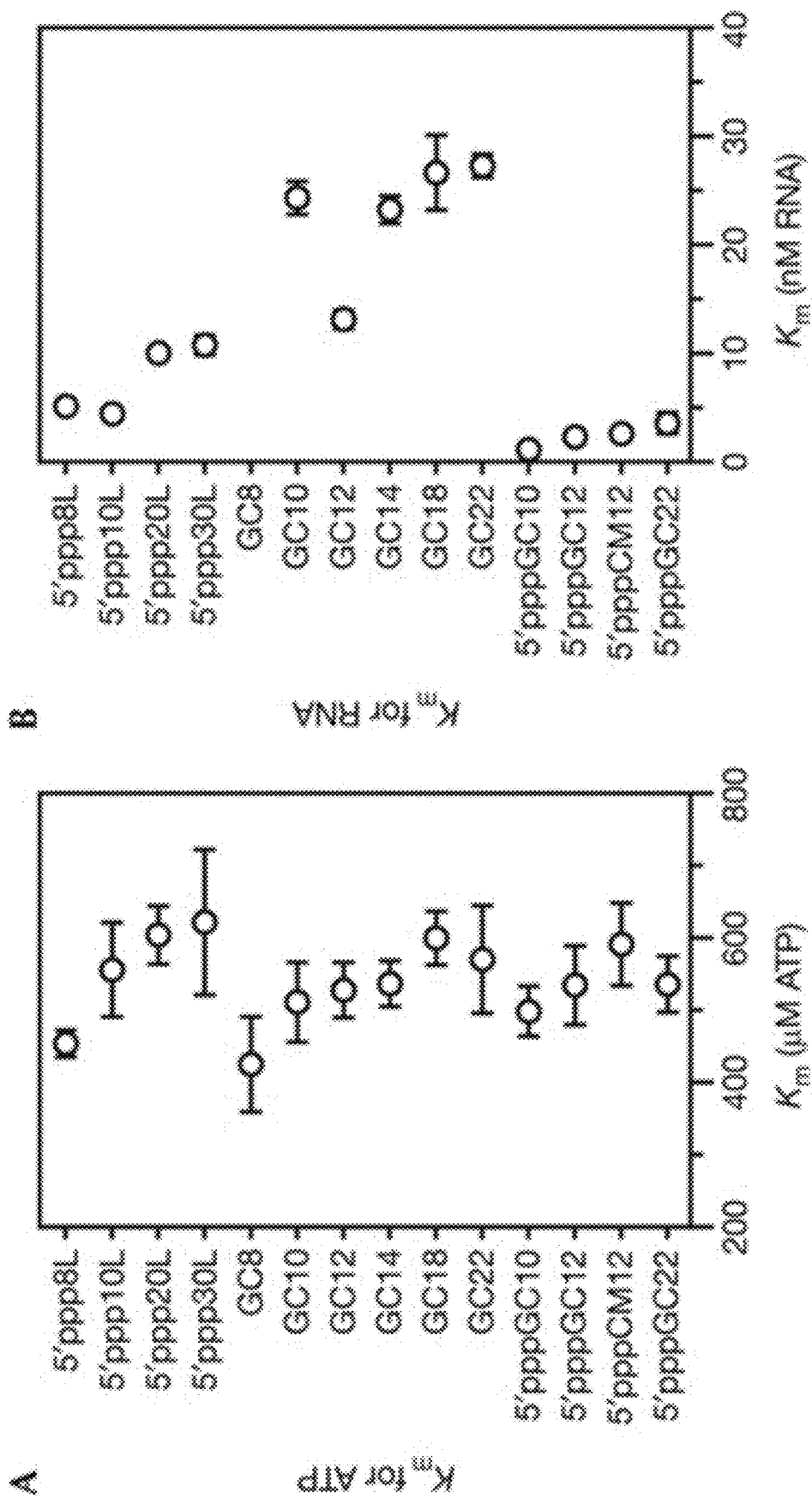
FIG. 4A through FIG. 4D, depicts the results of experiments demonstrating the in vitro and cell culture activities of RIG-I in response to short duplex RNAs.

Only small changes in the measured $K_{m,ATP}$ (the apparent binding constant for ATP) was observed for the RNA constructs tested (FIG. 4A). Specifically, the $K_{m,ATP}$ were between ~500 and 600 µM, implying that the conformational changes in RIG-I that are required for catalysis are not influenced by the presence of a triphosphate moiety or duplex length. This observation is corroborated in part by structural evidence showing that RIG-I binds 5'triphosphorylated RNA identically to 5'hydroxyl RNA (Luo et al., 2012b, Structure, 20:1983-1988).

By contrast, the $K_{m,RNA}$ (the apparent binding constant for RNA) directly correlated with the presence of a 5'triphosphate on the RNA hairpin or duplex (FIG. 4B). The $K_{m,RNA}$ for the four 5'triphosphorylated duplexes were between 1.2 and 3.6 nM, and the $K_{m,RNA}$ for the four 5'triphosphorylated hairpins were between 5.2 and 10.8 nM. However, the 5'hydroxyl RNA duplexes yielded $K_{m,RNA}$ values between 20 and 30 nM, with the exception of GC8 (91 nM) and GC12 (13 nM). These data underscore the fact that any RNA duplex of the appropriate length (>10 bp) can fully stimulate the ATPase activity of RIG-I, but a duplex containing a 5'-triphosphate binds RIG-I with higher affinity and will therefore stimulate ATPase activity at lower RNA concentrations. This finding is an important distinction that explains why only trace amounts of viral RNA might be required to activate the interferon-β (IFN-β) response in infected cells. Interestingly, the poly I:C fractions exhibited a similar range of $K_{m,RNA}$ values as those observed for the 5'hydroxyl duplex RNA, suggesting that RIG-I functions on poly I:C in a manner that is similar to any other RNA duplex that lacks a 5'-triphosphate.

RIG-I ATPase Activity on a Monomeric and Dimeric RNA Ligands Suggests No Functional Intermolecular Interactions Between RIG-I Having identified a series of important intramolecular dynamics that contribute to RIG-I function, the next set of experiments was designed to determine whether functional intermolecular interactions between RIG-I molecules might also play a role in establishing a catalytically competent ternary complex. The ATPase activity of RIG-I was therefore measured at protein concentrations varying between 5 and 50 nM using saturating concentrations of 5'ppp10L hairpin and 5'pppGC22 duplex. Without wishing to be bound by any particular theory, it is believed that if the ATPase activity of RIG-I is modulated by homotypic protein:protein interactions, then the catalytic activity of the protein would be expected to exhibit a non-linear relationship with enzyme concentration.

Figure 10:
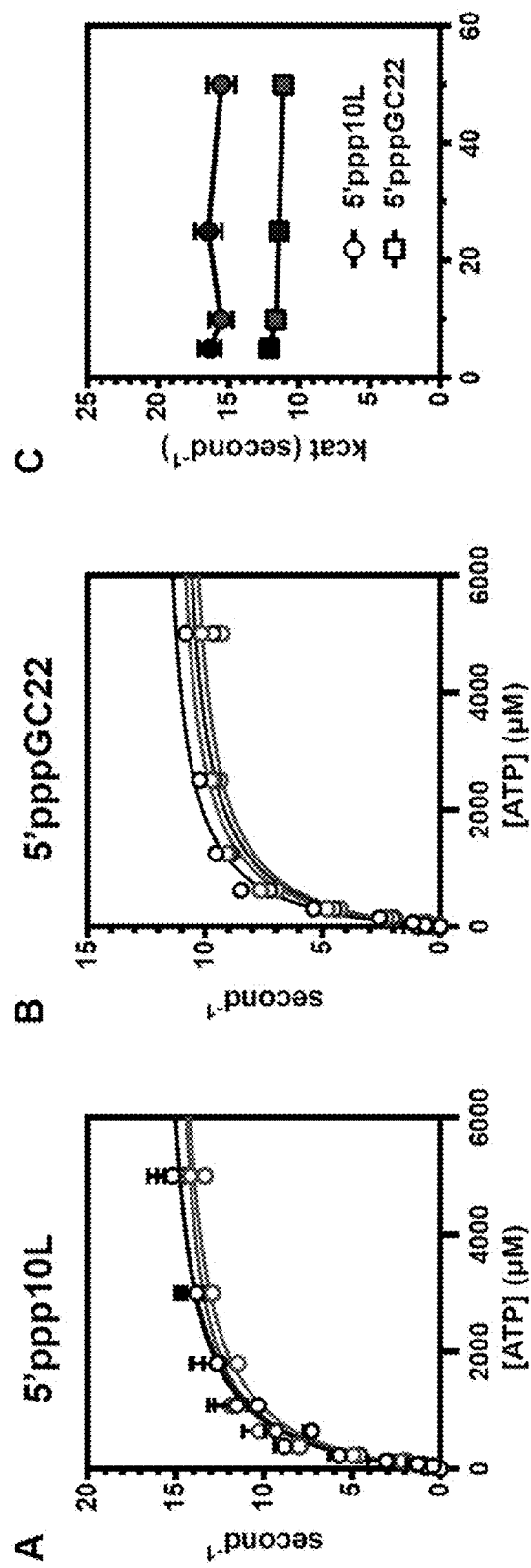
FIG. 10, comprising

The $k_{CAT}$ for RIG-I measured on both 5'ppp10L and 5'pppGC22 does not vary within the ten-fold range of RIG-I concentrations tested (FIG. 10A, FIG. 10B). Additionally, there is an approximate 25% decrease in the measured $k_{CAT}$ between the monomeric RIG-I substrate, 5'ppp10L, and the dimeric RIG-I substrate, 5'pppGC22 (FIG. 10C). The lack of a significant change in the $k_{CAT}$, either from an increase in enzyme concentration or from potential 5'pppGC22-induced oligomerization indicates that RIG-I functions optimally as a monomer. These observations indicate that protein-protein interactions do not alter the ability of RIG-I to hydrolyze ATP, either on the same RNA molecule, as with 5'pppGC22, or between RIG-I:RNA complexes.

1:1 RIG-I:RNA Binding is Sufficient to Stimulate IFN-β

Figures 4C, 4D:
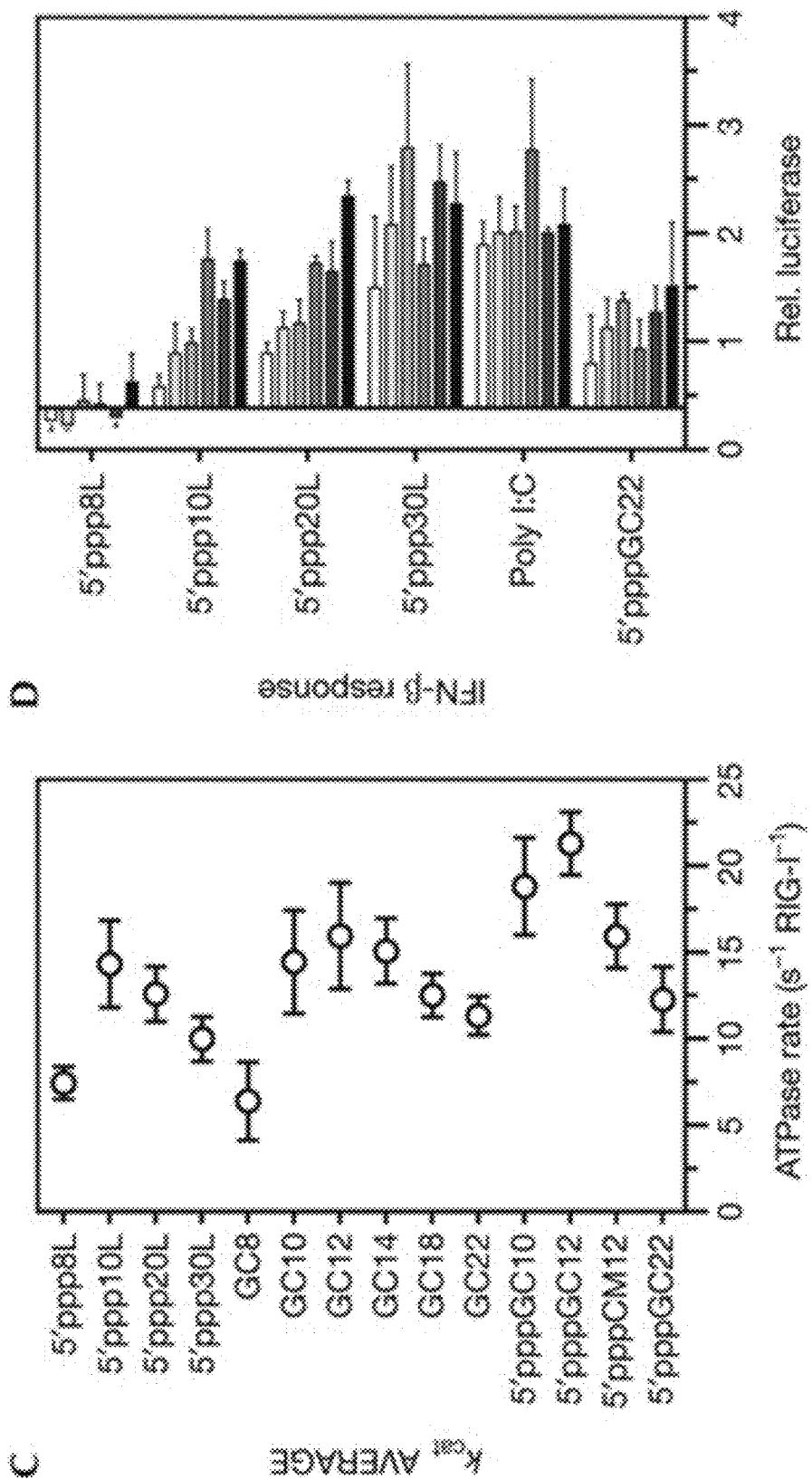

The in vitro SV and RNA-stimulated ATPase studies provide strong evidence that RIG-I activation requires only the 5' terminus of duplex RNA, along with an adjacent 10-12 base pairs. And while RIG-I in vitro activity is typically associated with RNA binding or ATPase activity, the direct relationship to interferon stimulation is not clear. Therefore, it was important to test the relevance of the present in vitro results in cell culture. To accomplish this, the ability of 5'triphosphorylated hairpins and poly I:C fractions to stimulate a RIG-I-mediated IFN-β response in 293T cells was measured (FIG. 4D).

Figure 8:
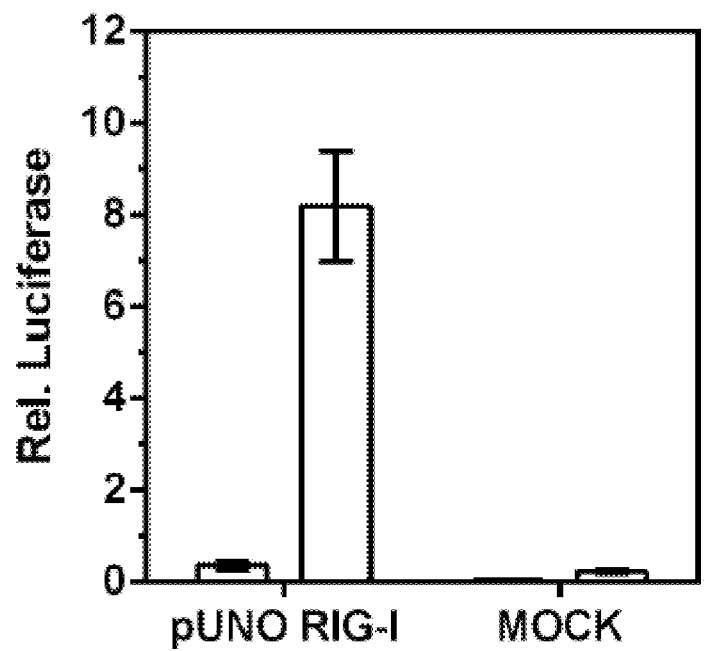
FIG. 8 depicts the result of an experiment using a mock control for HEK293T cell culture IFN production. The IFN-β production in 293T cells overexpressing RIG-I (and a mock control not overexpressing RIG-I) was measured in the absence (left) and presence (right) of poly I:C stimulation. The relative luciferase is the firefly luciferase (IFN-β reporter) divided by the Renilla luciferase. The following protocol was adapted from Luo et. al. (Luo et al, 2011). 293T cells were seeded at 50,000 cells per well in 24 well plates. The next day, 293T cells were transfected with 30 ng of pRLTK, 178 ng of a firefly IFN-β reporter, and 3 ng (or none for mock) of pUNO-RIG-I per well using lipofectin (Invitrogen). After 24 hours, 293T cells were transfected with 1 µg of poly I:C (or none for negative control) using mRNA transfection reagent (MIRUS). After 16 hours, cells were harvested and assayed for firefly and Renilla luciferase using the Promega Dual Luciferase Reporter assay system. Error bars report the standard deviation from 6 experiments for unstimulated and 12 experiments for stimulated.

Remarkably, it was found that three of the four hairpins—5'ppp10L, 5'ppp20L and 5'ppp30L—stimulated an IFN-β response comparable to the positive controls, LMW poly I:C and 5'pppGC22 (mock control in FIG. 8). Both LMW poly I:C and short 19 bp+ RNA duplexes have been shown to be good activators of RIG-I (Kato et al., J Exp Med, 205, 1601-1610; Schlee et al., 2009, Immunity, 31: 25-34).

Figure 11:
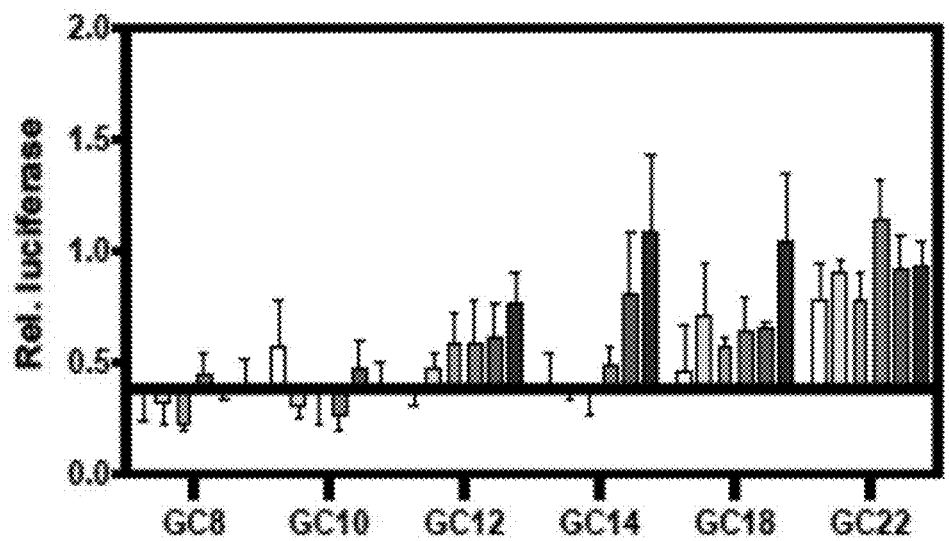
FIG. 11 shows IFN-β stimulation by 5'OH palindromic duplexes. The IFN-β responses to 5'OH palindromic 'GC' duplexes was measured in HEK 293T cells transfected with pUNO-RIG-I, an IFN-β/Firefly luciferase reporter, and a pRL-TK reporter. The charts display the measured relative luciferase ratio of Firefly luminescence over Renilla luminescence from 293T cells in which RIG-I was stimulated by 5'OH 'GC' palindromic duplexes of length of 8, 10, 12, 14, 18, and 22. The range of concentrations for each RNA spans between 20 to 650 nM and are displayed in the figure by a darkening color gradient from low to high RNA concentration. Error bars report the standard error of the mean from 3 measurements.

Further, it is demonstrated that the "GC" palindromic RNAs also stimulate an IFN-β response (FIG. 11). While in certain instances the palindromic RNAs do not exhibit an IFN-β response to the same level as the hairpins, the present data demonstrates that they may be used to promote IFN-β production. While not wishing to be bound by any particular theory, the hairpins may be a superior stimulant for RIG-I simply because of the ability to re-anneal after being unwound, whereas the shorter palindromic duplexes would likely lose their ability to stimulate RIG-I as soon as the duplex melted.

Figure 9:
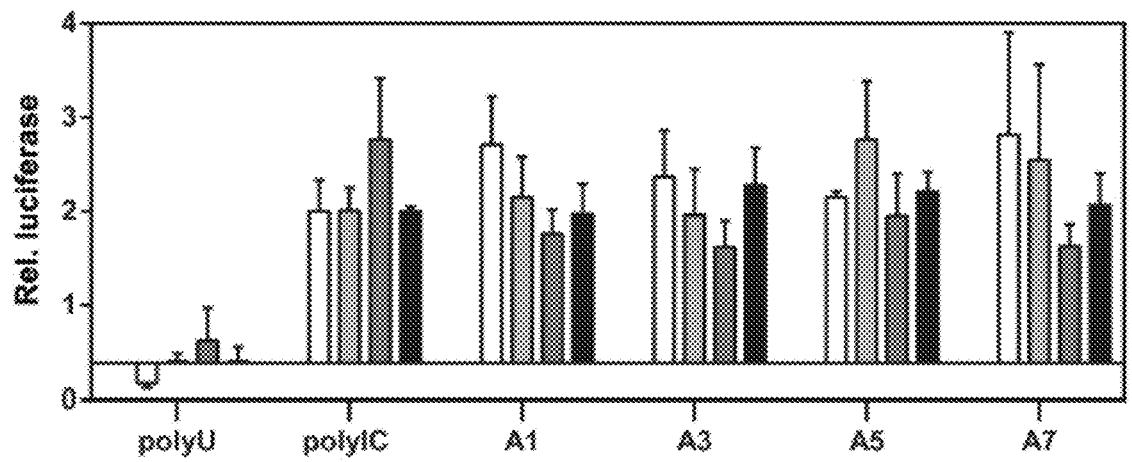
FIG. 9, depicts the results of an experiment examining the cell culture IFN production on different lengths of poly I:C. The IFN-β responses to the fractions of poly I:C was measured in HEK 293T cells transfected with pUNO-RIG-I, an IFN-13/Firefly luciferase reporter, and a pRL-TK reporter (note that the poly I:C data is the same as in FIG. 4D and was done side by side with Fraction A1-A7 shown here). The charts display the measured relative luciferase ratio of Firefly luminescence over Renilla luminescence from 293T cells in which RIG-I was stimulated by the fractions of poly I:C, and also a single stranded poly U and no RNA (serum free media) control. The range of RNA concentrations spans between 31 to 250 ng per well displayed in the figure by a darkening color gradient from low to high RNA concentration. Error bars report the standard error of the mean from 3 measurements.

The IFN-β stimulation from the 5'ppp10L construct is of particular interest because it strongly supports the idea that RIG-I does not survey the cell as an oligomer, that RIG-I does not need to oligomerize on a target RNA duplex strand to elicit an IFN-β response, and that RIG-I does not need to translocate on duplex RNA regions to elicit an IFN-β response. Consistent with these findings, even the shortest poly I:C fragments fully stimulated the IFN response in cells (FIG. 9). The slightly better IFN production, especially at lower RNA concentrations, for 5'ppp20L and 5'ppp30L, can be attributed to the fact that they are more stable duplexes that likely have a longer half-life in the cell.

Model for RNA Surveillance by RIG-I

Recent structural studies have shed new light on RNA surveillance by RIG-I. In all cases, RIG-I is shown to bind RNA molecules as a monomer and to interact specifically with the terminus of an RNA duplex. Indeed, it has been called an end-capper (Kowalinski et al., 2011, Cell, 147: 423-435). Intriguingly, RIG-I is observed to bind all blunt RNA termini in much the same way, without regard to RNA sequence or the presence of a 5'-triphosphate (Jiang et al., 2011, Nature, 479: 423-427; Luo et al., 2011, Cell, 147: 409-422). While these crystallographic observations are useful, they do not establish the minimal length of RIG-I PAMPs in solution for binding, for ATPase activity, and ultimately for signalling in the cell. In addition, the issue of cooperative RIG-I multimerization on RNA has not been squarely addressed. Given the importance of these issues, and of RIG-I activation in general, it was decided to use a combination of techniques to define the minimal RNA PAMP that is required for full activation of RIG-I in vitro and in mammalian cells.

Figure 5:
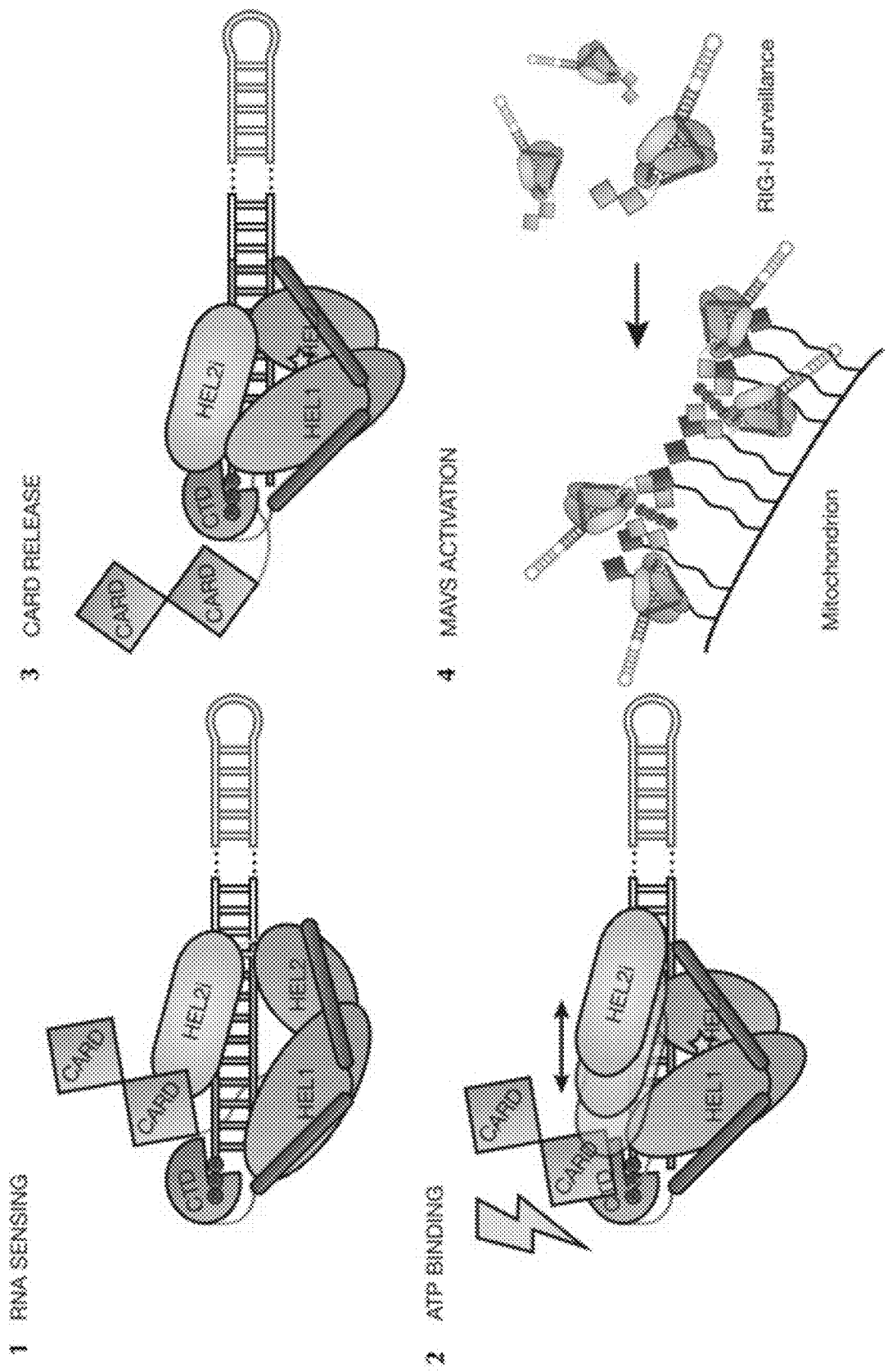
FIG. 5 is a schematic model of RIG-I activation. (1) RNA binding is the first trigger of the RIG-I-mediated interferon response. The CTD binds firmly to the 5' end of the duplex RNA. The CARD domains rest on the HEL2i domain (Kowalinski et al., 2011, Cell, 147: 423-435) and likely are not displaced upon RNA binding. (2) ATP binding serves as the second trigger, whereupon HEL1 and HEL2 close and HEL2 initiates contacts with the tracking strand, creating a clash between the CTD and the CARDs (Luo et al., 2012a, RNA Biol, 10: 111-120). HEL2i scanning might be directly linked to ATP binding and hydrolysis, or it might move stochastically. (3) Once the CARD domains are released, a 1:1:1 RIG-I:RNA:ATP ternary complex is competent for signalling and activation of MAVS. (4) Ubiquitin-mediated multimerization (tetraubiquitin shown in orange) of RIG-I through the CARD domains might be required for MAVS activation (Jiang et al., 2012, Immunity, 36: 959-973; Gack et al., 2007, Nature, 446: 916-920). CARD, caspase activation and recruitment domain; CTD, carboxy-terminal domain; MAVS, mitochondrial antiviral-signalling protein; RIG-I, retinoic acid-inducible gene-I.

The findings presented herein indicate that the minimal RNA PAMP that is required for activation in vitro and in cell culture has been defined, and that determinants under all conditions agree: the RIG-I monomer is activated upon binding the blunt terminus of a RNA duplex. The protein interacts with the 10 base pairs adjacent to the 5' end with an affinity that is enhanced by the presence of a 5'triphosphate. Collectively, the available data in the literature suggest that these 1:1 RIG-I:RNA(end) complexes might then oligomerize into higher order complexes via the CARD domains, resulting in a model that is consistent with findings on downstream events that have been reported by others (FIG. 5) (Jiang et al., 2012, Immunity, 36: 959-973; Gack et al., 2007, Nature, 446: 916-920). As presented herein, the minimal determinants for functional RNA recognition by RIG-I is identified. Further, it is demonstrated that RIG-I uses its functional domains collaboratively to accomplish specific antiviral surveillance in a complex intracellular environment.

Example 2: Ability of Small Hairpin RNAs to Induce Interferon In Vivo

Figure 12:
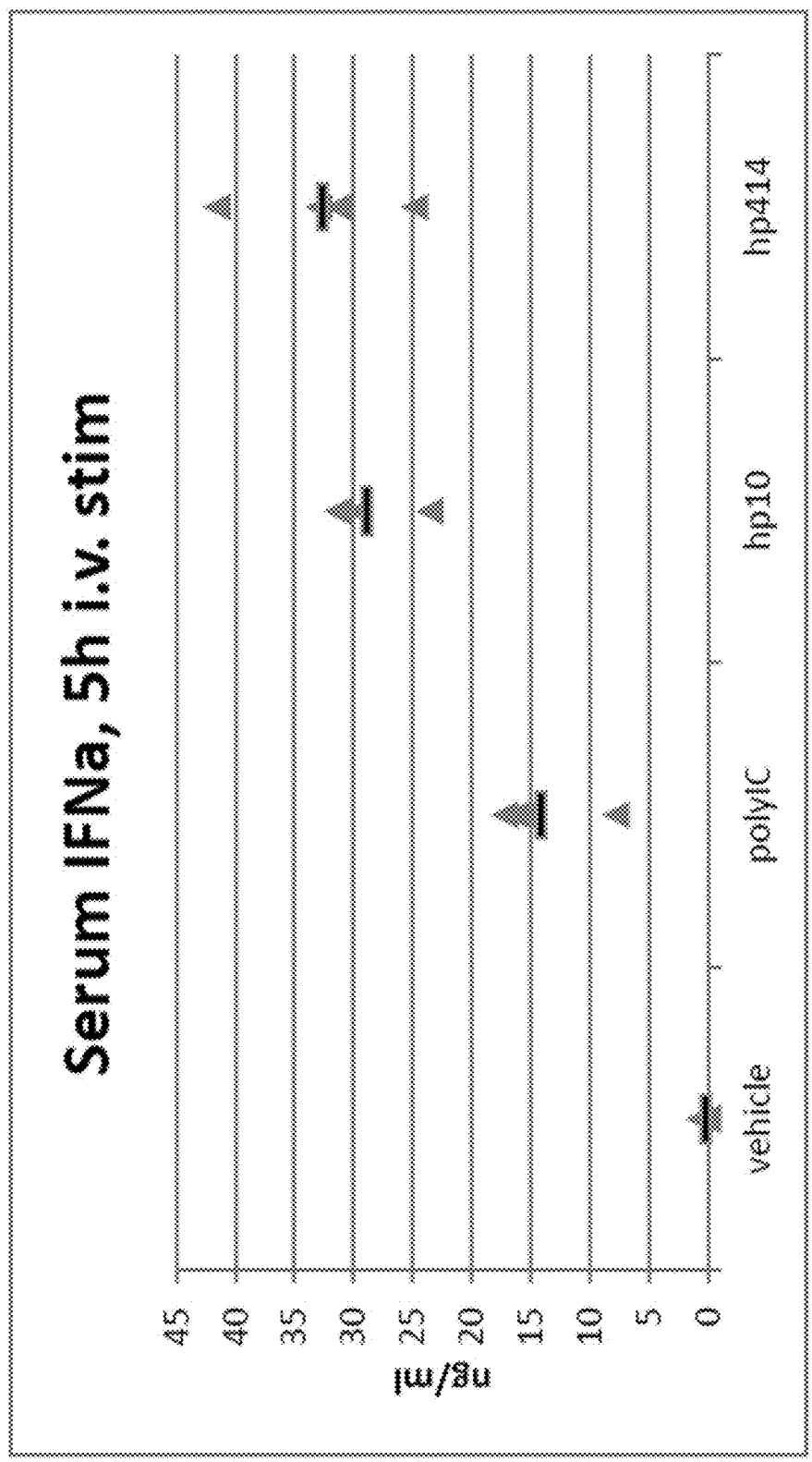
FIG. 12 is a graph depicting the results of a representative experiment depicting serum Interferon alpha levels after treatment with short hairpin RNAs: Mice were injected in the tail vein with jetPEI/RNA complex (i.v.), and serum was collected at 5 hours post-injection. The dose used per mouse was as follows: polyIC=25 ug, hp10=640 uM (25.15 ug), hp414=640 uM (33.4 ug). Four mice were used for each condition. The results indicate that very high levels of IFNalpha are induced by shRNAs and polyIC, and not by the vehicle control. Notably, the shRNAs induce more IFNalpha than polyIC. Note that hp10 is a 5'-triphosphorylated 10 base-pair duplex with a UUCG tetraloop at one end (5'ppp10L from FIG. 4 and FIG. 7) and hp14 is a 5'-triphosphorylated 14 base pair duplex with a UUCG tetraloop at one end. The polyIC is low molecular weight poly IC.

Experiments were conducted to examine the ability of small hairpin RNAs to induce interferon production in vivo. Mice were injected in the tail vein with jetPEI/RNA complex (i.v.), and serum was collected at 5 hours post-injection. The dose used per mouse was as follows: polyIC=25 ug, hp10=640 uM (25.15 ug), hp414=640 uM (33.4 ug). 4 mice were used for each condition. Blood was collected five hours post-injection. The blood was left at 4° overnight to clot. It was then centrifuged for 30 minutes at 4° (3000 prm), and the serum (supernatant) was collected. The results indicate that very high levels of IFNalpha are induced by shRNAs and polyIC, and not by the vehicle control (FIG. 12). Notably, the shRNAs induce more IFNalpha than polyIC. Note that hp10 is a 5'-triphosphorylated 10 base-pair duplex with a UUCG tetraloop at one end (same as 5'ppp10L from FIG. 4 and FIG. 7) and hp14 is a 5'-triphosphorylated 14 base pair duplex with a UUCG tetraloop at one end. The polyIC is low molecular weight poly IC.

Figure 13:
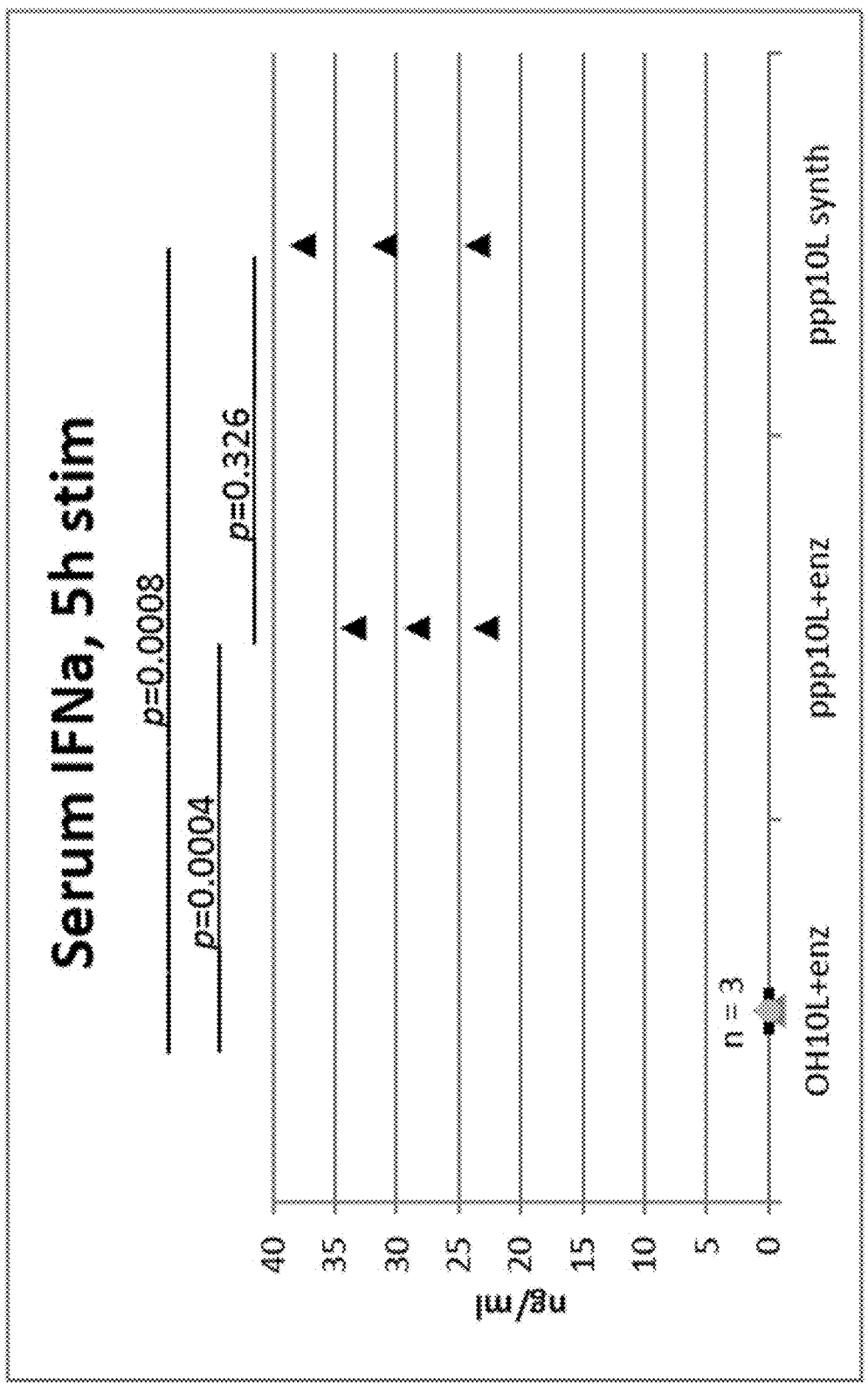
FIG. 13 is a graph depicting the results of a representative experiment depicting serum Interferon alpha levels after treatment with dephosphorylated and triphosphorylated short hairpin RNAs: Mice were injected in the tail vein with jetPEI/RNA complex (i.v.), and serum was collected at 5 hours post-injection, n=3 per group. RNA #1 (center, ppp10L+enz)=5'ppp10L transcribed and then treated with Dnase/Prot K, then phenol extraction and ethanol precipitation. RNA #2 (left, OH 10L+enz)=5'OH10L, which is transcribed 5'ppp10L treated with CIP, then enzyme treated/purified as above. RNA #3 (right, ppp10L synth)=5'ppp10L that is machine-synthesized, abiological. It is demonstrated that only 5'ppp10L (whether transcribed or synthetic), and not RNA lacking triphosphate (left), induces interferon.

Further experiments were conducted to compare IFNα production induced by three different RNA constructs. Mice were injected in the tail vein with jetPEI/RNA complex (i.v.), and serum was collected at 5 hours post-injection, n=3 per group. The first construct is 5'ppp10L transcribed and treated with Dnase/Prot K, purified using phenol extraction and EtOH precipitation. The second construct is 5'OH10L, which is the 5'ppp10L, treated and purified as above, and then treated with CIP. The third construct is a synthesized and abological form of 5'ppp10L. Blood was collected five hours post-injection. The blood was left at 4° overnight to clot. It was then centrifuged for 30 minutes at 4° (3000 prm), and the serum (supernatant) was collected. It was observed that only 5'ppp10L (whether transcribed or synthetic), and not RNA lacking triphosphate, induces interferon (FIG. 13). Both transcribed and synthesized 5'ppp10L induce IFN to a similar degree, although the synthetic triphosphorylated RNA is slightly more active. Extra enzyme treatment and purification of transcribed 5'ppp10L does not impact IFN levels (as compared to data shown in FIG. 12).

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

---

What is claimed is:

1. A ribonucleic acid (RNA) molecule capable of inducing an interferon response,
   wherein the RNA molecule is a single chain molecule and forms a hairpin structure consisting of a double-stranded section, a loop, and a blunt end,
   wherein the number of base pairs in the double stranded section is an integer equal to or greater than 10 and less than 18,
   wherein the molecule comprises a 5'-diphosphate terminus group, and
   wherein the molecule is capable of inducing an interferon response in a vertebrate cell.

2. The molecule of claim 1, which is capable of entering a cell nucleus.

3. The molecule of claim 1, which comprises a modified phosphodiester backbone.

4. The molecule of claim 1, which comprises at least one 2'-modified nucleotide.

5. The molecule of claim 4, wherein the at least one 2'-modified nucleotide comprises a modification selected from the group consisting of: 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), and 2'-O—N-methylacetamido (2'-O-NMA).

6. The molecule of claim 1, which comprises at least one modified phosphate group.

7. The molecule of claim 1, which comprises at least one modified base.

8. The molecule of claim 1, wherein the double-stranded section comprises one or more mispaired bases.

9. A pharmaceutical composition comprising a RNA molecule capable of inducing an interferon response and a pharmaceutically acceptable carrier,
   wherein the RNA molecule is a single chain molecule and forms a hairpin structure consisting of a double-stranded section, a loop, and a blunt end,
   wherein the number of base pairs in the double stranded section is an integer equal to or greater than 10 and less than 18, wherein the RNA molecule comprises a 5'-terminus group selected from the group consisting of a 5'-triphosphate and a 5'-diphosphate, wherein the molecule is capable of inducing an interferon response in a vertebrate cell.

10. The pharmaceutical composition of claim 9, further comprising at least one agent selected from the group consisting of an immunostimulatory agent, an antigen, an anti-viral agent, an anti-bacterial agent, an anti-tumor agent, retinoic acid, IFN-α, and IFN-β.

11. The molecule of claim 1, which comprises at least one abasic nucleotide.

12. The pharmaceutical composition of claim 9, wherein the RNA molecule comprises at least one abasic nucleotide.

13. A ribonucleic acid (RNA) molecule capable of inducing an interferon response,
  wherein the RNA molecule is a single chain molecule and forms a hairpin structure consisting of a double-stranded section, a loop, and a blunt end,
  wherein the number of base pairs in the double stranded section is equal to or greater than 10 and less than 18, and
  wherein the molecule comprises a 5'-triphosphate terminus group,
  wherein the molecule is capable of inducing an interferon response in a vertebrate cell.

14. The molecule of claim 13, which is capable of entering a cell nucleus.

15. The molecule of claim 13, which comprises a modified phosphodiester backbone.

16. The molecule of claim 13, which comprises at least one 2'-modified nucleotide.

17. The molecule of claim 16, wherein the at least one 2'-modified nucleotide comprises a modification selected from the group consisting of: 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), and 2'-O—N-methylacetamido (2'-O-NMA).

18. The molecule of claim 13, which comprises at least one modified phosphate group.

19. The molecule of claim 13, which comprises at least one modified base.

20. The molecule of claim 13, wherein the double-stranded section comprises one or more mispaired bases.

21. The molecule of claim 13, which comprises at least one abasic nucleotide.

* * * * *

SEQUENCE LISTING

```
<160> NUMBER OF SEQ ID NOS: 14

<210> SEQ ID NO 1
<211> LENGTH: 8
<212> TYPE: RNA
<213> ORGANISM: Artificial Sequence
<220> FEATURE:
<223> OTHER INFORMATION: Chemically synthesized

<400> SEQUENCE: 1 gcgcgcgc                                                                    8

<210> SEQ ID NO 2
<211> LENGTH: 10
<212> TYPE: RNA
<213> ORGANISM: Artificial Sequence
<220> FEATURE:
<223> OTHER INFORMATION: Chemically synthesized

<400> SEQUENCE: 2
gcgcgcgcgc                                                                 10

<210> SEQ ID NO 3
<211> LENGTH: 12
<212> TYPE: RNA
<213> ORGANISM: Artificial Sequence
<220> FEATURE:
<223> OTHER INFORMATION: Chemically synthesized

<400> SEQUENCE: 3
gcgcgcgcgc gc                                                              12

<210> SEQ ID NO 4
<211> LENGTH: 14
```

```
<212> TYPE: RNA
<213> ORGANISM: Artificial Sequence
<220> FEATURE:
<223> OTHER INFORMATION: Chemically synthesized

<400> SEQUENCE: 4
gcgcgcgcgc gcgc                                                        14

<210> SEQ ID NO 5
<211> LENGTH: 18
<212> TYPE: RNA
<213> ORGANISM: Artificial Sequence
<220> FEATURE:
<223> OTHER INFORMATION: Chemically synthesized

<400> SEQUENCE: 5
gcgcgcgcgc gcgcgcgc                                                    18

<210> SEQ ID NO 6
<211> LENGTH: 22
<212> TYPE: RNA
<213> ORGANISM: Artificial Sequence
<220> FEATURE:
<223> OTHER INFORMATION: Chemically synthesized

<400> SEQUENCE: 6
gcgcgcgcgc gcgcgcgcgc gc                                               22

<210> SEQ ID NO 7
<211> LENGTH: 10
<212> TYPE: RNA
<213> ORGANISM: Artificial Sequence
<220> FEATURE:
<223> OTHER INFORMATION: Chemically synthesized

<400> SEQUENCE: 7
ggcgcgcgcc                                                             10

<210> SEQ ID NO 8
<211> LENGTH: 12
<212> TYPE: RNA
<213> ORGANISM: Artificial Sequence
<220> FEATURE:
<223> OTHER INFORMATION: Chemically synthesized

<400> SEQUENCE: 8
ggcgcgcgcg cc                                                          12

<210> SEQ ID NO 9
<211> LENGTH: 12
<212> TYPE: RNA
<213> ORGANISM: Artificial Sequence
<220> FEATURE:
<223> OTHER INFORMATION: Chemically synthesized

<400> SEQUENCE: 9
ggacguacgu cc                                                          12

<210> SEQ ID NO 10
<211> LENGTH: 22
<212> TYPE: RNA
<213> ORGANISM: Artificial Sequence
<220> FEATURE:
<223> OTHER INFORMATION: Chemically synthesized

<400> SEQUENCE: 10
```

```
ggcgcgcgcg cgcgcgcgcg cc                                              22

<210> SEQ ID NO 11
<211> LENGTH: 20
<212> TYPE: RNA
<213> ORGANISM: Artificial Sequence
<220> FEATURE:
<223> OTHER INFORMATION: Chemically synthesized

<400> SEQUENCE: 11
ggcgcggcuu cggccgcgcc                                                 20

<210> SEQ ID NO 12
<211> LENGTH: 24
<212> TYPE: RNA
<213> ORGANISM: Artificial Sequence
<220> FEATURE:
<223> OTHER INFORMATION: Chemically synthesized

<400> SEQUENCE: 12
ggacguacgu uucgacguac gucc                                            24

<210> SEQ ID NO 13
<211> LENGTH: 44
<212> TYPE: RNA
<213> ORGANISM: Artificial Sequence
<220> FEATURE:
<223> OTHER INFORMATION: Chemically synthesized

<400> SEQUENCE: 13
ggaucgaucg aucgaucggc uucggccgau cgaucgaucg aucc                      44

<210> SEQ ID NO 14
<211> LENGTH: 64
<212> TYPE: RNA
<213> ORGANISM: Artificial Sequence
<220> FEATURE:
<223> OTHER INFORMATION: Chemically synthesized

<400> SEQUENCE: 14
ggaucgaucg aucgaucggc aucgaucggc uucggccgau cgaugccgau cgaucgaucg     60
aucc                                                                  64
```